(12) United States Patent
Stearns et al.

(10) Patent No.: US 9,095,372 B2
(45) Date of Patent: Aug. 4, 2015

(54) SYSTEM AND METHOD FOR IMPROVED GAS RECIRCULATION IN SURGICAL TROCARS WITH PNEUMATIC SEALING

(71) Applicant: SurgiQuest, Inc., Milford, CT (US)

(72) Inventors: Ralph Stearns, Bozrah, CT (US); Kurt Azarbarzin, Fairfield, CT (US); Timothy J. Nolan, South Salem, NY (US)

(73) Assignee: SurgiQuest, Inc. CT (US)

( * ) Notice: Subject to any disclaimer, the term of this patent is extended or adjusted under 35 U.S.C. 154(b) by 3 days.

(21) Appl. No.: 14/298,419

(22) Filed: Jun. 6, 2014

(65) Prior Publication Data

US 2014/0309583 A1    Oct. 16, 2014

Related U.S. Application Data

(63) Continuation of application No. 14/268,408, filed on May 2, 2014, which is a continuation of application No. 12/587,584, filed on Oct. 9, 2009, now Pat. No. 8,715,219.

(60) Provisional application No. 61/104,448, filed on Oct. 10, 2008.

(51) Int. Cl.
*A61B 17/34* (2006.01)
*A61M 13/00* (2006.01)
*A61B 17/00* (2006.01)

(52) U.S. Cl.
CPC ......... *A61B 17/3474* (2013.01); *A61B 17/3498* (2013.01); *A61M 13/003* (2013.01);

(Continued)

(58) Field of Classification Search
CPC ............... A61M 13/003; A61M 2202/0007; A61M 2202/0225; A61M 13/00; A61M 2202/0208; A61M 16/109; A61M 2210/1017; A61M 25/007; A61M 2005/006; A61B 1/012; A61B 1/018
USPC .............. 604/23–26, 506, 156–161, 264, 272
See application file for complete search history.

(56) References Cited

U.S. PATENT DOCUMENTS 5,013,294 A    5/1991    Baier
5,360,396 A    11/1994   Chan (Continued)

FOREIGN PATENT DOCUMENTS

WO    WO-2008077080 A2    6/2008

OTHER PUBLICATIONS

International Search Report dated May 28, 2010.

*Primary Examiner* — Nicholas Lucchesi
*Assistant Examiner* — Weng Lee
(74) *Attorney, Agent, or Firm* — Locke Lord LLP; Scott D. Wofsy; Arpita G. Buesing

(57) ABSTRACT

Systems for insufflation and recirculation of insufflation fluid in a surgical procedure include a control unit having a fluid pump, a supply conduit, a return fluid conduit and a pressure-controlled valve. The pressure-controlled valve is in fluid communication with an insufflation gas supply, the supply conduit and the return conduit and is adapted and configured to respond to pressure control signals to adjust position and thereby system flow parameters, to reduce entrainment of air from the surrounding environment, and to increase the concentration of insufflation gas in an operative space, and/or to reduce an overpressure condition in the operative space.

11 Claims, 52 Drawing Sheets

(52) U.S. Cl.
CPC .......... *A61M13/006* (2014.02); *A61B 17/3421* (2013.01); *A61B 17/3462* (2013.01); *A61B 2017/00544* (2013.01); *A61M 2205/3337* (2013.01)

(56) References Cited

U.S. PATENT DOCUMENTS

| | | | |
|---|---|---|---|
| 6,733,479 B1 * | 5/2004 | Ott | 604/264 |
| 7,476,212 B2 * | 1/2009 | Spearman et al. | 604/23 |
| 7,722,558 B2 * | 5/2010 | Ott | 604/26 |
| 2005/0137529 A1 | 6/2005 | Mantell | |
| 2005/0288551 A1 * | 12/2005 | Callister et al. | 600/115 |
| 2006/0129087 A1 | 6/2006 | Uesugi et al. | |
| 2007/0088275 A1 | 4/2007 | Stearns et al. | |
| 2009/0278064 A1 | 11/2009 | Grenaway et al. | |

\* cited by examiner

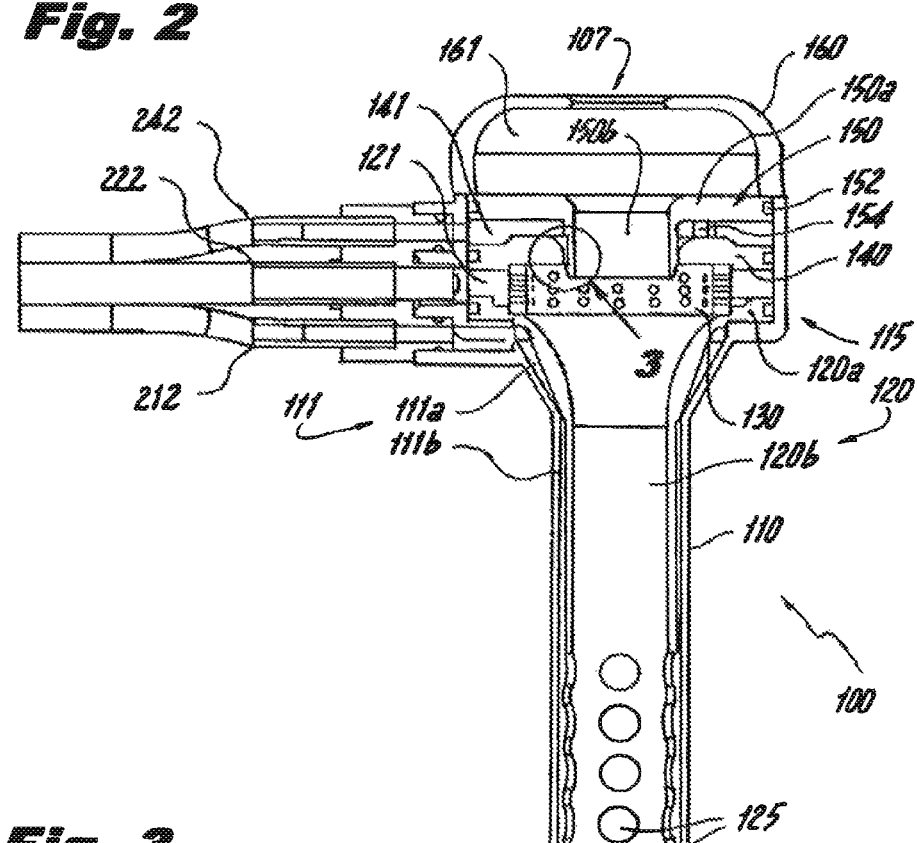
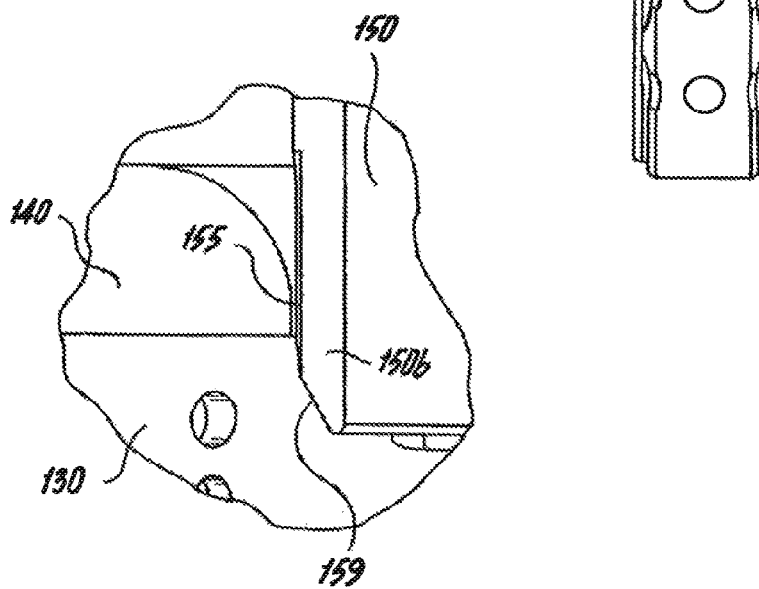

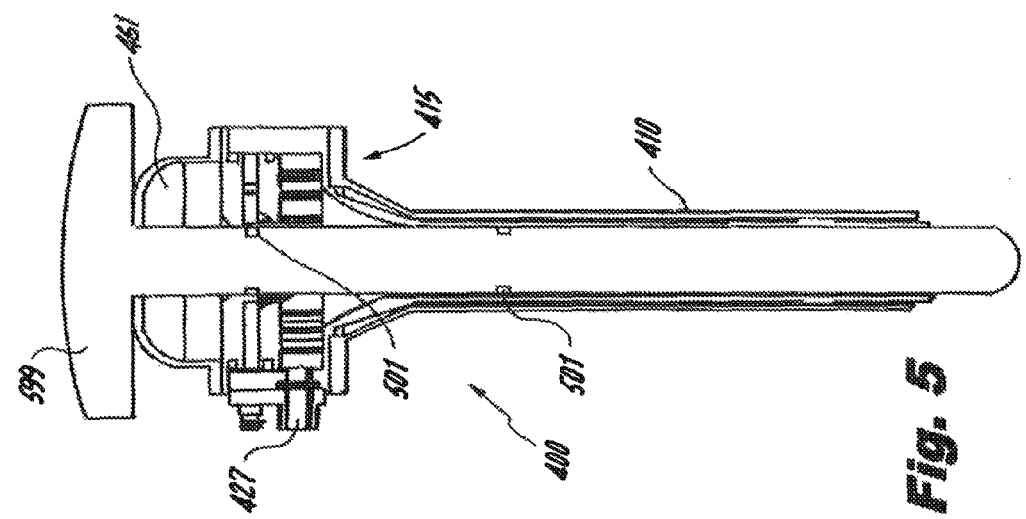
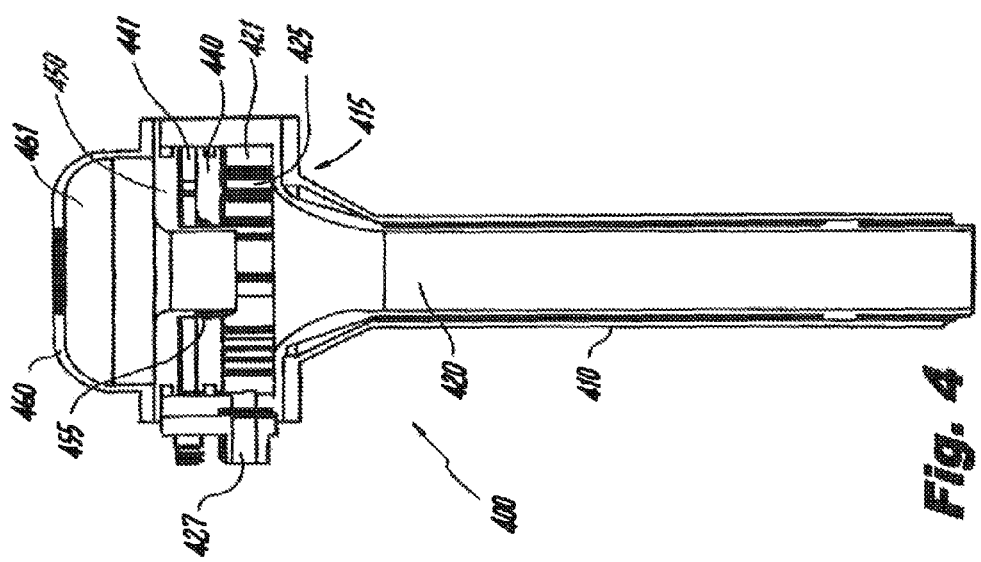

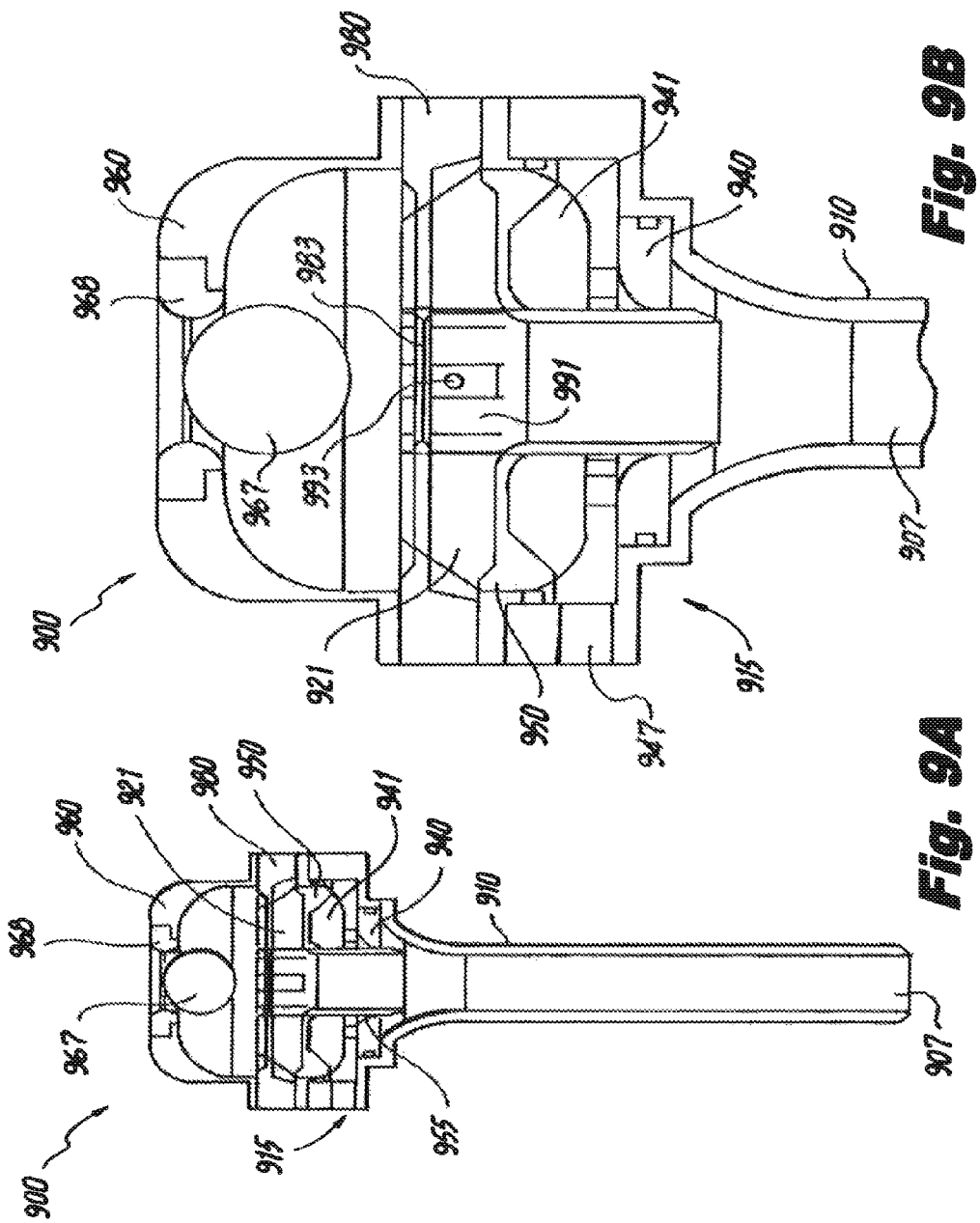

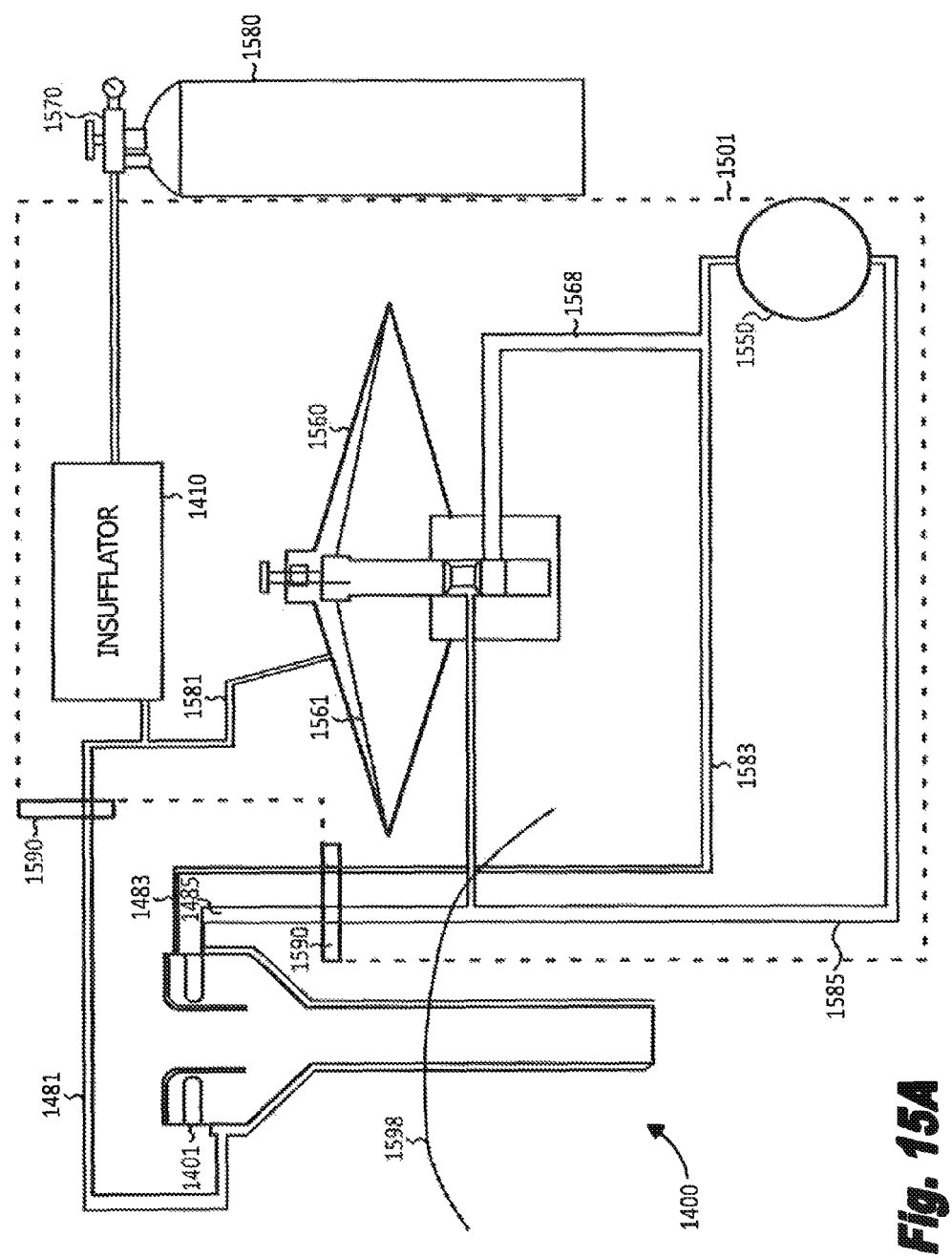

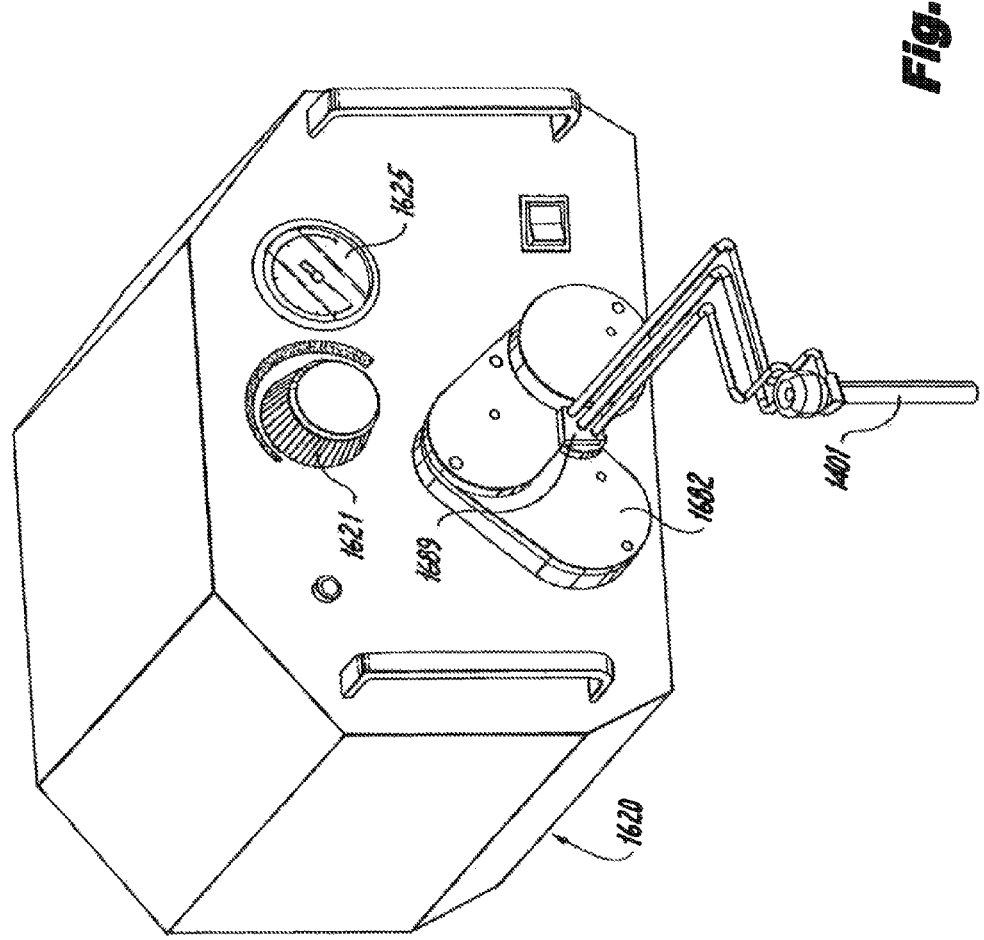

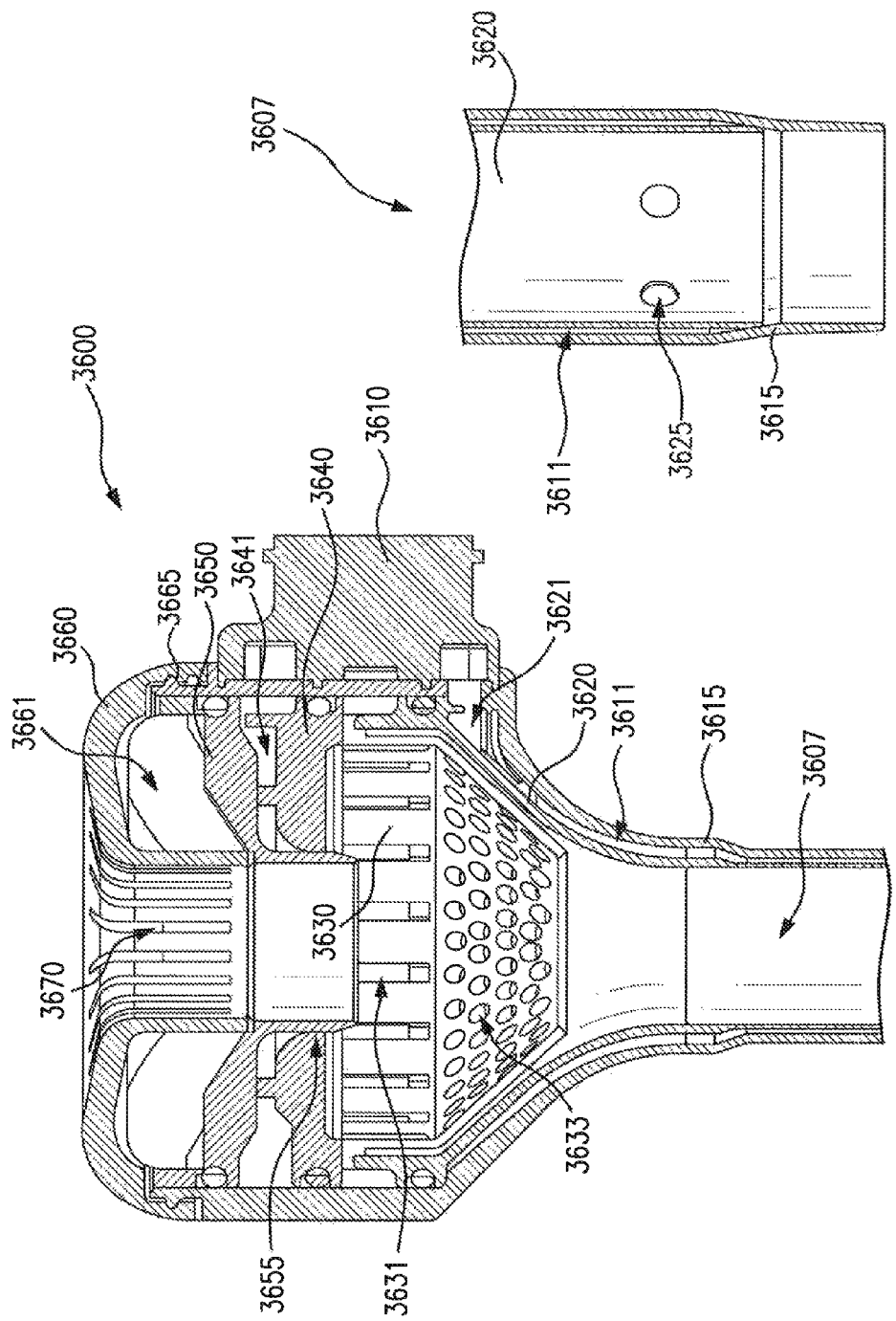

SYSTEM AND METHOD FOR IMPROVED GAS RECIRCULATION IN SURGICAL TROCARS WITH PNEUMATIC SEALING

CROSS-REFERENCE TO RELATED APPLICATIONS

This application is a continuation of U.S. patent application Ser. No. 14/268,408 filed on May 2, 2014, which claims the benefit of and priority to U.S. patent application Ser. No. 12/587,584 filed Oct. 9, 2009, which claims the benefit of and priority to U.S. Patent Application Ser. No. 61/104,448, filed Oct. 10, 2008. This application is also related to U.S. patent application Ser. No. 11/960,701, filed Dec. 20, 2007 (U.S. Pub. No. 2009/0137943), which is a continuation of PCT application PCT/US07/88017 filed Dec. 18, 2007 (PCT Pub. No. WO2008/077080), which claims the benefit of priority to each of U.S. Provisional Application No. 60/875,436 filed Dec. 18, 2006, U.S. Provisional Application No. 60/923,917 filed Apr. 17, 2007, and U.S. Provisional Application No. 60/959,826 filed Jul. 16, 2007. This application is also related to U.S. patent application Ser. No. 11/786,832 filed Apr. 13, 2007 (U.S. Pub. No. 2008/0086080), Ser. No. 11/544,856 filed Oct. 6, 2006 (U.S. Pub. No. 2008/0086167), Ser. No. 11/517,929, filed Sep. 8, 2006 (U.S. Pub. No. 2007/0088275), and U.S. Pat. Nos. 7,338,473, 7,285,112 and 7,182,752. Each of the foregoing applications and patents is incorporated herein by reference in its entirety.

BACKGROUND OF THE INVENTION

1. Field of the Invention

The present application relates to systems and devices for surgical access, and is particularly directed devices adapted and configured to create a fluidic seal, and to systems for supplying pressurized fluid to such devices, which are also capable of recirculating such pressurized fluid. Surgical access devices configured for creating a fluidic seal for surgical access are set forth in the following applications, which are incorporated herein by reference in their entirety: U.S. patent application Ser. No. 11/517,929, filed Sep. 8, 2006, U.S. Pat. No. 7,338,473, U.S. Pat. No. 7,285,112, U.S. Pat. No. 7,182,752.

2. Description of Related Art

Laparoscopic, or "minimally invasive" surgical techniques are becoming increasingly more common. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the trocar devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar. However, sealing in this manner is not usually complete, such seals cannot seal between multiple instruments, and such seals also inhibit free movement of the surgical instruments and/or removal of tissue through the trocar. Such seals are also vulnerable to damage during the surgical procedure. Alternatively, a flapper valve or spring-loaded trap door can be used. However, these types of mechanical valves suffer from similar drawbacks.

Most valves, and particularly duckbill-type valves, which include resilient valve members that directly contact surgical instruments, not only interfere with the movement of surgical instruments, but reduce the ability of a surgeon to accurately sense the patient anatomy on which the surgeon is operating. Minimally invasive surgical procedures are carried out with a visualization aid such as a camera, and as a result, depth perception on the part of the surgeon is inhibited. Moreover, when the endoscope passes through mechanical seals, lenses thereof can be dirtied, typically with smears appearing, resulting in further vision difficulty. The absence of mechanical seals also allows swabs and specimens to be extracted without excessive interference. Additionally, the ability to physically sense resistance of structures and of tissues through movement of the surgical instruments plays an important role in a successful and safe surgical procedure. Frictional forces imparted on surgical instruments by contact of the aforementioned mechanical valves can mask the sensory signals, i.e., the haptic perception, that the surgeon might otherwise use to determine precisely what is occurring at the opposite end of the surgical instruments being used. Additionally, conventional surgeries typically involve the use of cautery and suction devices, each of which presents disadvantages, particularly when used in minimally invasive procedures under insufflation, where a patient's body cavity becomes, essentially, a closed, pressurized space. Accordingly, smoke created by cautery devices and the like fill the closed space with particulates that inhibit the surgeon's view of the operative site. Although devices, to evacuate smoke from a surgical site have been developed, there are disadvantages to such systems, including that one or two additional incisions must be made to access the respective body cavity of the patient.

Additionally the use of suction devices, such as those used to remove liquids at the operative site, disturb the pressure balance in the patient's body cavity, undesirably remove the carbon dioxide gas used for insufflation, and at the same time cause external air (from the operating room) to be drawn into the surgical site, altering the concentration of carbon dioxide gas to other gasses in the body cavity, which is typically undesirable for the safety of the patient.

Accordingly, improvements to sealing technologies that allow unencumbered access while maintaining a pneumoperitoneum, are desired. The present invention provides a solution for these problems.

SUMMARY OF THE INVENTION

The purpose and advantages of the present invention will be set forth in and apparent from the description that follows. Additional advantages of the invention will be realized and attained by the devices, systems and methods particularly pointed out in the written description and claims hereof, as well as from the appended drawings.

To achieve these and other advantages and in accordance with the purpose of the invention, as embodied, the invention includes, in one embodiment, a system for insufflation and recirculation of insufflation fluid from a surgical operative environment, such as a patient's abdominal cavity. The system includes a control unit having a fluid pump, a supply conduit, a return fluid conduit and a pressure-controlled valve. The fluid pump is adapted and configured to circulate insufflation fluid through the system. The supply conduit is in fluid communication with an output of the fluid pump and configured and adapted for delivering pressurized insufflation fluid to an output port of the control unit. The return conduit is in fluid communication with an input of the fluid pump for delivering insufflation fluid to the fluid pump and is configured and adapted for returning insufflation fluid from an input port of the control unit. The pressure-controlled valve is in fluid communication with the supply conduit and the return conduit, and is adapted and configured to receive a control signal and respond to the control signal by adjusting as follows.

The pressure-controlled valve responds to a low pressure control signal by opening, to place the supply conduit and the return conduit in fluid communication with one another, to reduce entrainment of air from the surrounding environment and to place the insufflation gas supply in fluid communication with the return conduit to increase the concentration of insufflation gas in the system.

The pressure-controlled valve responds to a first high pressure control signal by opening, placing the supply conduit and the return conduit in fluid communication with one another.

The pressure-controlled valve responds to a second high pressure control signal, corresponding to a pressure higher than the first high pressure control signal, by additionally opening a dump valve to release pressure from the system.

In absence of a control signal, the pressure-controlled valve can be configured to remain in a closed state. The pressure-controlled valve can be additionally in fluid communication with a pressure sensing conduit, adapted and configured for communicating a control signal, corresponding to a pressure value at a distal end thereof, to the pressure-controlled valve.

In accordance with one aspect of the invention, a low pressure, causing a low pressure control signal, can be defined as an abdominal pressure at or below about 4.0 mmHg from a set pressure, a first high pressure, causing a first high pressure control signal, can be defined as an abdominal pressure at or above 4.0 mmHg from the set pressure, and a second high pressure, higher than the first high pressure, causing a second high pressure control signal, can be defined as an abdominal pressure at or above about 160% of the set pressure.

The pressure-controlled valve can be a mechanical diaphragm valve, with the pressure sensing conduit in fluid communication with a pressure sensing chamber of the pressure-controlled valve. Alternatively, pressure sensing can be accomplished by way of an electronic pressure transducer electrically coupled to an electromechanical valve.

The system can further include a trocar having an elongated body defining a lumen therein, a nozzle operatively associated with the body for directing pressurized fluid into the lumen, and a fluid return plenum adapted and configured to collect spent insufflation fluid. A nozzle supply port is in fluid communication with the nozzle, for delivering a pressurized flow of insufflation fluid to the nozzle, and adapted and configured to receive pressurized insufflation fluid from an output port of the control unit. A fluid return port is in fluid communication with the fluid return plenum, and is adapted and configured for returning insufflation fluid from the trocar to an input port of the control unit. The trocar can further include a pressure sensing chamber adapted and configured to be in fluid communication with a patient's abdominal cavity and with the pressure-controlled valve of the control unit.

Systems in accordance with the invention can further include a connection kit having a plurality of connecting conduits, one or more filters, and one or more connectors. The plurality of connecting conduits are adapted and configured to connect the nozzle supply port of the trocar to the output port of the control unit, to connect the fluid return port of the trocar to the input port of the control unit, and to connect the pressure sensing chamber of the trocar to the pressure-controlled valve of the control unit. The filter element is provided in fluid communication with at least one of the connecting conduits. The one or more connectors are disposed at each end of the connecting conduits, and are configured and adapted to mutually engage the connection kit with the trocar at one end, and with the control unit at its opposite end.

The system can include a surgical insufflator adapted and configured to receive, through an input port thereof, a supply of insufflation gas from a source, an output port of the insufflator being in fluid communication with a pressure sensor for operating the pressure-controlled valve and with a patient's abdominal cavity, the insufflator being adapted and configured to sense pressure within the abdominal cavity and to provide insufflation fluid thereto.

The control unit can include the surgical insufflator incorporated into a single housing. Moreover, systems in accordance with the invention can further include first and second trocars. The first trocar can include an elongated body defining a lumen therein, a nozzle operatively associated with the body for directing pressurized fluid into the lumen to form a fluid seal thereacross, a fluid return plenum adapted and configured to collect spent insufflation fluid, a nozzle supply port in fluid communication with the nozzle, for delivering a pressurized flow of insufflation fluid to the nozzle, adapted and configured to receive pressurized insufflation fluid from an output port of the control unit, and a fluid return port in fluid communication with the fluid return plenum, adapted and configured for returning insufflation fluid from the trocar to an input port of the control unit. The second trocar can be in fluid communication with a surgical insufflator adapted and configured to receive, through an input port thereof, a supply of insufflation gas from a source, the insufflator being adapted and configured to sense pressure within an abdominal cavity and to deliver pressurized insufflation fluid thereto through the second trocar. The second trocar can be used as a primary trocar for insufflation of the abdomen prior to activation of the first trocar, or vice versa, as desired.

In accordance with the invention, the insufflator and the pressure-controlled valve can each be independently in fluid communication with a patient's abdominal cavity, and each are adapted and configured to sense abdominal pressure therein.

In accordance with a further aspect of the invention a trocar for use in a minimally-invasive surgical procedure is provided. The trocar includes an elongated body, a fluid supply plenum, a supply port, a nozzle and a fluid return port. The body defines a lumen therein, the proximal end portion of the body defining a housing, and a fluid supply plenum is defined in the housing. The supply port is in fluid communication with the fluid supply plenum, and is adapted and configured to receive pressurized insufflation fluid from a recirculation device and to deliver the pressurized insufflation fluid to the fluid supply plenum. The nozzle is in fluid communication with the fluid supply plenum and the lumen, and is configured and adapted for directing pressurized fluid into the lumen. The fluid return plenum is defined in the housing and arranged distal the fluid supply plenum. The fluid return plenum is adapted and configured to collect spent insufflation fluid. The fluid return port is in fluid communication with the fluid return plenum, and is adapted and configured for returning insufflation fluid from the trocar to a recirculation device.

The trocar can further include sound attenuation elements arranged in the fluid return plenum. The sound attenuation elements can be selected from the group consisting essentially of baffles and sound-absorbing material, such as foam, for example. The trocar can further include sound attenuation elements arranged in a proximal sound attenuation chamber arranged proximal to the fluid supply plenum.

In accordance with the invention, the fluid return plenum can be defined between a distal end of the housing and a first substantially annular insert placed in the housing, and the fluid supply plenum can be defined between the annular insert and a second substantially annular insert. The second substantially annular insert can have a substantially tubular member extending distally therefrom, with the nozzle being defined between the substantially tubular member and an central portion of the first substantially annular insert.

The trocar can further include a pressure sensing chamber adapted and configured to be placed in fluid communication with a patient's abdominal cavity. The pressure sensing chamber can be in fluid communication with a pressure sensing port defined on the trocar, for connecting to a pressure sensing element, such as a diaphragm or electronic pressure transducer, for example.

In accordance with another embodiment of the invention, a trocar for use in a minimally-invasive surgical procedure includes an elongated body and first, second, third and fourth inserts. The proximal end portion of the body defines a housing. The first insert has a substantially tubular configuration extending through the body and defining a pressure sensing chamber therebetween. The pressure sensing chamber is adapted and configured to be placed in fluid communication with a patient's abdominal cavity. The second insert is arranged in the housing proximal the first insert, and has a substantially annular configuration and a plurality of apertures defined therein for allowing passage of spent insufflation fluid to pass therethrough. The third insert is arranged in the housing proximal the second insert, and has a substantially annular configuration. The housing, first, second and third inserts define respective walls of a fluid return plenum, which is adapted and configured to collect spent insufflation fluid. The fourth insert is arranged in the housing proximal the third insert, and has a substantially annular configuration and substantially tubular member extending distally therefrom. A nozzle defined between the substantially tubular member and a central portion of the third insert. The housing and third and fourth inserts define a fluid supply plenum in fluid communication with the nozzle.

The trocar can further include sound attenuation elements arranged in a proximal sound attenuation chamber arranged proximal to the fluid supply plenum. The first insert can include at least one aperture defined in the sidewall thereof to attenuate a sound created by airflow through the first insert.

In accordance with still another embodiment of the invention, a trocar for use in a minimally-invasive surgical procedure is provided. The trocar has an elongated body, a fluid return plenum, and a fluid supply plenum. The body has a lumen extending therethrough, with the proximal end portion of the body defining a housing. The fluid return plenum is defined in the housing and is adapted and configured to collect spent insufflation fluid. The fluid supply plenum is defined in the housing and arranged proximal the fluid return plenum. The fluid supply plenum is adapted and configured to deliver pressurized insufflation fluid to a nozzle in fluid communication therewith. The nozzle is configured and adapted for directing pressurized fluid into the lumen.

In accordance with this embodiment or other embodiments set forth herein, the trocar can further include a pressure sensing chamber defined in a distal end portion of the housing, distal the fluid return plenum, adapted and configured to be placed in fluid communication with a patient's abdominal cavity.

In accordance with still another embodiment of the invention, a trocar for use in a minimally-invasive surgical procedure is provided having an elongated body, a pressure sensing chamber, a safety valve and a fluid supply plenum. The elongated body has a lumen extending therethrough, and the proximal end portion of the body defines a housing. The pressure sensing chamber is defined in a distal end portion of the housing, and is adapted and configured to be placed in fluid communication with a patient's abdominal cavity. The safety valve is arranged in the housing, is in fluid communication with the pressure sensing chamber and configured and is adapted to relieve pressure from within a patient's abdominal cavity in a case of abdominal pressure exceeding a predetermined limit. The fluid supply plenum is defined in the housing, arranged proximal the fluid return plenum, and is adapted and configured to deliver pressurized insufflation fluid to a nozzle in fluid communication therewith. The nozzle is configured and adapted for directing pressurized fluid into the lumen.

If desired, a pressure relief valve in direct fluid communication to the outside of the trocar, and the surrounding environment, can also be in communication with the return plenum. Such a pressure relief valve prevents outside air from being sucked into the plenum but allows overpressure fluid to escape, harmlessly.

In accordance with the invention, a method of sealing a pressurized cavity of a patient for a surgical procedure is provided. The method includes the steps of providing a trocar for use in a minimally invasive surgical procedure, supplying a flow of pressurized fluid to the fluid supply plenum, recovering a flow of spent insufflation fluid from the fluid return plenum, recycling at least a portion of the spent insufflation fluid received from the return plenum to the fluid supply plenum, inserting a surgical instrument through the lumen of the trocar, whereby the pressurized fluid supplied to the fluid supply plenum forms a pressure barrier around the surgical instrument, thereby inhibiting loss of pressure within the cavity of the patient. In accordance with this method, the trocar includes an elongated body, a fluid return plenum and a fluid supply plenum. The elongated body has a lumen extending therethrough, and the proximal end portion of the body defines a housing. The fluid return plenum is defined in the housing, and is adapted and configured to collect spent insufflation fluid. The fluid supply plenum is defined in the housing, is arranged proximal the fluid return plenum, and is adapted and configured to deliver pressurized insufflation fluid to a nozzle in fluid communication therewith. The nozzle is configured and adapted for directing pressurized fluid into the lumen. The method can further include the step of filtering the insufflation gas during the step of recycling. Additionally, the step of inserting a second surgical instrument through the lumen of the trocar, whereby the pressurized fluid supplied to the trocar seals around and between the first and second surgical instruments, preventing loss of pressure within the cavity of the patient can be included.

In accordance with another embodiment of the invention, a surgical access device is provided having an elongated outer tubular member with opposed proximal and distal portions and having a longitudinal axis extending therethrough. An elongated inner tubular member having opposed proximal and distal end portions is arranged coaxially within the outer tubular member. An insufflation conduit is defined between the inner and outer tubular members in communication with a source of humidified insufflation gas. A plurality of apertures is provided on an outer surface of the distal portion of the outer tubular member in fluid communication with the insufflation conduit and configured to discharge humidified insufflation gas from the insufflation conduit into the peritoneum of a patient.

The insufflation conduit may extend from a housing at the proximal portion of the trocar. The housing is in communication with a supply conduit to facilitate supply of the humidified insufflation gas to the insufflation conduit. The source of humidified insufflation gas may be external to the trocar.

In accordance with yet another embodiment, a system for delivering humidified insufflation gas is disclosed. The system includes a trocar assembly having an elongated outer tubular member having opposed proximal and distal end portions. A longitudinal axis extends through the outer tubular member. An elongated inner tubular member having opposed proximal and distal end portions is arranged coaxially within the outer tubular member so as to form an insufflation conduit therebetween. The insufflation conduit extends from the proximal end portion of the outer tubular member to the distal end portion of the outer tubular member. The insufflation conduit is in fluid communication with a plurality of apertures provided on the outer surface of the distal portion of the outer tubular member. A source of humidified insufflation gas is in fluid communication with the insufflation conduit to discharge humidified insufflation gas from the plurality of apertures into the peritoneum of a patient.

In accordance with yet another embodiment of the invention, a surgical access device is disclosed. The device includes an elongated outer tubular member having opposed proximal and distal portions and having a longitudinal axis extending therethrough. An elongated inner tubular member having opposed proximal and distal end portion and is arranged coaxially within the outer tubular member. An insufflation conduit is defined between the inner and outer tubular members in communication with a source of conditioned insufflation gas. A plurality of apertures provided on an outer surface of the distal portion of the outer tubular member is in fluid communication with the insufflation conduit and is configured to discharge conditioned insufflation gas from the insufflation conduit into the peritoneum of a patient. 24. The conditioned insufflation gas may be humidified insufflation gas. The conditioned insufflation gas may also be heated insufflation gas.

It is noted that although the term "trocar" is used herein, the term is intended to mean a surgical access device, that allows insertion of surgical instruments, a surgeon's hand or the like, into a surgical cavity, while maintaining insufflation pressure.

It is to be understood that any feature described in connection with any particular embodiment set forth herein can advantageously be applied to other embodiments set forth herein, or indeed, to variations of embodiments not specifically set forth herein, and still be in keeping with the spirit of the present invention. It is also to be understood that both the foregoing general description and the following detailed description are exemplary and are intended to provide further explanation of the invention claimed.

BRIEF DESCRIPTION OF THE DRAWINGS

So that those having ordinary skill in the art to which the subject invention pertains will more readily understand how to make and use the devices and systems of the subject invention, preferred embodiments thereof will be described in detail hereinbelow, with reference to the drawings, wherein:

FIG. 2 is a cross-sectional view of the trocar of FIG. 1.

FIG. 3 is an enlarged view of the respective portion of FIG. 2, illustrating the nozzle in detail;

FIG. 4 is a cross-sectional view of a trocar in accordance with a further embodiment the present invention;

FIG. 5 is a cross-sectional view of the trocar of FIG. 4 with an obturator inserted therethrough;

FIG. 9A is a cross-sectional view of a trocar in accordance with a further embodiment the present invention, having a proximal ball valve and a proximally arranged fluid collection chamber;

FIG. 9B is an enlarged partial cross-sectional view of the trocar of FIG. 9A, illustrating detail in the proximal end portion thereof;

FIG. 15A is an example schematic representation of the main components included within the system of FIG. 14;

FIG. 16 is an alternate embodiment of the system of FIGS. 14 and 15, wherein main components of the system are housed in a single unit;

FIG. 44 is an enlarged cross-sectional view of the proximal end of the surgical access device of FIG. 36;

FIG. 45 is an enlarged cross-sectional view of the distal end of the surgical access device of FIG. 36;

DETAILED DESCRIPTION OF THE PREFERRED EMBODIMENT

The devices, systems and methods presented herein may be used for creating and maintaining a surgical pathway through the abdominal wall of a patient undergoing minimally invasive surgery. The present invention is particularly suited for minimally invasive surgeries performed under insufflation, such as laparoscopic removal of a gall bladder.

Figure 1:
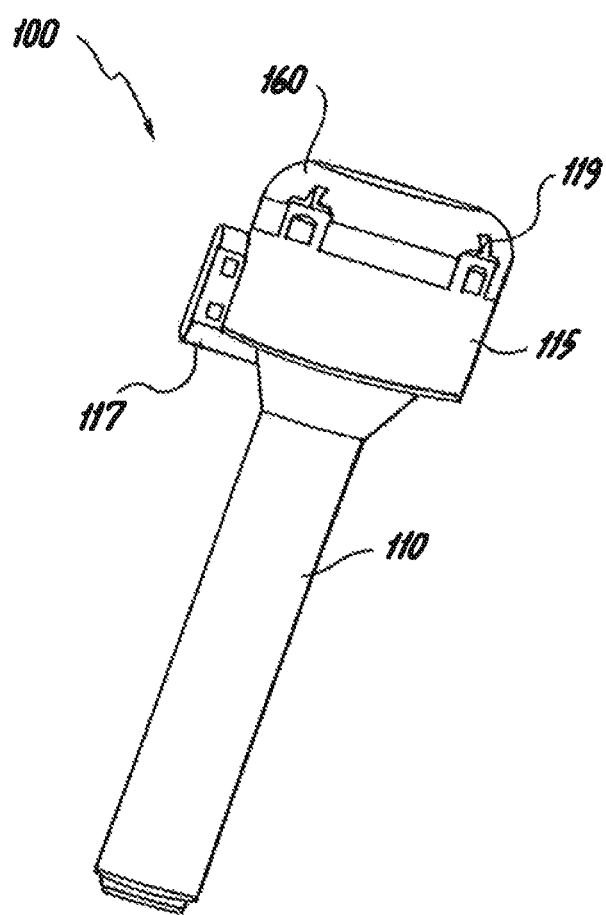
FIG. 1 is an isometric view of a trocar in accordance with one embodiment of the present invention.

For the purposes of explanation and illustration, and not limitation, referring now to the drawings, wherein like reference numerals identify similar structural aspects of the subject trocars and systems therefor, a first exemplary embodiment of a trocar in accordance with the invention is shown in FIGS. 1-3, and is designated generally by reference character 100. Other embodiments of trocars in accordance with the invention, related systems or aspects thereof, are provided in subsequent figures, which are described in detail below.

FIG. 1 is a side view, and FIG. 2 is cross-sectional view of a trocar 100 constructed in accordance with the invention. The trocar includes a central lumen 107, which is defined by various elements, and which extends longitudinally, through the center of the trocar 100. The trocar 100 includes a body 110, including a housing 115 defined in the proximal end portion thereof. A connection block 117 extends from the housing 115 and facilitates connection between the trocar 100 and fluid conduits connected thereto, as best shown in FIG. 2.

Defined within the housing 115 are a pressure sensing chamber 111 including a pressure sensing plenum 111a, which is in fluid communication with a pressure sensing channel 111b. The pressure sensing chamber 111 is defined between the body 110 and a body insert 120, including a substantially tubular portion 120b and a substantially annular portion 120a. This arrangement of the pressure sensing chamber allows the remainder of the system, described hereinbelow, to be in fluid communication with the abdominal cavity, so that the abdominal pressure can be monitored and controlled. As shown in FIG. 2, a pressure sensing conduit 212 is in fluid communication with the pressure sensing chamber 111, which in-turn connects with a control unit of the system, described in more detail hereinbelow. Further, apertures 125 can be formed in the wall of the tubular portion 120b of the body insert 120. These apertures 125 can be arranged so as to alter the acoustic properties of the tubular portion 120b, by reducing the effective length of the tubular portion 120b. Accordingly, the wavelength of sound produced by fluid passing through the lumen 107 can be adjusted so that it is more easily canceled out by other sound attenuation elements, such as those housed within the cap 160.

The annular portion 120a of the body insert 120 separates the pressure sensing chamber 111 and a fluid return plenum 121. The fluid return plenum is further defined by the housing 115 on its outer periphery, a second diffuser insert 130 on its inner periphery, and an annular insert 140 having a substantially annular configuration. The second diffuser insert 130 serves in-part, to maintain spacing between the body insert 120 and the annular insert 140. The fluid return plenum 121 allows for collection of spent insufflation fluid—fluid moving proximally, returning from within the lumen of the tubular portion 120b of the body insert 120. Apertures defined in the second insert promote even evacuation of fluid from about the circumference of the lumen 107 in the region of the fluid return plenum 121. Fluid is removed from the fluid return plenum 121 through a fluid return conduit 222 and can be recirculated, such as through the systems embodied in FIGS. 14-18.

The fourth insert 150 includes a substantially annular portion 150a and a substantially tubular portion 150b. One or more standoffs 154 can be provided on the fourth insert 15, or alternatively the annular insert 140, to maintain spacing of the fluid supply plenum 141 defined therebetween. Additionally, a nozzle 155 is defined between the annular insert 140 and a fourth insert 150. The precise geometry of the annular insert 140 and fourth insert 150, and the spacing therebetween allow for a continuous stream of fluid which serves to effectively seal the lumen 107, and inhibit escape of insufflation fluid. The lower outer circumferential edge 159 of the tubular portion 150b of the fourth insert 150 is angled inward, which directs the continuous stream of fluid centrally. The fluid follows the contour of this surface 159, and is thus directed centrally, at least in part due to the Coanda effect. Fluid is supplied to the fluid supply plenum 141 through a fluid supply conduit 242. Preferably, the fluid return conduit 222 is larger in diameter than the fluid supply conduit 242, as returning fluid is depressurized and therefore occupies an increased volume. To maintain equivalent mass flow rates for supplied and returned fluid, the diameter of the fluid return conduit 222 should have a larger diameter. Pressurized insufflation fluid can be supplied to the trocar 1000 through systems such as those embodied in FIGS. 14-18.

Additionally, any of the inserts can be sealed to the housing 115 to create fluid-tight seals therebetween. In the illustrated embodiment, grooves 152 are provided between the body insert 120, annular insert 140 and fourth insert 150 and the housing 115, respectively. In these grooves, a sealing element, such as an O-ring can be placed.

A cap 160 is provided at the proximal end of the trocar 100. As illustrated in FIG. 1, the cap 160 can be affixed to the housing 115 by way of a snap fit arrangement. In this case, protrusions on the cap 160 each engage a pawl 119 on the housing 115. Naturally, any other suitable connection can be used, including but not limited to friction fit, a latch, adhesive, solvent welding, ultrasonic welding, heat welding and mechanical fasteners such as a hook- and loop fastener. Accordingly, the cap 160 can be permanently installed or can be removable from the remainder of the trocar 100. Further, as illustrated, the cap 160 can extend past the joint between the fourth insert 150 and the housing 115, effectively preventing proximal movement of any insert held within the housing 115.

The cavity 161 defined by the cap 160, with the exclusion of the volume necessary in the lumen 107 for passage of surgical implements, can include sound absorbing material and/or baffles to reduce noise emitted from the trocar 100. In combination with the apertures 125 formed in the body insert 120, sound emitted can be reduced significantly by mutually tuning these sound attenuating features.

FIGS. 4 and 5 illustrate a second embodiment of a trocar 400 constructed in accordance with the invention, with FIG. 5 illustrating the trocar 400 having an obturator 599 inserted therein. Distinguishing of this embodiment, as compared with the embodiment of FIGS. 1-3, is the fluid return plenum 421. Instead of providing an annular insert having a plurality of apertures formed therein, a plurality of baffles 425 are provided, which act as a standoff to maintain spacing within the housing 415 of the trocar 400, and can be adapted to enhance noise reduction by absorbing sound. Additionally, sound absorbing material can be laced in the fluid return plenum 421 to further enhance noise reduction.

As with the embodiment of FIGS. 1-3, the embodiment of FIGS. 4 and 5 includes a body insert 420 inserted into the body 410. The baffles 425 are integrally formed with an insert, such as the body insert 420 or annular insert 440, but alternatively can be formed independently and separately inserted in the housing 415. The annular insert 440, in conjunction with a nozzle insert 450, together define the nozzle 455 and define the fluid supply plenum 441. Similarly, the fluid return plenum 421 is defined on the distal side of the annular insert 440, and is in fluid communication with a fluid return port 427. Further, a cap 460 can be provided at the proximal end portion of the trocar 400, and can include sound attenuation materials therein.

As shown in FIG. 5, the obturator 599 has been designed for the recirculation system and devices disclosed herein. The obturator has O-rings 501 proximal and distal to the jets that fit tightly into the cannula. With the obturator 599 installed the O-rings 501 maintain a seal against gas escaping from the abdomen through the trocar 400. The O-rings 501 also contain the jet flow within the trocar 400. The supply can be pumped to the trocar prior to insertion. The gas will pass through the jets and out the return line without creating any blowing effects external to the trocar. Once the trocar 400 is inserted into the patient, the obturator 599 can be removed and the air seal will be established without losing pneumoperitoneum.

Figure 7:
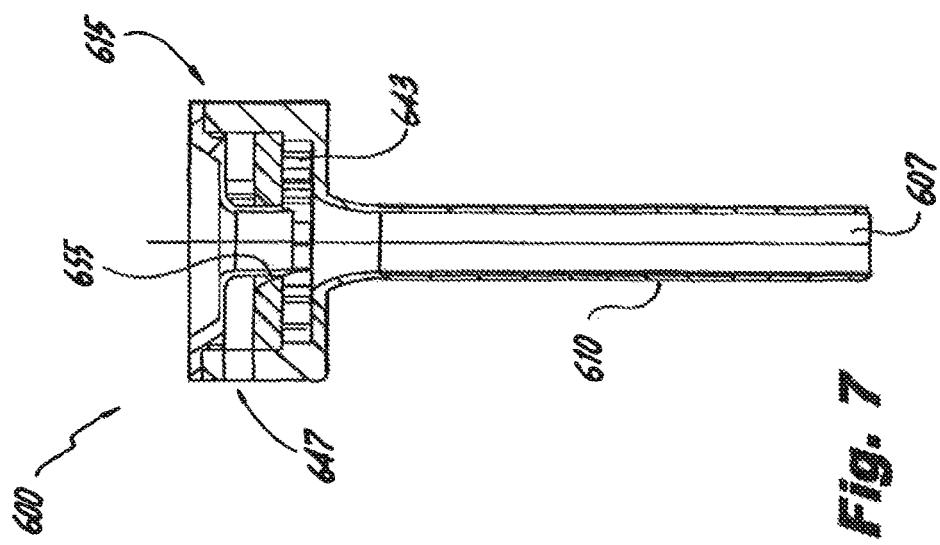
FIG. 7 is a cross-sectional view of the trocar of FIG. 6, rotated about its longitudinal axis.
Figure 6:
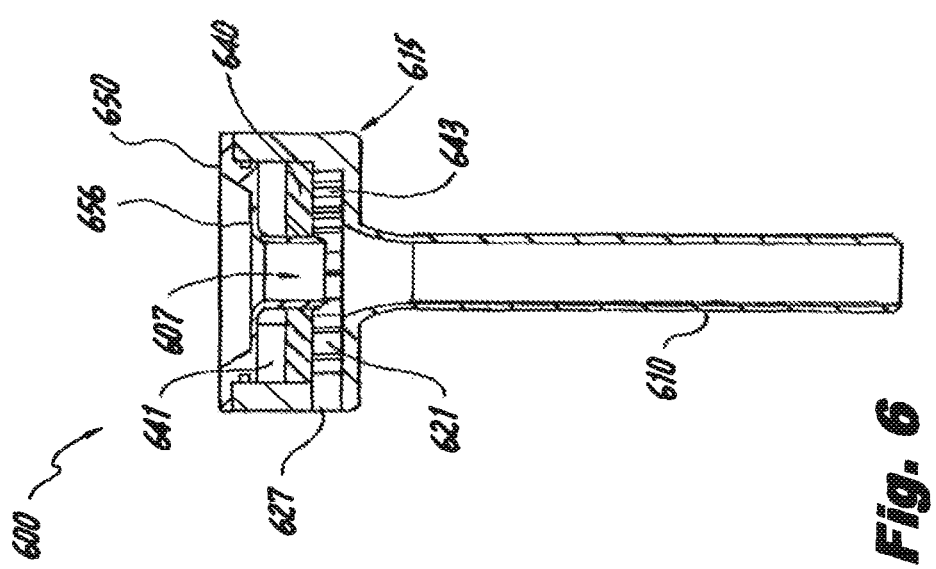
FIG. 6 is a cross-sectional view of a trocar in accordance with still a further embodiment the present invention.

FIGS. 6 and 7 illustrate a third representative embodiment of a trocar 600 in accordance with the invention. The trocar 600 is similar to the foregoing embodiments, but does not include either a pressure sense plenum, or a proximal cap. The trocar 600 includes a body 610, having a housing 615 arranged at the proximal end portion thereof. Baffles 643, an annular insert 640 and nozzle insert 650, respectively define, in conjunction with the housing 615, a fluid return plenum 621, a fluid supply plenum 641, a central lumen 607 and a nozzle 655. The nozzle insert 650 is formed so as to have a depressed region 656 which helps guide surgical instruments to the lumen 607. A return fluid port 627 (FIG. 6) is formed through the housing 615 and is in fluid communication with the fluid return plenum. A fluid supply port 647 (FIG. 7) is similarly formed through the housing 615 and is in fluid communication with the fluid supply plenum 641.

Figure 8A:
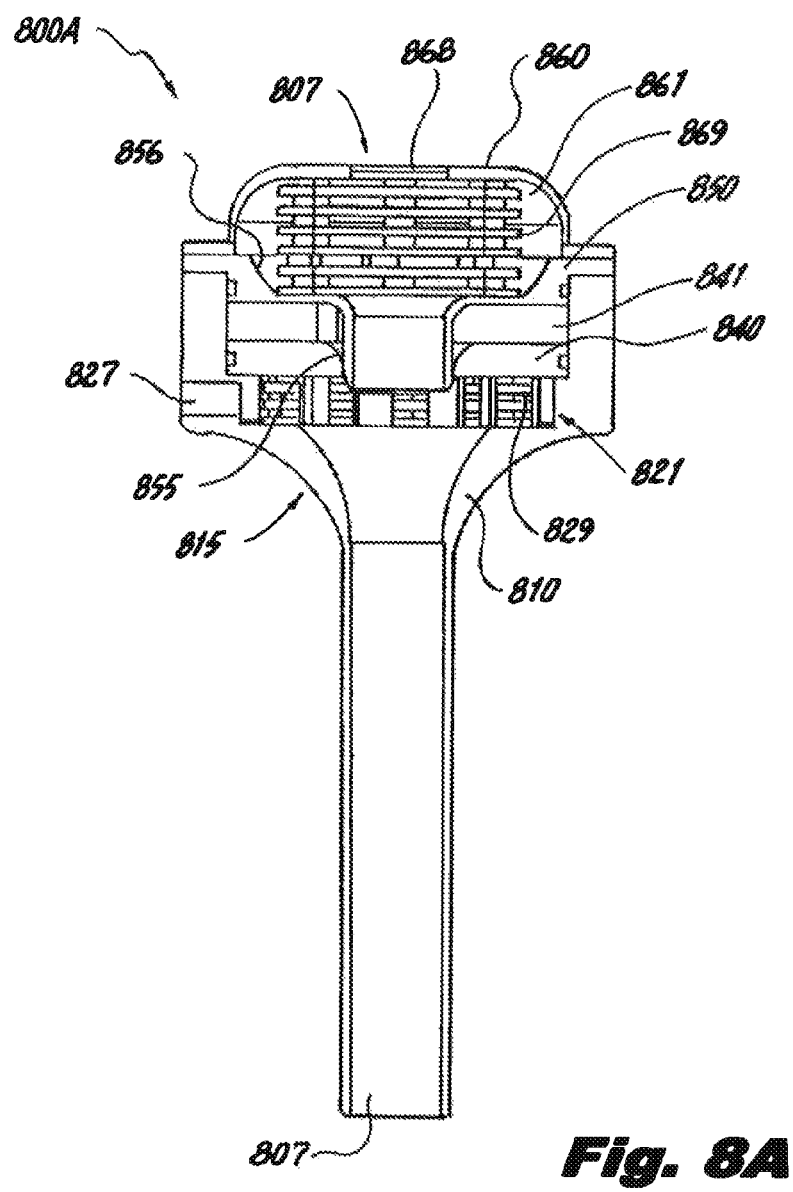
FIG. 8A is a cross-sectional view of a trocar in accordance with still another embodiment the present invention having proximal and distal sound attenuation chambers in the housing thereof.

FIG. 8A illustrates yet another trocar 800A constructed in accordance with the present invention. The trocar 800A includes a body 810, having a housing 815 arranged at the proximal end portion thereof. Distal baffles 829, an annular insert 840 and nozzle insert 850, respectively define, in conjunction with the housing 815, a fluid return plenum 821, a fluid supply plenum 841, a central lumen 807 and a nozzle 855. The nozzle insert 850 is formed so as to have a depressed region 856 which helps accommodate proximal baffles 869 within the chamber 861 defined by a proximal cap 860. A reduced aperture 868 can be provided at the proximal end portion of the cap 860. Optionally, an annular seal can be provided therein in order to further seal the lumen 807 against a surgical instrument when the surgical instrument is inserted therethrough.

A return fluid port 827 is formed through the housing 815 and is in fluid communication with the fluid return plenum 821. A fluid supply port is similarly formed through the housing 815 and is in fluid communication with the fluid supply plenum 841. As with the foregoing embodiment, no pressure sense chamber is provided, but as is the case with the foregoing embodiment or any embodiment set forth herein, such pressure sense capability can be imparted by providing such a chamber in another, similar trocar or as a separately inserted needle into the abdomen of the patient.

Figure 8B:
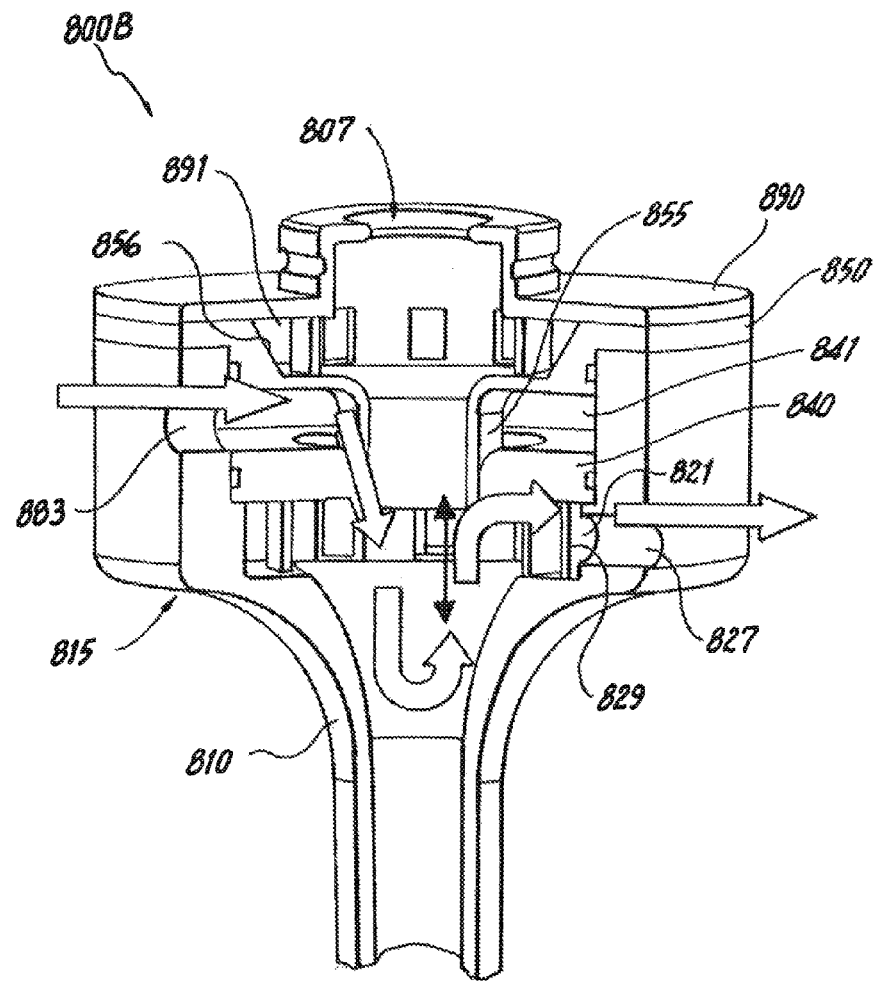
FIG. 8B is a cross-sectional view of a trocar in accordance with still another embodiment the present invention having proximal and distal sound attenuation chambers in the housing thereof, and a proximal adapter portion for engaging a removable cap.

FIG. 8B illustrates a trocar 800B having an alternate arrangement of the proximal end thereof, but otherwise similar to trocar 800A of FIG. 8A. The trocar 800B includes a body 810, having a housing 815 arranged at the proximal end portion thereof. Distal baffles 829, an annular insert 840 and nozzle insert 850, respectively define, in conjunction with the housing 815, a fluid return plenum 821, a fluid supply plenum 841, a central lumen 807 and a nozzle 855. The nozzle insert 850 is formed so as to have a depressed region 856 which helps accommodate a proximal sound attenuation chamber 891, in cooperation with a proximal cap adapter insert 890. Sound absorbing material can be provided in the sound attenuation chamber 891 to help reduce noise emitted by the flowing fluid within the trocar 800B. The cap adapter insert 890 can facilitate engagement between the trocar 800B and a cap, such as one containing a ball valve, for example.

A return fluid port 827 is formed through the housing 815 and is in fluid communication with the fluid return plenum 821. A fluid supply port 883 is similarly formed through the housing 815 and is in fluid communication with the fluid supply plenum 841.

In each of the foregoing embodiments, fluid return plena have been arranged distally, with respect to the fluid supply plena in each trocar embodiment. However, alternatively, the fluid return plenum may be arranged proximally, with respect to the fluid supply plenum. Such an arrangement is illustrated in connection with the trocar 900 illustrated in FIGS. 9A and 9B.

The trocar 900 of FIGS. 9A and 9B includes a body 910, an annular insert 940 and a nozzle insert 950. A nozzle 955 is defined between the annular insert 940 and the nozzle insert 950. A fluid supply plenum 941 is defined in the housing 915 between the annular insert 940 and nozzle insert 950 and is fed by fluid supply port 947. The fluid return plenum 921 is defined proximal the nozzle insert 950, by the nozzle insert 950 and an optional secondary seal element 980, secured to the housing. The secondary seal element 980 is secured to the housing and includes an annular seal 983 to facilitate sealing against instruments inserted through the lumen 907 of the trocar 900. If a complete seal is made between an instrument and the seal element, no fluid can escape through the proximal end of the lumen. Accordingly, if desired, the system that provides insufflation fluid for the purpose of creating a fluid seal in the trocar 900, can be switched off for the duration during which a seal is maintained with the sealing element 980.

Baffles 991 and/or sound absorbent material can be arranged in the fluid return plenum 921 to reduce noise emitted from the trocar 900 when in use. Fluid is exhausted from the fluid return plenum 921 through return fluid port 993. The proximal cap 960 may be permanently or temporarily affixed to the remainder of the trocar 900, and includes a magnetic ball valve, having a ball 967, which engages a ring 968 formed in the cap 960. As embodied, either the ball 967 or the ring 968 can be magnetic, with the other being ferrous. Alternatively, the ring 968 can be embodied as an electromagnet, having power supplied thereto, with the ball 967 being ferrous and therefore attracted to the ring 968 electromagnetic ring when switched on.

Figure 10:
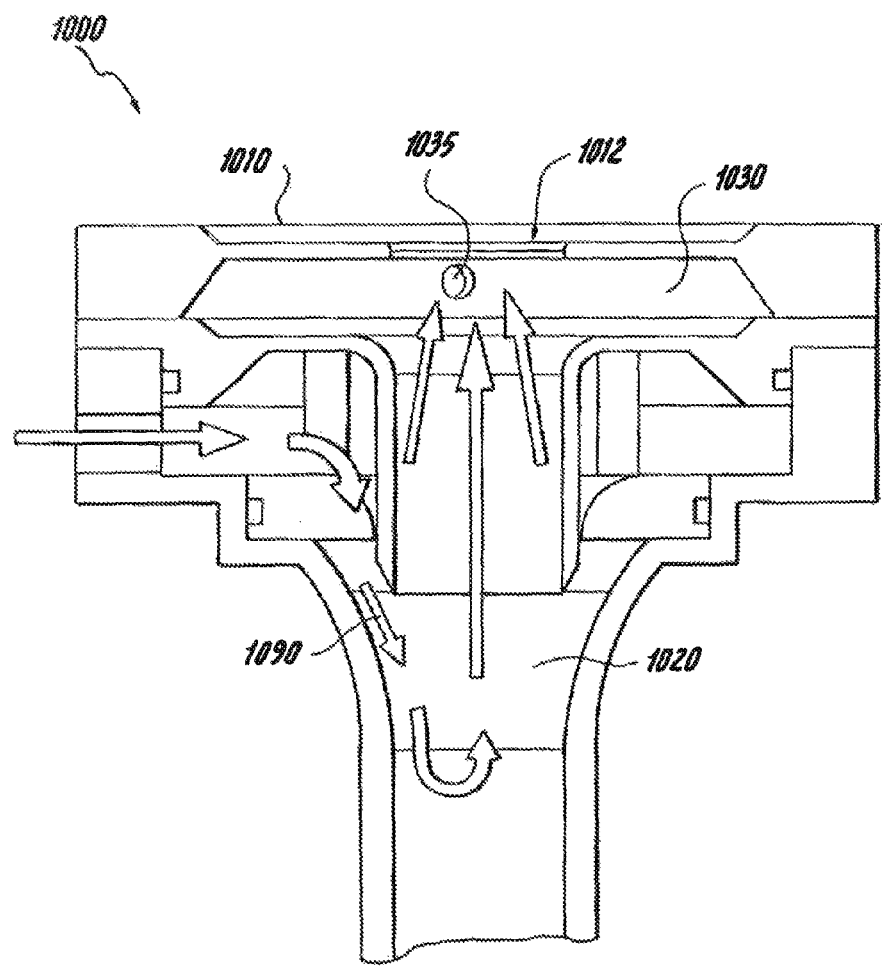
FIG. 10 is a cross-sectional view of a further trocar in accordance with the present invention, having a proximal fluid collection chamber.

Referring to FIG. 10, which illustrates a further embodiment of a trocar 1000 in accordance with the invention, while forming a fluidic seal, the distal motion of the gas is slowed and reversed to an outward flow as it is acted on by pressure within the abdomen. The gas, spent of inward momentum, is pushed proximally, normally through the lumen of the surgical access device. As the spent gas exits the proximal end of the lumen 1020 of the surgical access device 1000, the gas, represented by arrows 1090, will enter a collection chamber 1030 which may also serve to house sound abatement material. The chamber 1030 will be connected to a return line via a port 1035 formed therein, through which a recirculation pump (e.g., pump 1940 of FIG. 19) will extract the exiting gas. During use, supplemental gas (e.g., carbon dioxide) can be added to the system as needed, to insure that the net flow of gas through the proximal end 1010 of the access device 1000 is in the proximal direction. This will ensure that the return flow to the recirculation pump is the desired gas (e.g., carbon dioxide) rather than air drawn into the access device 1000 through the proximal opening 1012. Depending on the precise implementation, a mechanical valve can be provided at the proximal end of the surgical access device. Such a valve can act to further eliminate the potential of drawing external air into the system from the outside.

Figure 11:
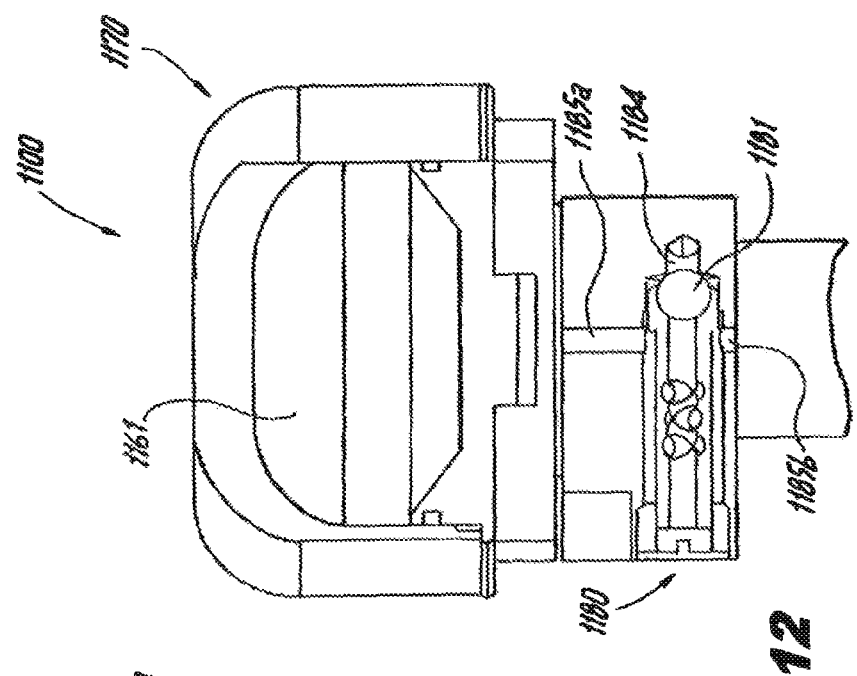
FIG. 11 is a cross-sectional view of a trocar in accordance with a further embodiment the present invention, having a safety valve incorporated therewith and a removable proximal cap.
Figure 12:
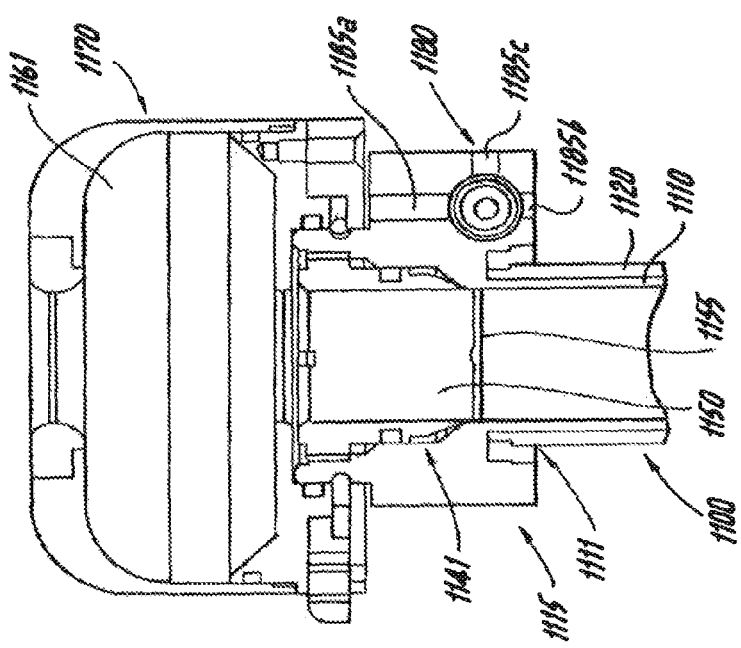
FIG. 12 is an enlarged partial cross-sectional view of the trocar of FIG. 11, illustrating detail in the proximal end portion thereof.

FIGS. 11 and 12 are partial proximal end cross-sectional views of a further embodiment of a trocar 1100 constructed in accordance with the invention. The trocar 1100 includes a body 1110 having a proximal housing 1115. The nozzle 1155 is formed between the housing 1110 and a nozzle insert 1150, between which is also defined a fluid supply plenum 1141. A safety valve 1180 formed in the housing 1115. In this embodiment, a pressure sensing channel and plenum 1111 are formed between the body 1110 and a tubular member 1120 placed over the body 1110.

The safety valve 1180 is configured so as to be urged closed by way of a spring (not shown), but alternate methods of maintaining the valve 1180 closed by maintaining the ball 1181 in contact with a seat are possible. The safety valve 1180 is in fluid communication with the pressure sensing plenum 1111 by way of a fluid conduit 1184. When pressure within the abdominal cavity exceeds a predetermined safe limit, the ball 1181 is urged away from its seat, the spring compressed, and thus the channel 1184 is uncovered. Pressurized fluid then exits exhaust conduits 1185a, 1185b and 1185c. When the pressure in the abdomen subsequently drops, the valve 1180 closes.

The trocar 1100 of FIGS. 11 and 12 includes a cap 1170 removably secured thereto. The cap includes a chamber 1161 defined therein for use with sound attenuation features such as baffles and/or sound absorbing material.

Figure 13:
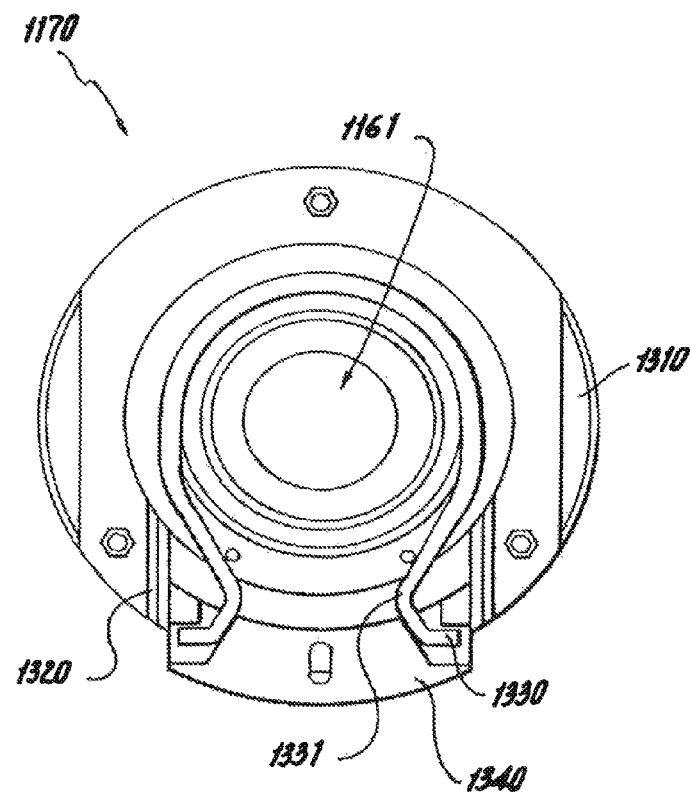
FIG. 13 is a cross-sectional view of the cap of the embodiment of FIGS. 11 and 12.

As shown in FIG. 13, which is a lateral cross-sectional view of the cap 1170 of FIGS. 11 and 12, the body 1310 includes a track 1320, which engages a mating track on the trocar 1100. A resilient locking member 1330 engages a matching groove in the trocar 1100. Depressing the button 1340 causes the locking member 1330 to deflect and open at its neck 1331. This allows insertion onto and removal from the trocar 1100.

In further accordance with the invention, various systems for surgical insufflation and/or for use in creating and maintaining fluid seals in cannulas constructed in accordance with the invention are provided. FIGS. 14-18 illustrate such systems.

Figure 14:
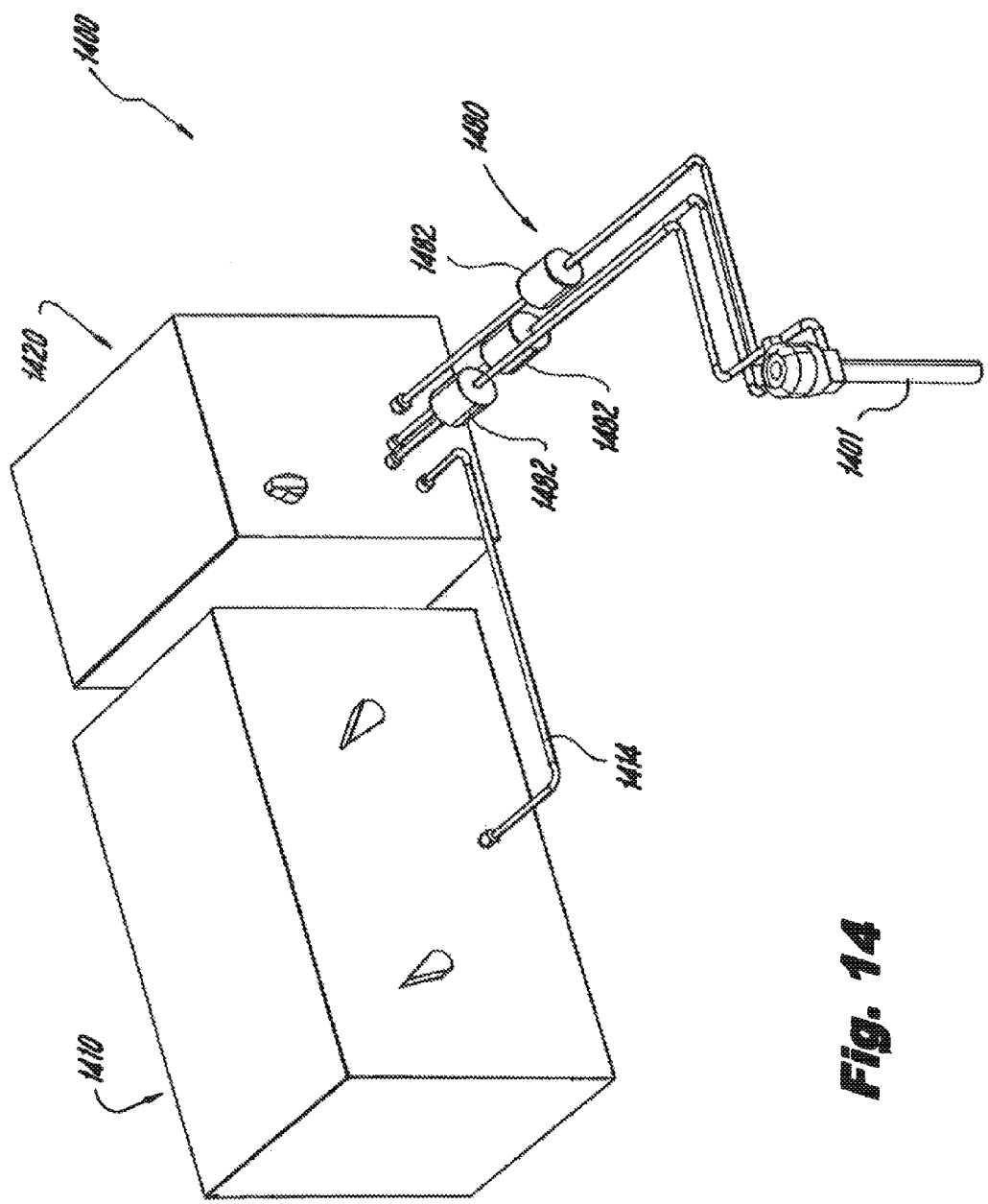
FIG. 14 is an isometric view of one embodiment of an insufflation and circulation system in accordance with the invention.

In the embodiment of FIGS. 14 and 15A, which illustrate a system for surgical insufflation and sealing, a control unit 1420 is shown in connection with a surgical insufflator 1410 and a surgical trocar 1401, in accordance with one system embodiment of the invention. The trocar 1401 is connected to the control unit 1420 by way of fluid conduits 1480, and the insufflator is connected with the control unit 1410 by way of another fluid conduit 1414. As shown in FIG. 15A, the insufflator 1410 receives insufflation fluid from a source, in this case, a tank 1580. A pressure regulator 1570 is provided between the tank 1580 and the insufflator 1410.

The insufflator output is in fluid communication with a pressure sensing line 1481 leading to the trocar 1401, and with a pressure sensing line 1581 leading to a pressure-controlled valve 1560, housed within the control unit 1420. The control unit 1420 also includes a fluid pump 1550 for recirculating insufflation gas for the purpose of maintaining a fluid seal within the trocar 1401, and thus maintain the pneumoperitoneum within the abdomen 1598 of the patient.

The fluid is received from the trocar 1401 through return fluid conduits 1485, 1585, is pressurized by the fluid pump 1550, and is directed through the fluid supply conduits 1583, 1483 to the fluid supply plenum and nozzle of the trocar 1401. If pressure within the abdomen 1598 exceeds a predetermined safe limit, such increased pressure is communicated by way of the pressure sensing conduits 1481, 1581 to the pressure-controlled valve 1560. The pressure-controlled valve 1560 then responds by opening and short circuiting the fluid supply conduit 1583, through bypass conduit 1568, to the fluid return conduit 1585. Thus, fluid that was to be delivered to the trocar 1401 to maintain a fluid seal is reduced, and partially or fully recirculated back to the pump 1550. Accordingly, excess fluid already within the abdomen 1598 will escape until abdominal pressure decreases to an acceptable level, when the valve 1560 closes and fluid flow through the fluid supply conduits 1483, 1583 increases.

In the illustrated embodiment, a diaphragm-type valve, having an internal diaphragm 1561, is shown, but it is to be understood that alternate arrangements of pressure control are applicable to the present invention. For example, a pressure transducer can be arranged in fluid communication with the pneumoperitoneum, by placing the pressure transducer on or in the trocar 1401, or in the control unit 1420, and can be adapted and configured to control an electrically operated valve, for example.

Although illustrated as separate but connected units in FIG. 14, the insufflator 1410 and the control unit 1420 can be contained in a single housing, as indicated by dashed line 1501 in the schematic of FIG. 15A, and as illustrated by element 1620 in FIG. 16. Connectors 1590 allow connections between the control unit 1420 and fluid conduits 1481, 1483, 1485, which in-turn connect to the surgical trocar 1401. Filters are provided in line with the fluid conduits 1480, and can be housed independently as with filters 1482 of FIG. 14, or in a single housing 1682 of FIG. 16.

Insufflation gas is provided to the system 1400 from a supply, such as a tank 1580. The system 1400, which can include elements such as an insufflator 1410, pressure regulator 1570, conditioning elements, such a humidifier, dehumidifier or heater, recirculation pumps and/or other elements, receive the insufflation gas. The system 1400 can further include a safety dump valve in connection with one or more of the fluid conduits to exhaust excess insufflation fluid, if necessary.

Typical surgical insufflators operate by intermittently measuring pressure between periods of insufflation through a single fluid conduit. As embodied in FIGS. 14 and 15, the insufflator 1410 is capable of functioning normally in this regard. The insufflator 1410 can initiate insufflation of the abdomen 1598 through the pressure sensing conduit 1481, and also intermittently measure pressure therethrough. However, normal insufflator operation does not adversely affect the functioning of the pressure-controlled valve 1560. Although slight pressure surges may be caused by the insufflator, a fluid seal in the trocar is maintained.

Accordingly, in operation, when low abdominal pressure is sensed, the insufflator is triggered to insufflate the abdomen 1598, and the pressure-controlled valve 1560 remains in a closed state, with the fluid pump 1550 receiving fluid from a return fluid plenum in the trocar 1401, through the return fluid conduits 1485, 1585, and delivering pressurized fluid through the fluid supply conduits 1583, 1483 to the nozzle of the trocar 1401.

When excessive abdominal pressure is experienced, the insufflator does not provide additional insufflation fluid to the abdomen 1598, and the pressure-controlled valve 1560 opens, connecting the fluid supply conduit 1583 and the return fluid conduit 1585 through the bypass conduit 1568, thereby reducing the effectiveness of a fluid seal formed in the trocar 1401, and allowing a portion of the insufflation fluid to escape, and lowering the pressure within the abdominal cavity.

It may be desired to use a removable proximal end cap on the trocar 1401, for use during insufflation to allow the insufflator 1410 to fill the abdomen, after which time, the pump 1550 of the control unit 1420 can be actuated, and the cap removed. Alternatively, an obturator can be inserted through the trocar 1401 and mutually sealed therewith, such as by O-rings or the like.

The system 1400 pressurizes the insufflation fluid to the desired pressure and can be adapted and configured to treat or condition the fluid as necessary. As set forth above, the pressure supplied to trocars in accordance with the invention can be between about 0 mmHg and 3500 mmHg at any 0.1 mmHg increment of pressure therebetween. Such pressures are suitable for fluid supply plena, such as plenum 141 shown in FIG. 2. However, relatively high pressures can also be supplied to the nozzles of trocars in accordance with the invention, such as nozzle 155, best seen in FIG. 3. In one embodiment, pressure supplied to the nozzle(s) is between about 1000 mmHg and about 2000 mmHg, and can be at any 0.1 mmHg increment of pressure therebetween. In one preferred embodiment, the pressure supplied to the nozzle(s) is about 1530 mmHg. Naturally, normal pressures can vary as needed or desired. Moreover, pressures will decrease from normal when an excessive abdominal pressure is measured, as set forth above.

Figure 15B:
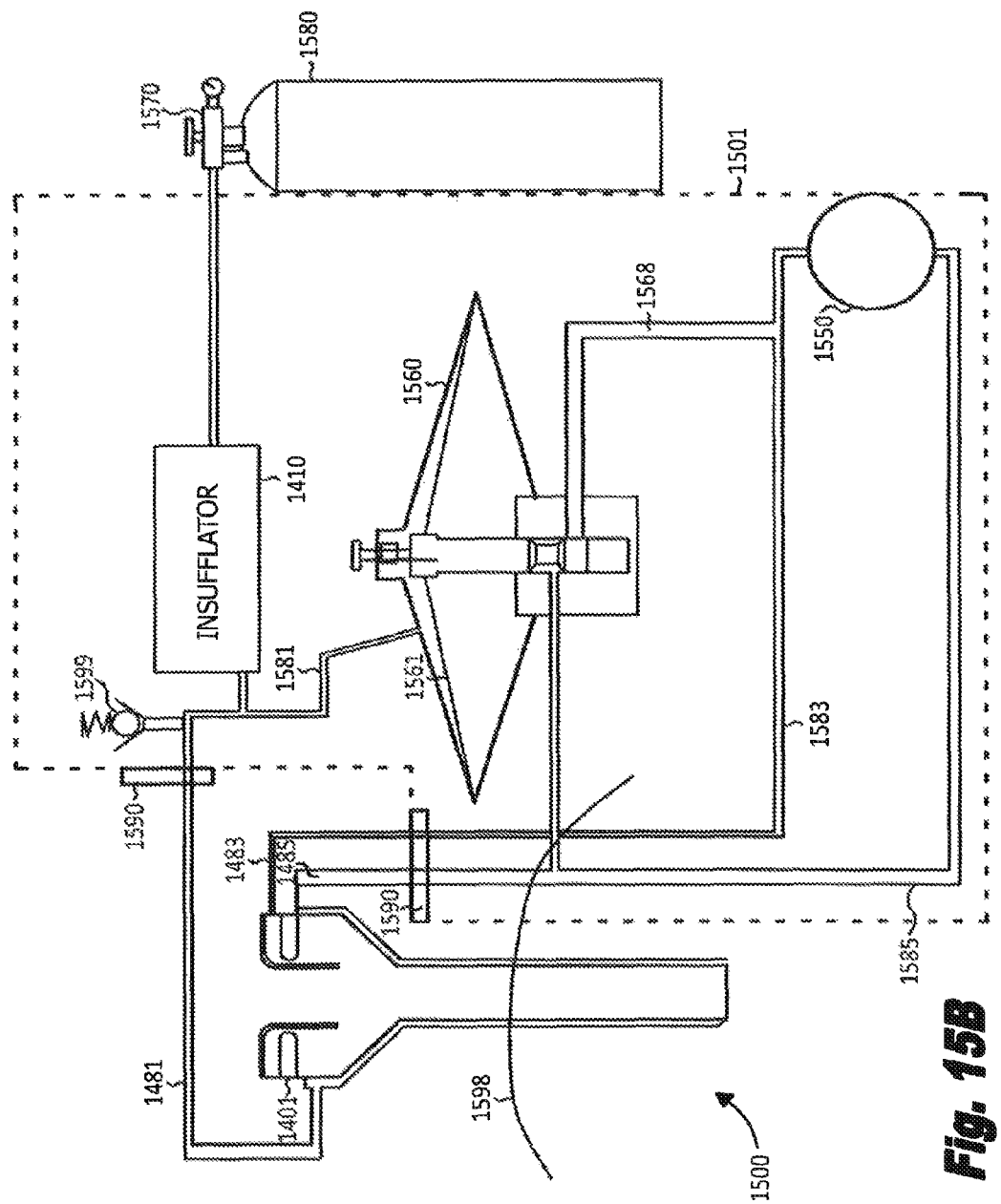
FIG. 15B is an alternate embodiment of the system of FIGS. 14 and 15A, including an integral pressure dumping valve.

FIG. 15B illustrates a system 1500, which is an alternate embodiment of the system 1400 of FIGS. 14 and 15A. The system 1500 is similar to system 1400, but simply additionally includes a safety pressure release valve 1599 in fluid connection with the pressure sensing line 1581. In cases of overpressure, in addition to the short-circuiting action of the pressure-controlled valve 1560, the safety pressure release valve 1599 can additionally release insufflation fluid into the atmosphere. The pressure setting at which the safety pressure release valve 1599 begins to release fluid can be set so that it does not prematurely release fluid, instead of the pressure-controlled valve 1560 recirculating fluid. Accordingly, the pressure setting may be slightly higher than for the pressure-controlled valve 1560.

With reference to FIG. 16, there is illustrated a control unit 1620 which is connected to an insufflating trocar 1401, both in accordance with the invention. A unitary filter element 1682 is provided, which is described in more detail below in connection with FIGS. 20-22. The control unit 1620 can be utilized with any embodiments of the systems described in accordance with the invention, and can include, as illustrated, a settable control 1621 for setting the desired pressure output from the control unit 1620, and a pressure gauge 1625 for confirming the set pressure. As illustrated, the filter 1682 mounts directly to the control unit 1620, with conduits integrally formed with the housing of the filter 1682 being received by corresponding apertures in the control unit 1620, as will be described in more detail below in connection with FIGS. 20-22. As with other embodiments set forth herein, the control unit 1620 can be connected with a standard surgical insufflator or can be provided with insufflator componentry within the housing of the control unit 1620.

Figure 17:
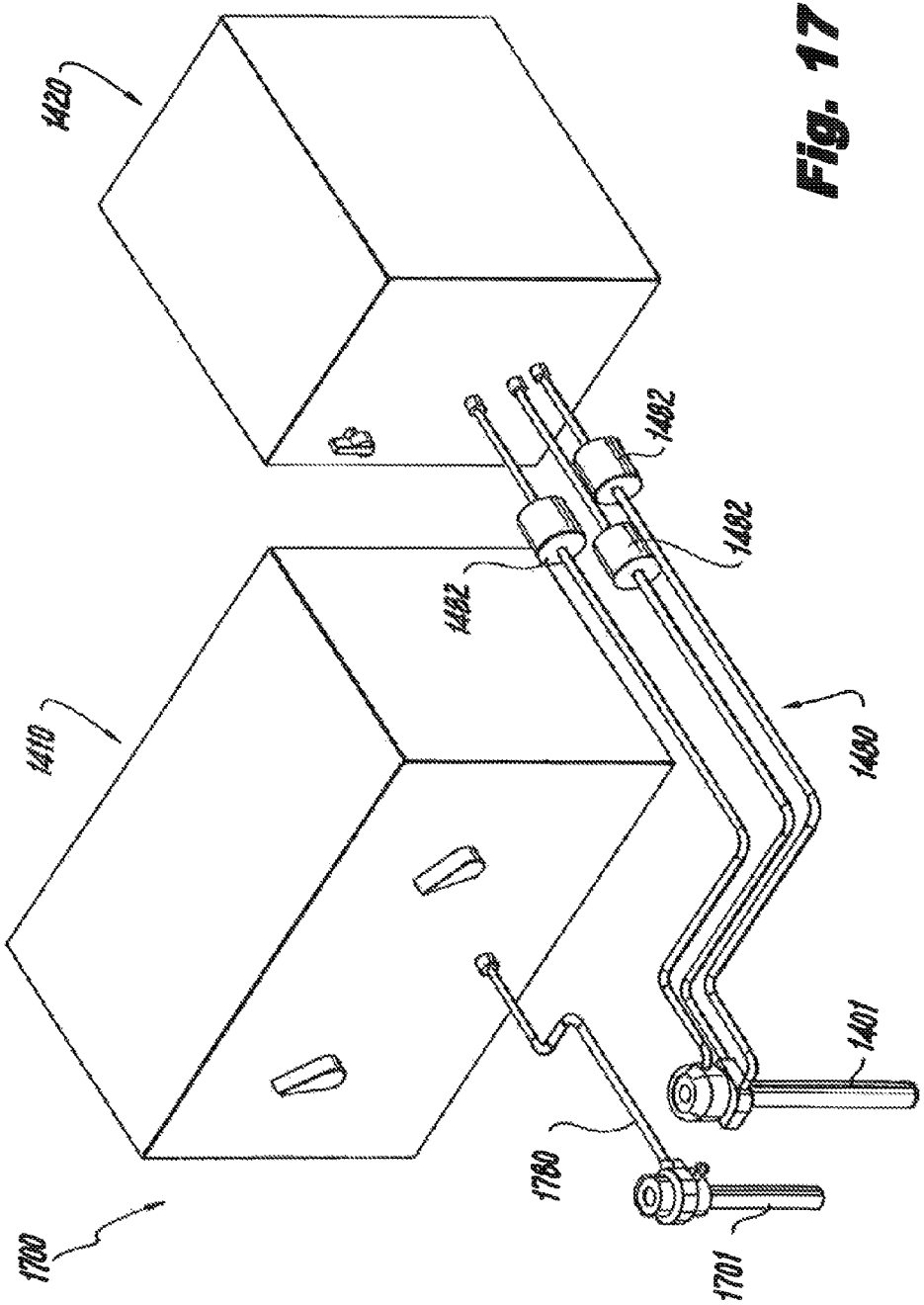
FIG. 17 is an isometric view of a second embodiment of an insufflation and circulation system in accordance with the invention.
Figure 18:
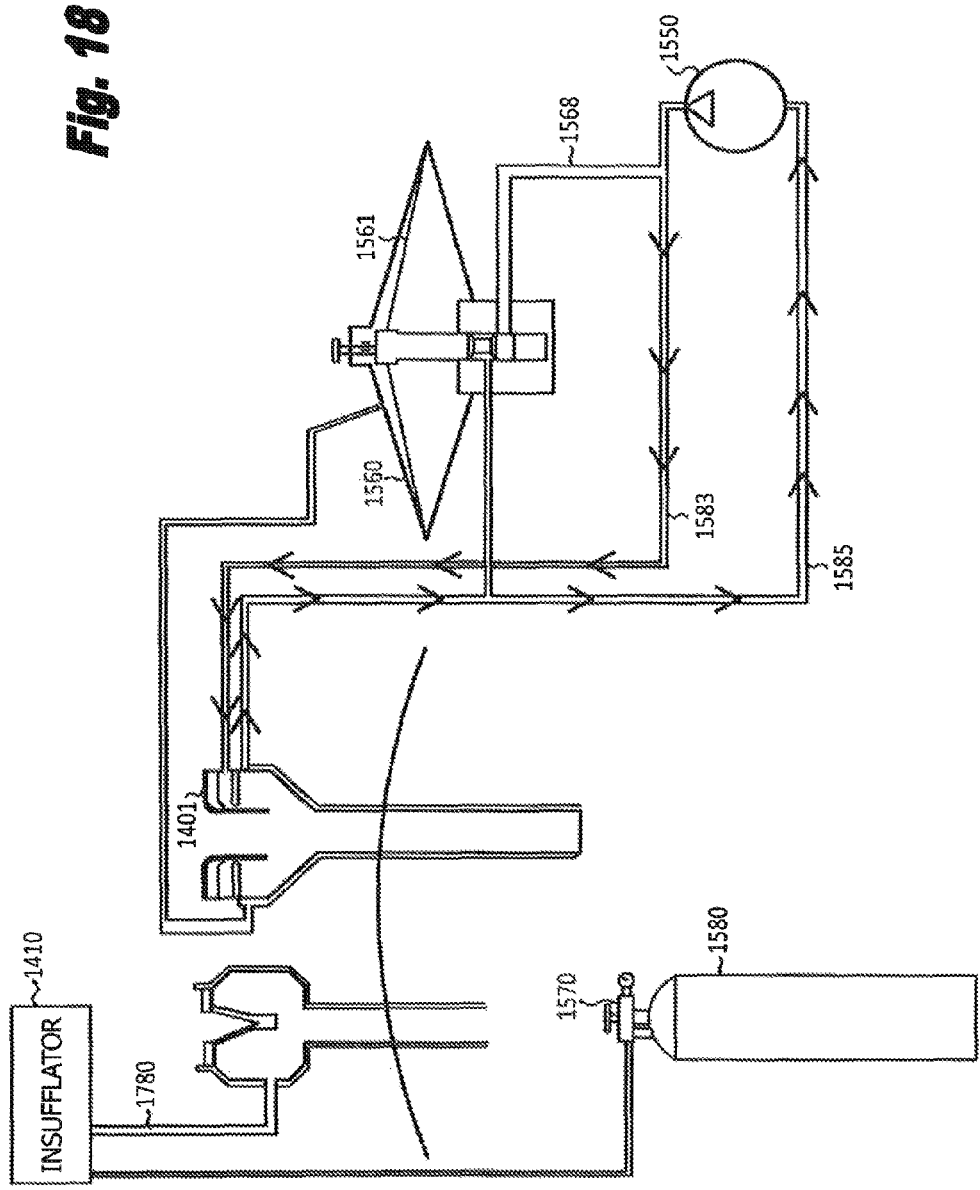
FIG. 18 is an example schematic representation of the main components included within the system of FIG. 17.

FIGS. 17 and 18 illustrate an alternative embodiment of a system for surgical insufflation and gas recirculation 1700. As with the embodiment of FIGS. 14 and 15, an insufflator 1410 and control unit 1420 are each provided. However, the insufflator 1410 and control unit 1420 in this embodiment operate independently from one another, and each independently measures and responds to the abdominal pressure of the patient. As with the embodiment of FIGS. 14 and 15, the trocar having recirculation capability 1401 is connected by way of fluid conduits 1480 and filters 1482 to the control unit 1420. However, the insufflator 1410, instead of being connected to the control unit 1420, is connected by way of a fluid conduit 1780 to a secondary trocar 1701.

As shown in FIG. 18, insufflation gas is provided to the system 1700 from a supply, such as a tank 1580. In operation, when low abdominal pressure is sensed, the insufflator 1410 is triggered to insufflate the abdomen, and the pressure-controlled valve 1560 remains in a closed state, with the fluid pump 1550 receiving fluid from a return fluid plenum in the trocar 1401, through the return fluid conduit 1585, and delivering pressurized fluid through the fluid supply conduit 1583 to the nozzle of the trocar 1401.

When excessive abdominal pressure is experienced, the insufflator does not provide additional insufflation fluid to the abdomen, and the pressure-controlled valve 1560 opens, connecting the fluid supply conduit 1583 and the return fluid conduit 1585 through the bypass conduit 1568, thereby reducing the effectiveness of a fluid seal formed in the trocar 1401, and allowing a portion of the insufflation fluid to escape, and allowing the pressure within the abdominal cavity.

Figure 19:
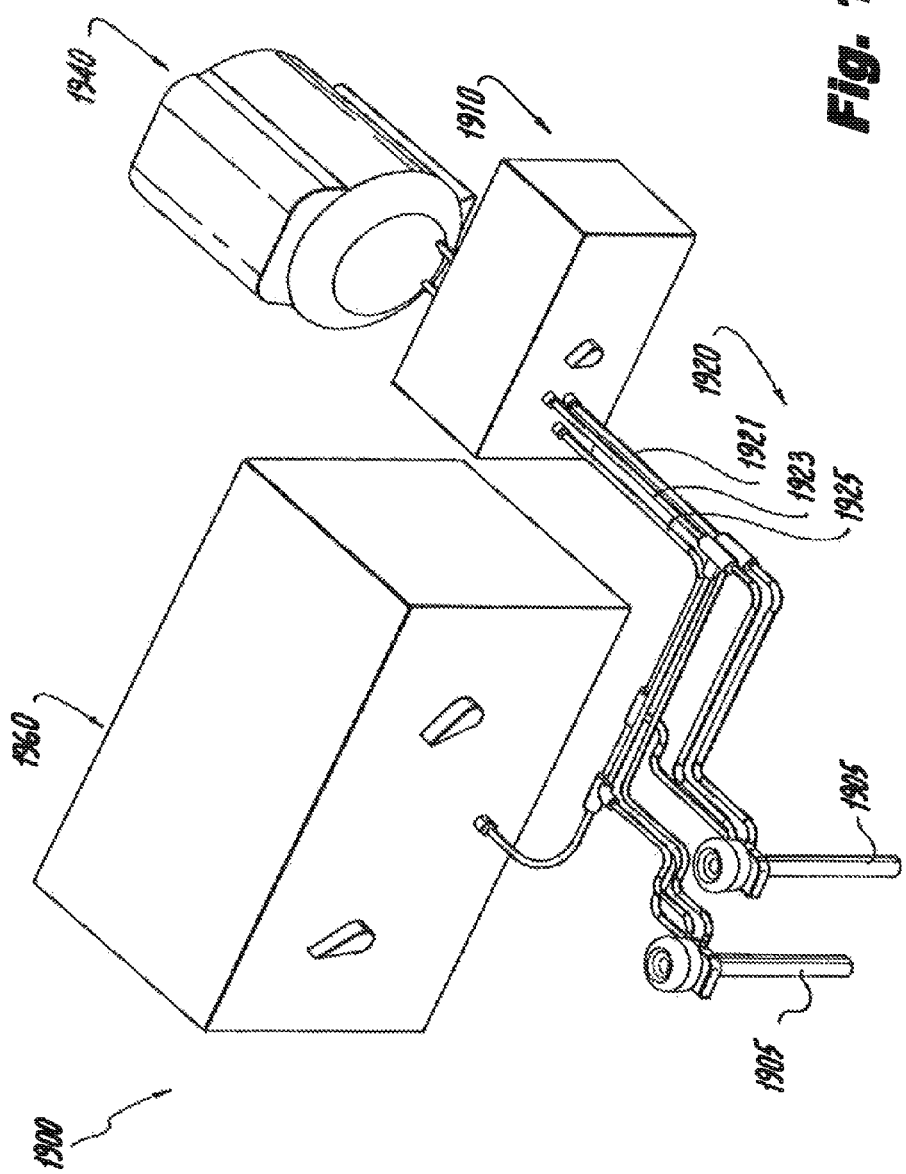
FIG. 19 is an isometric view of an alternate configuration of an insufflation and recirculation system in accordance with the invention.

With reference to FIG. 19, there is illustrated a system 1900 in accordance with the invention in which surgical access devices 1905 are connected via tubes 1920 to control equipment. In this case, control equipment includes an insufflator 1960, and a control unit 1910, which in turn is operably connected to a recirculation pump 1940, but which may include the pump 1940 within the housing of the control unit 1910.

In accordance with the invention, preferably all internal, gas contacting surfaces of the system, including tubing 1921, 1923, 1925 and portions of the recirculation pump 1940 are disposable. The pump 1940 may be of a peristaltic design, pumping gas by flexing disposable tubing, such as by a compressive roller system. Alternatively, pumping can be accomplished by external manipulation of a closed, integral and disposable diaphragm element. In accordance with the invention, it is preferred that wetted surfaces be disposed of after each procedure as a precautionary measure against cross-contamination. In alternate embodiments, systems in accordance with the invention can be provided with other types of fixed displacement pumps, or a variable displacement pump, such as vane pump, for example.

The surgical access devices 1905 are connected to the insufflator 1960 and control box 1910 by way of a pressure sense tube 1925. Pressurized fluid is delivered to the surgical access devices 1905 by way of a fluid supply tube 1921, while spent insufflation gas is retrieved by way of a return tube 1923, each tube being connected through a control unit 1910. One or more intervening filters can be disposed between the access devices 1905 and the control unit 1910, as illustrated in FIGS. 16 and 17.

A main fluid supply, such as a bottle of carbon dioxide gas, can be incorporated into the system 1900 in any suitable fashion, such as by providing an input in the control unit 1910, for example.

Figure 20:
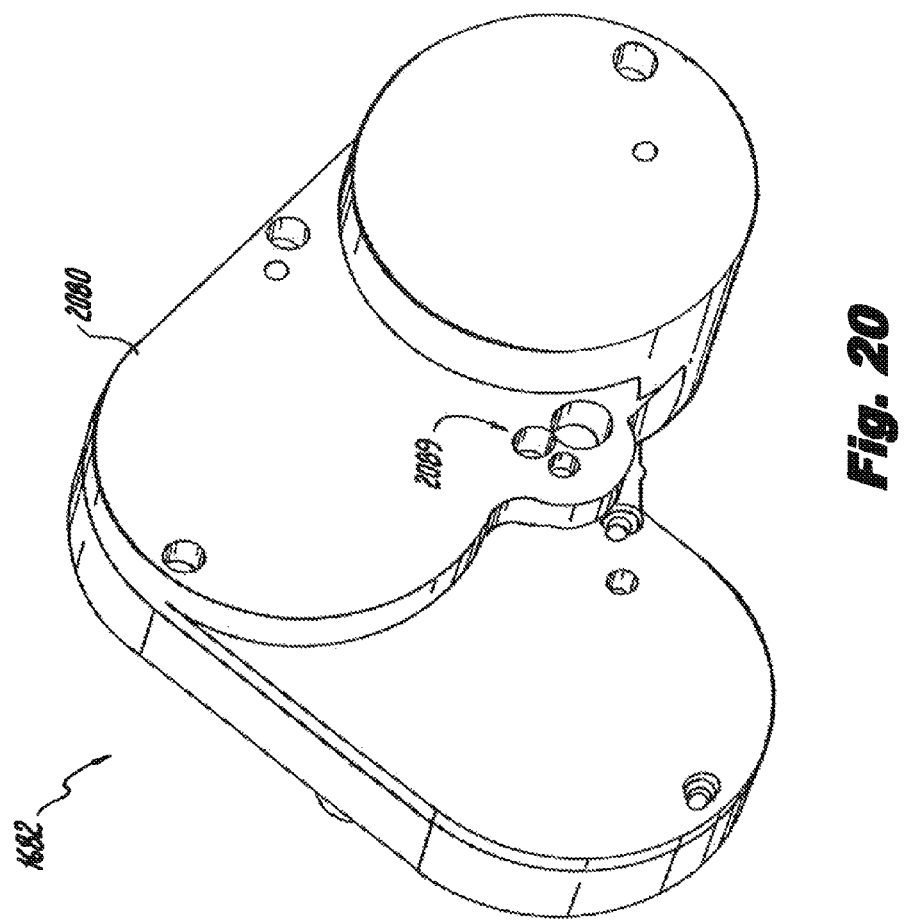
FIG. 20 is an isometric front view of a filter housing in accordance with the invention.
Figure 21:
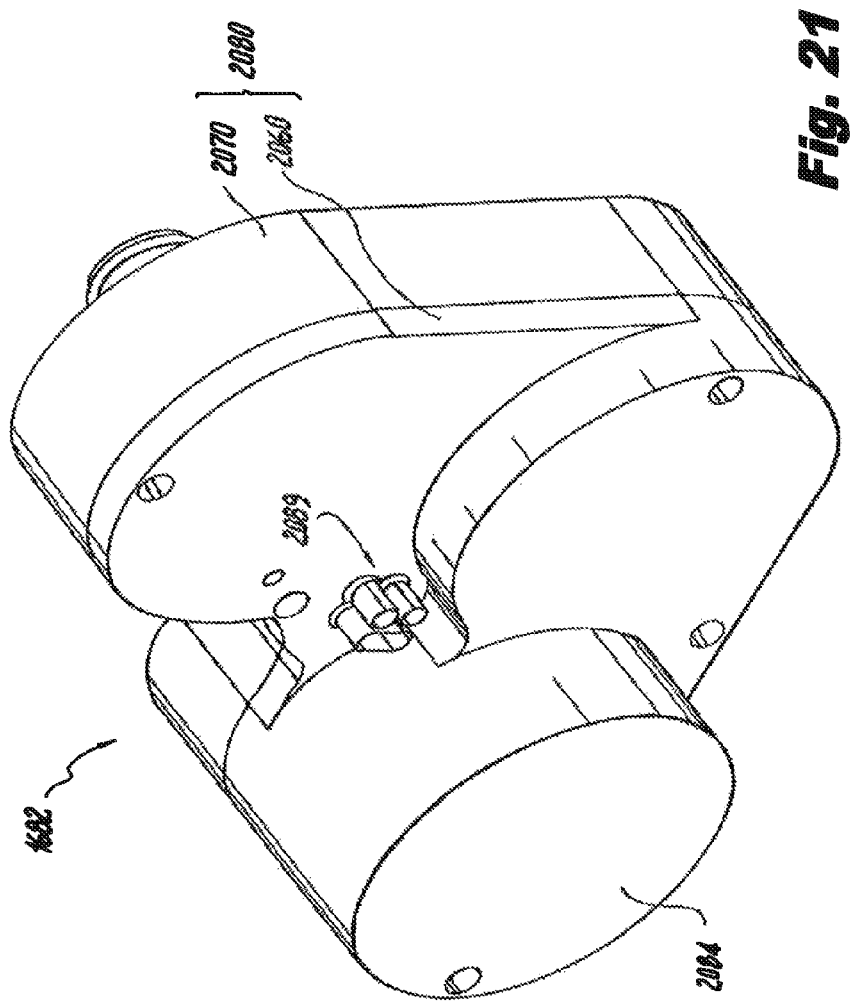
FIG. 21 is an isometric side view of the filter element of FIG. 20.
Figure 22:
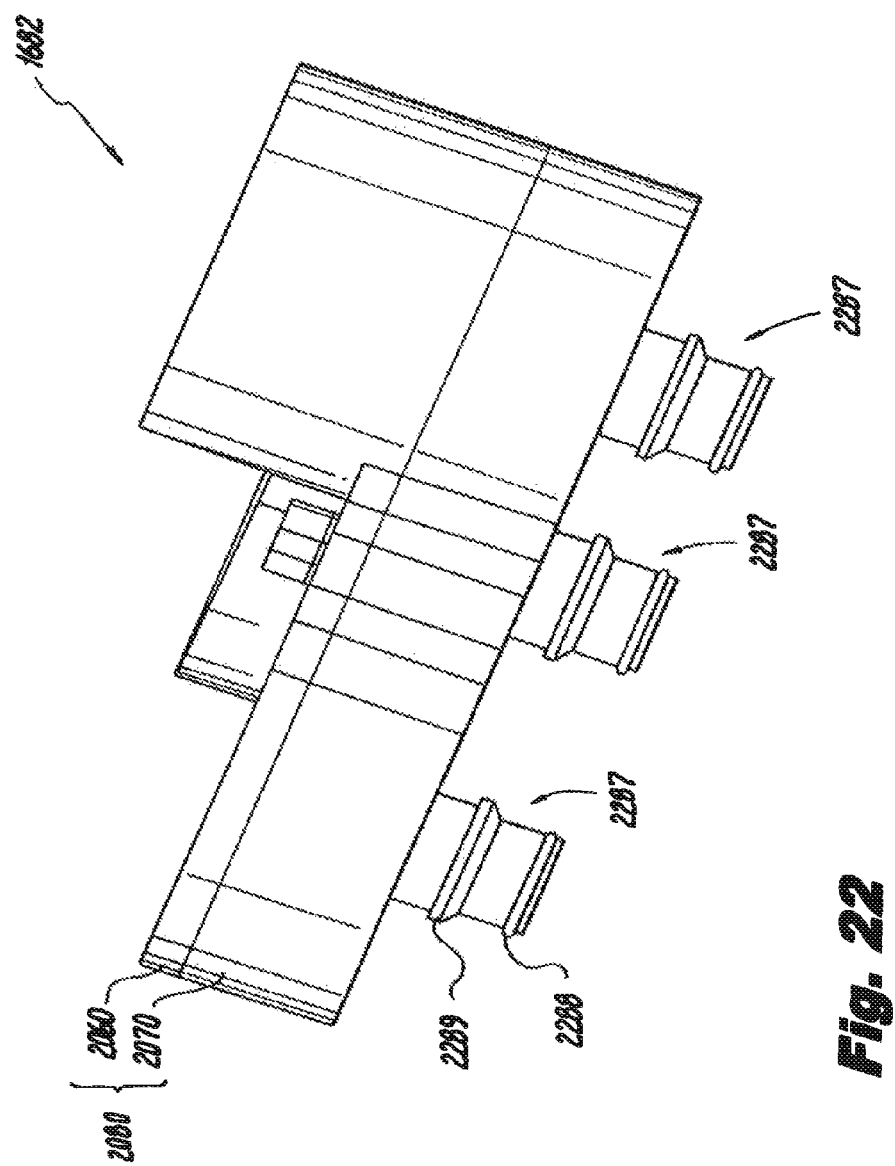
FIG. 22 is another isometric side view of the filter element of FIG. 20.
Figure 23:
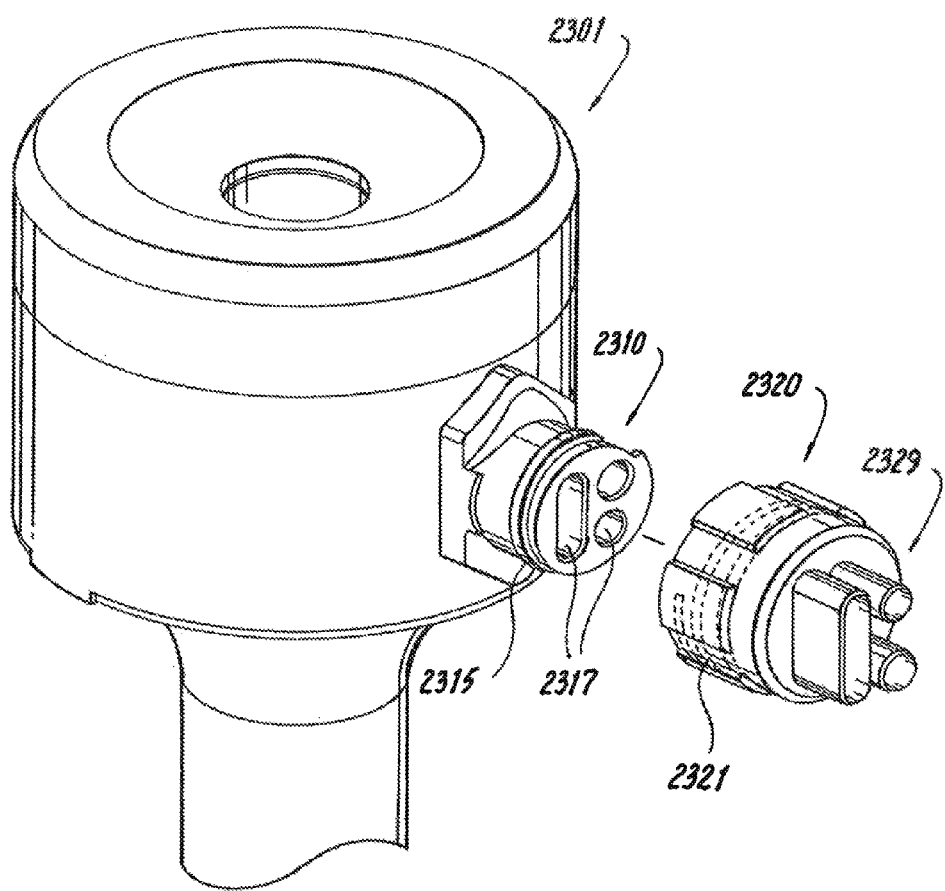
FIG. 23 is an isometric view of a connection between a tube set and a trocar, in accordance with the invention.
Figure 24:
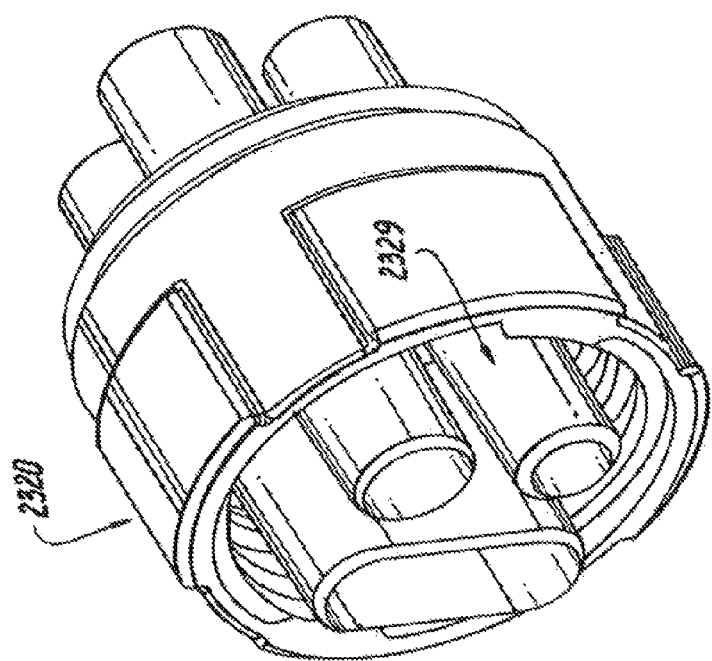
FIG. 24 is an isometric view of a tube end connector in accordance with the invention.
Figure 25:
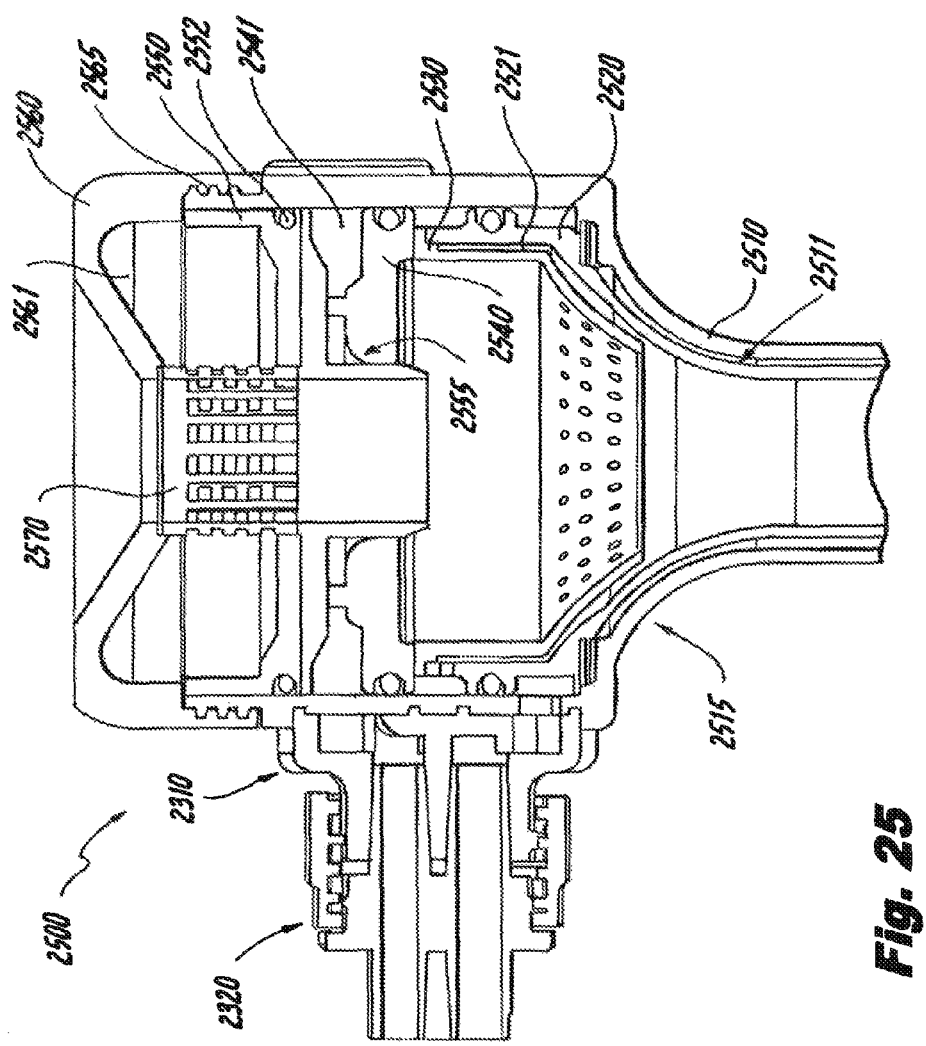
FIG. 25 is a cross-sectional view of a further embodiment of a trocar in accordance with the invention connected with a tube set.
Figure 26:
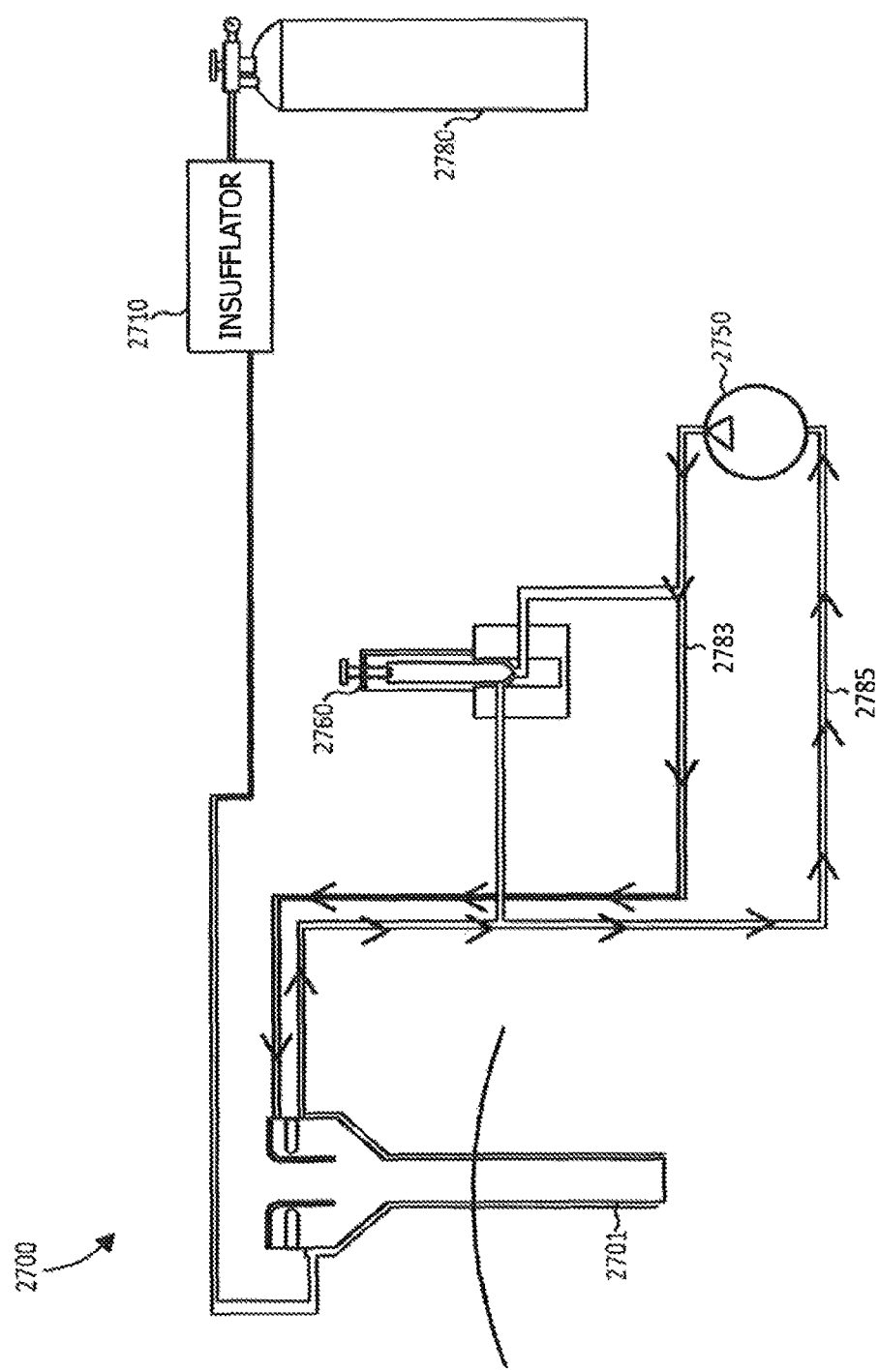
FIG. 26 is an alternate embodiment of an insufflation and recirculation system in accordance with the invention, having a back pressure control valve.

Turning now to FIGS. 20-22, a filter assembly 1682 is illustrated. The filter assembly 1682 is provided with a housing 2080. The housing 2080 can be molded in two parts to simplify assembly, and can hold within it filter elements within separate, defined chambers corresponding to each of a fluid supply, fluid return and pressure sensing and/or insufflation conduit. Due to the different flow rates and pressures passing through each respective conduits, the filter size for that conduit is selected accordingly. As illustrated, particularly in FIG. 20, conduits 2089 are provided in the housing 2080, each in fluid communication with a fluid path and its respective filter element held within the housing 2080. The connection between the tubes and the filter 1682 can be any desired, and in accordance with the invention may be the same as the connection between the trocar and tube set, as illustrated in FIGS. 23-25, described in further detail below.

FIG. 21 is an isometric view of the filter 1682, illustrating the tube connection conduits 2089, and the parts 2060, 2070 that comprise the majority of the filter housing 2080. The front lid 2060, with conduits 2089 formed therein, is attached to the rear portion 2070, holding therewithin a plurality of filter elements for filtering fluid received from or provided to the trocar.

A fluid drain can be provided in one or more of the chambers defined within the housing 2080, particularly with the chamber 2084 corresponding to fluid returned from the trocar. Such drain can in-turn, be connected to a central suction system to remove any collected fluid, or fluid can simply collect in the bottom of the housing 2080, or in a separate reservoir. As embodied, this chamber 2084 is preferably volumetrically larger than the other two chambers to accommodate a depressurized, and thus expanded flow of fluid returning from the trocar. The pressurized fluid being provided to the trocar takes up a proportionately lower volume, and accordingly, smaller filter chambers and tubes are sufficient to carry a given mass flow rate of insufflation fluid. When that same fluid is expanded upon its return, a larger conduit and filter chamber are necessary to handle the flow of fluid.

FIG. 22 is a side isometric view of the filter 1682, illustrating the rear conduits 2287 defined in the rear portion 2070 of the housing 2080. The conduits 2287 are configured to mate with corresponding apertures in a control unit, and include sealing elements 2288, such as O-rings, and protrusions 2289 for engaging a cooperating element in the housing to securely engage the filter 1682 to the control unit. Of course, the filter 1682 can be embodied such that instead of mounting on a control unit, the rear end of the filter connects to an intermediate tube set.

FIG. 23 illustrates two mating connection elements, including a boss 2310, and an end connector 2320 for connecting a trocar 2301 in accordance with the invention to a tube set (FIG. 24b). The same connection arrangement can be used between the tube set and the filter, if so desired. A locking nut 2321 on the end connector 2320 engages an outer thread portion 2315 of the boss 2310, holding conduits 2329 securely to the trocar 2301. The conduits 2329, particularly on the end mating with the corresponding apertures 2317 formed in the boss 2310, can be formed of a compliant material such that they self-seal against the inner walls of respective apertures 2317. Alternatively or additionally, separate sealing elements can be utilized without departing from the spirit or scope of the invention. The general construction of the threaded engagement can be that of a "luer lock," is so-desired.

FIG. 24 is an isometric view of the mating side of the end connector 2320. It is envisioned that a multi-lumen tube can be used with the subject connector 2320 and systems of the invention. It is to be understood that the connector 2320 and systems in accordance with the invention can function utilizing separate tubes, however a multi-lumen tube can be provided to simplify procedures in the operating room and to reduce encumbrances to the surgical team. The multi-lumen tube can be extruded in one step as a unitary component. Alternatively, the multi-lumen tube can be formed as separate tubes which are then bound together in a suitable manner, such as by fusing adjacent walls to one another, or by over-wrapping the tube with another material. Moreover, strain relief elements can be molded into, over-molded onto or otherwise applied to the tube set across its entire length, or at one or more of the ends thereof. Such strain relief elements can include metal or relatively rigid polymeric elements, such as coils, which resist strain of the assembly to inhibit kinks in the tube or to prevent damage thereto. It is to be understood that the entire cross-sectional length of the tube is in a preferred embodiment, contiguous and unbroken. The tube can be of any length desired, but will typically range from between about 2 to 4 meters in length for single main tubes. In alternate embodiments, conduits can be branched off therefrom, as needed to supply multiple devices. It is further conceived that for this purpose, a manifold adapter can be provided for splitting flows between a control unit and a surgical device, for example.

An alternate tube set may be provided having a dual-lumen tube portion, and a separate single lumen portion, which can be used, for example, for pressure sensing and/or insufflation functions. The alternative features discussed above in connection with the multi-layered tube set are applicable to this tube set. Advantageously, a separate insufflation and/or pressure sensing tube allows for alternate and remote placement of one or both of these functions. This can also reduce the overall size of access devices of the invention, as integration of an insufflation and/or pressure sense channel therewith is not needed.

FIG. 25 illustrates a trocar 2500 including a body 2510, having a housing 2515 arranged at the proximal end portion thereof. An annular insert 2540 and a nozzle insert 2550 define, in conjunction, a nozzle 2555 and a fluid supply plenum 2541. A fluid return plenum 2521 is defined between two inserts 2520 and 2530. Seals, 2552, such as O-rings can be provided in respective detents to seal between the inserts and the housing 2515. The nozzle insert 2550 is formed so as to have a depressed region which helps accommodate a proximal sound attenuation chamber 2561, in cooperation with a proximal cap 2560. Sound absorbing material can be provided in the sound attenuation chamber 2561 to help reduce noise emitted by the flowing fluid within the trocar 2500. A grating insert 2570 can be provided to help hold in and protect the sound attenuating material, and help further absorb excess sound.

The cap 2560, as illustrated, is adapted to threadedly engage the housing 2515 by way of mating threads 2565 formed on the housing 2515 and cap 2560. When assembled, screwing the cap 2560 to the housing 2515 causes all inserts to be firmly held within the housing 2515, providing for simple assembly of the trocar 2500.

The fluid return plenum 2521, fluid supply plenum 2541 and pressure sense and/or insufflation plenum 2511 are in fluid connection with respective conduits, which are connected through the connection boss 2310 provided on the housing 2515. The connection boss 2310, as described above, connects with a tube end connector 2320 to facilitate fluid supply to and removal from the trocar 2500.

Figure 27:
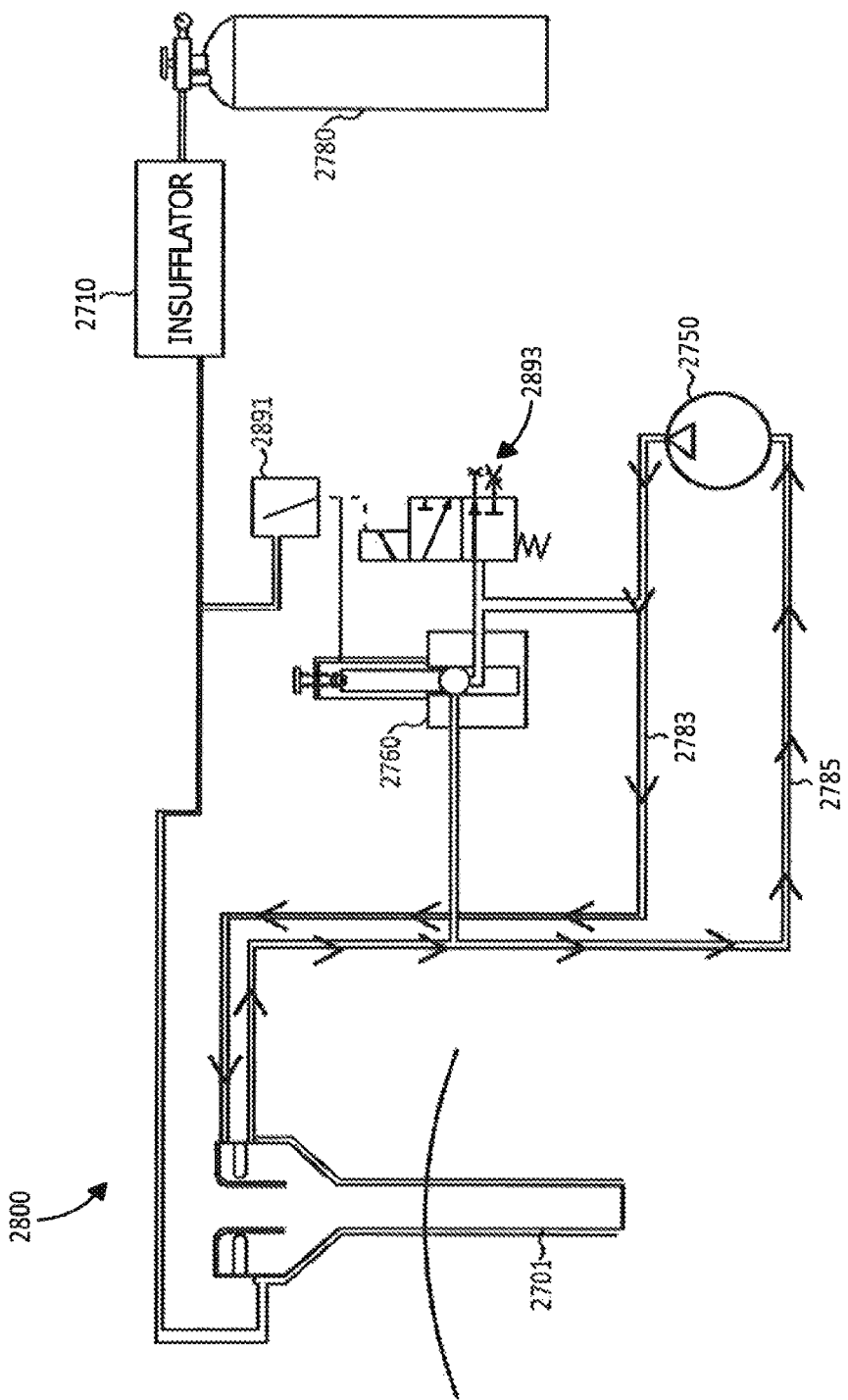
FIG. 27 is a further alternate embodiment of an insufflation and recirculation system in accordance with the invention, having a back pressure control valve, a pressure sensor and a pressure dump valve.
Figure 28:
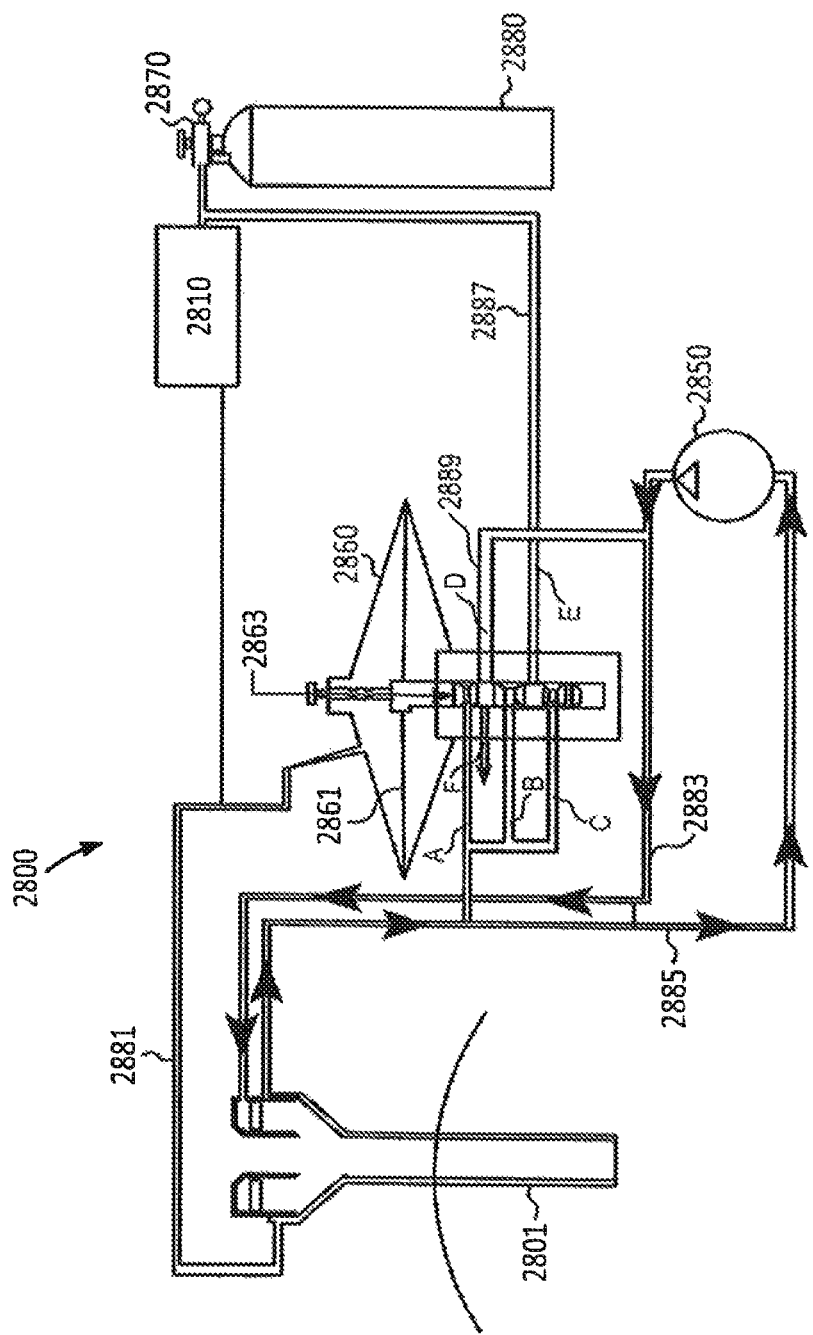
FIG. 28 is a schematic illustration of a recirculation system in accordance with the invention having bypass and insufflation gas flood capability.

FIGS. 27 and 28 are schematic illustrations for alternate systems 2700, 2800 in accordance with the invention. The systems 2700, 2800 of FIGS. 27 and 28, can be incorporated integrally with a surgical insufflator similar to the embodiments of FIGS. 15A and 15B, or may be independent of a surgical insufflator like the embodiment of FIGS. 17 and 18, with the insufflator 1410 and control unit 1420 operating independently from one another, and each independently measuring and responding to the abdominal pressure of the patient.

In each embodiment, the trocar having recirculation capability 2701 is connected to an insufflator 2710, a pump 2750 and a valve. In the embodiment of FIG. 27, the valve 2760 is a back pressure control valve, which permits pressure on the upstream side of the valve 2760 only up to a certain preset value. When pressure in supply the conduit 2783 exceeds the set value, it short-circuits to the return line 2785. This lowers the supply pressure and reduces or shuts off the fluid seal created by the pressurized flow entering the trocar 2701, thereby allowing insufflation fluid in the abdominal cavity to escape through the lumen of the trocar 2701. Because the lumen of the trocar can be relatively large, such pressure can escape quickly, thereby preventing any harm to the patient. Because the fluid is recirculated in the valve, a minimum of insufflation gas is wasted by dissipating it into the atmosphere.

The system 2800 of FIG. 28 includes an additional dump valve 2893 in connection with the fluid supply conduit 2783. In addition to the short-circuiting action of the pressure valve 2860 described above, the system 2800 is provided with a pressure sensor 2891, which can be mechanical but is, as illustrated, electronic. The pressure sensor 2891 can be in fluid communication with the insufflation line or other source of abdominal pressure. When an over-pressure condition is sensed, the pressure sensor 2891 signals the dump valve 2893 to release fluid out of the system. As illustrated, the dump valve 2893 is electro-mechanical, but alternatively may be fully mechanical, as desired.

FIG. 28 is a schematic illustration of a recirculation system 2800 in accordance with the invention. As with foregoing embodiments, insufflation gas is provided from a tank 2880 and pressure regulator 2870 or other source, such as a central gas distribution system, for example. As with foregoing embodiments, an insufflator 2810 is provided, and in this embodiment is connected by way of a pressure sense and insufflation conduit 2881 to the trocar 2801. The pressure sense and insufflation conduit 2881 is also in fluid communication with a diaphragm valve 2860, with internal diaphragm 2861 and movable spool 2863. The spool 2863 is adjustably connected to the diaphragm, such that the spool moves in response to a change in abdominal pressure, as conducted through the pressure sense and insufflation conduit 2881. The spool 2863 then opens and closes internal fluid paths A-F within the valve 2860 body in response to the change in pressure, as will be described in more detail below.

As with foregoing embodiments, a supply line 2883 and return line 2885 are provided in connection with a recirculation pump 2850, for providing supply fluid and for returning fluid for recirculation, respectively. Additionally, a supply bypass conduit 2889 leads from the supply line 2883 to port D of the valve 2860, and an insufflation gas bypass conduit 2887 is provided between the gas supply, such as a tank 2880, and port E of the valve 2860.

The illustrated system 2800 is capable of controlling the fluidic seal formed in the trocar 2801. The system 2800 provides pressure to the trocar 2801, resulting in constant abdominal pressure under normal operation and acts as a safety valve, eliminating input pressure from the air seal under circumstances of excess pressure.

The system 2800 and valve 2860 are configured and adapted to regulate the supply pressure to the trocar 2801 air seals so as to maintain a constant, set pressure in the abdominal cavity, to slow the restoration from low pressure situations so as not to entrain excessive unwanted ambient air into the abdomen, to flood the air seal entrance during pressure restoration with the insufflation gas, such as carbon dioxide, to insure that entrained makeup gas is predominantly the desired gas, and to divert supply gas from the pressure supply line to the return line, relieving excessive pressure which might otherwise harm the patient.

The subject system 2800 and valve 2860 are capable of regulating the supply pressure to the trocar air seals so as to maintain a constant, abdominal pressure within small tolerances, preferably to one mm Hg of the set pressure, under normal operation. The selected abdominal pressure is set by way of a calibrated adjustment knob, or alternatively an electronic selector. In accordance with one aspect, the setting range is between about 5 to 18 mm Hg of abdominal pressure.

In the case of normal abdominal pressure during a surgical procedure, recirculation of insufflation gas through the pump 2850 and conduits 2883, 2885 occurs normally, and no gas is sent through the bypass conduits 2887, 2887 from the pump or insufflation gas supply, respectively.

If abdominal pressure increases beyond a set point, which may occur due to pressure placed on the insufflated abdominal cavity, for example, the spool 1963 moves in response to excess pressure on the diaphragm 1961 and opens a fluid path between ports D and A, thereby opening the bypass conduit 2889, causing pressurized supply gas from the supply conduit 2883 to be recycled to the return conduit 2885.

In accordance with one aspect, under high pressure circumstances, the valve 2860 will divert all of the supply gas from the supply line 2883 to the return line 2885 or exhaust (port F of the valve 2860) if the abdominal pressure exceeds the set pressure by a predetermined amount, which in accordance with one aspect of the invention is sixty percent.

If abdominal pressure continues to rise, displacement of the spool 2863 causes a path between ports D and F to be opened, resulting in a "dump" of insufflation gas, which can be the operating room, or alternatively, a waste collection system. In such an instance, the pump 2850 is drawing gas from the trocar 2801, but little or no insufflation fluid is being provided back to the trocar, allowing abdominal pressure to safely revert to normal.

In the case of very low sensed abdominal pressure, which in a preferred aspect is any value 4 mm Hg or more below the set value, the spool 2863 opens a path between ports D and B, to reduce flow to the nozzle of the trocar, and thereby to reduce the severity of air entrainment from the surrounding environment. Additionally or alternatively, the spool 2863 opens a path from port E to port C to increase the concentration of pure insufflation gas (typically carbon dioxide gas), and in that manner, flood the opening of the trocar 2801 with a high concentration of pure insufflation gas. In this manner, any gas that is entrained through the trocar 2801 will have a relatively high proportion of pure insufflation gas (e.g., carbon dioxide gas). Naturally, it is to be understood that the term "pure" may in fact be a mixture of gasses supplied to the subject system, the intention being that such gas is drawn into the operative space instead of surrounding gasses, which may have an undesirably high concentration of oxygen, other gasses or contaminants.

Although filtration elements are not explicitly illustrated in the embodiment of FIG. 28, it is to be understood that, as with any other embodiments set forth herein, such elements can be provided at any point in the system 2800 necessary, such as prior to entering the tubing to the trocar, and when returning from the trocar. A filter element can also be provided in-line with the insufflation and pressure sense line 2881.

Figure 29:
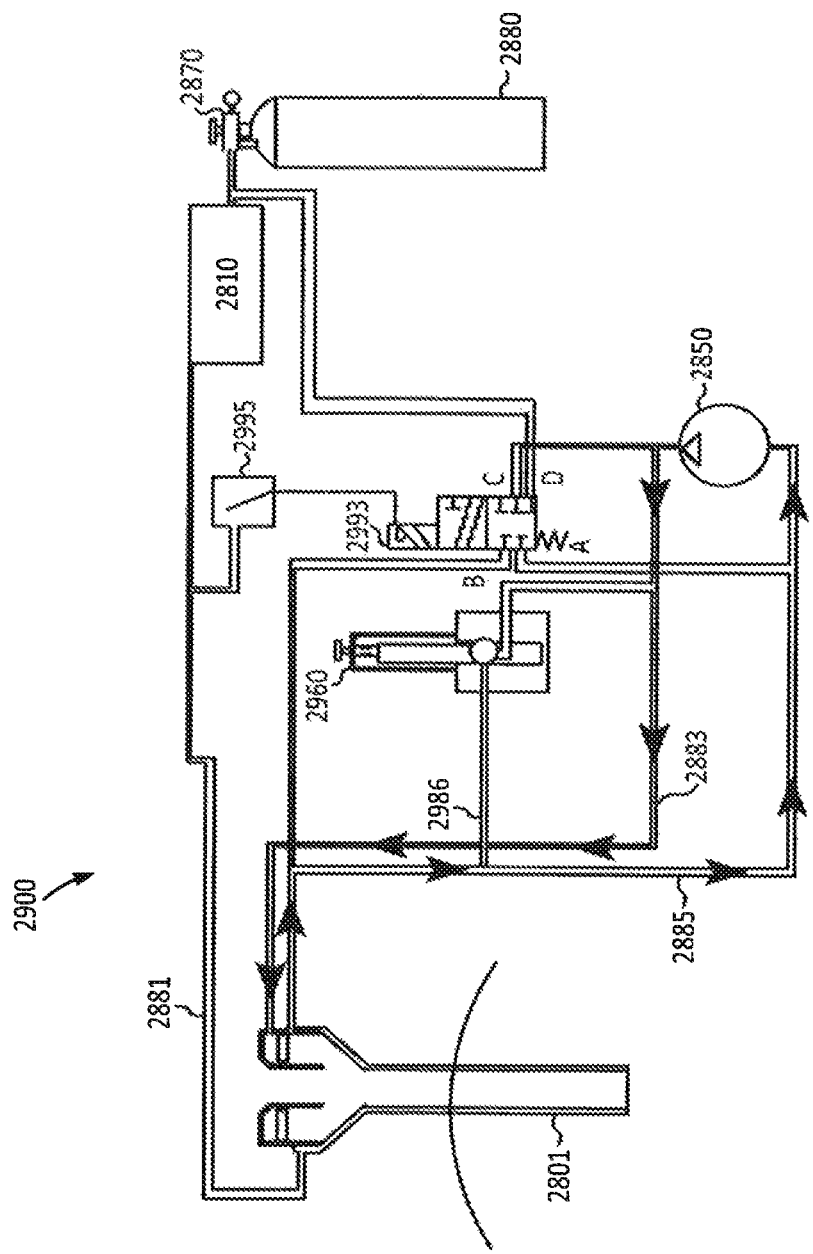
FIG. 29 is a schematic illustration of a recirculation system in accordance with the invention similar to the embodiment of FIG. 28, but utilizing an electromechanical valve.

FIG. 29 is a schematic illustration of a recirculation system 2900 in accordance with the invention, similar to that of the system 2800 of FIG. 28. In the system 2900, instead of purely mechanical valve control, a combination of mechanical and electromechanical valves is used. As with the foregoing embodiment, a trocar 2801 having air-sealing capability, a recirculation pump 2850, insufflation gas source 2880 and pressure regulator 2870 are provided. A supply line 2883 and return line 2885 are provided and deliver pressurized insufflation fluid to and deliver spent fluid from the pump 2850.

In the system 2900 of FIG. 29, a relief valve 2960 is provided, which controls fluid flow through a bypass conduit 2986. As illustrated, the valve 2960 is configured to respond to a situation where an input pressure in the supply conduit 2883 is above a set pressure, however, the valve 2960 can be replaced by an active valve, such as the above-described diaphragm valves that respond to abdominal pressure.

In the illustrated embodiment, in parallel with the relief valve 2960, is arranged an electromechanical valve 2993, which in the illustrated embodiment received input from a pressure sensor 2995. The pressure sensor 2995, naturally can take on any form, and can include intervening controls that allow a pressure threshold to be selected.

As with the system 2800 of FIG. 28, the valve 2993 provides for a bypass of the fluid being sent to the trocar 2801, as a supplement to that provided by the relief valve 2960. The valve 2993 also provides for supplemental introduction of insufflation gas from the source 2880 at low insufflation pressures to mitigate the effect of any entrained ambient air. That is, in accordance with this embodiment, when the valve 2993 is triggered, flow is short-circuited from port C to port B, reducing flow to the nozzles in the trocar 2801, while port D is opened to port A, which increases the concentration of the desired insufflation gas—e.g., carbon dioxide gas.

Additionally, as with the foregoing embodiments, one or more filters can be provided in the system 2900 to filter gas sent to or returning from the trocar 2801, if desired or required.

Advantageously, in accordance with the embodiments of FIGS. 28 and 29, the set point at which the valve controlling the flow of excess pure insufflation gas, and the amount provided at that point, and proportional to any sensed pressure can be selected to as to balance efficient use of pure insufflation gas with the proportion of gasses within the abdominal cavity of the patient. Additionally, such selection can be adjusted automatically during the surgical procedure. For example, one or more sensors can be provided in the systems 2900, such as in conjunction with the return conduit 2885 and/or the insufflation conduit 2881. If an undesirably large proportion of oxygen, or other unwanted gas, such as methane are detected, the system 2900 can be adapted to switch on supply of pure insufflation gas to displace the gas detected within the abdominal cavity. In accordance with a preferred aspect, a minimum of 70% carbon dioxide gas is maintained in the abdominal cavity during a surgical procedure.

Figure 30:
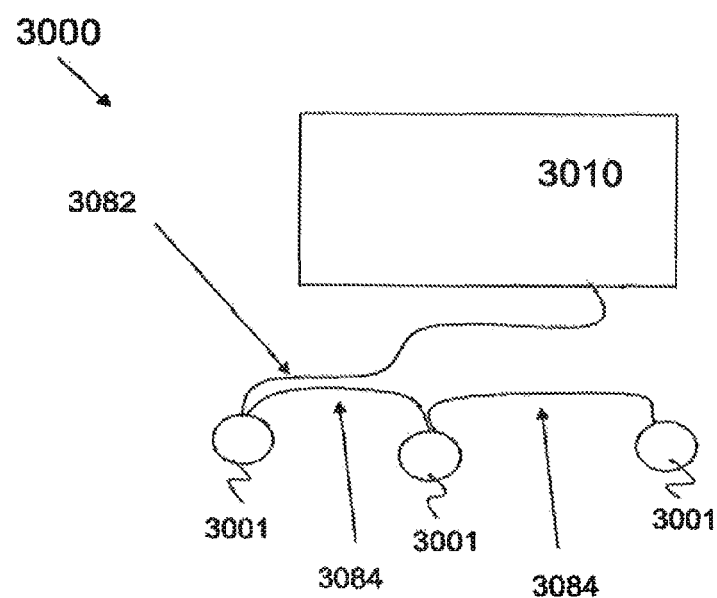
FIG. 30 illustrates a system in accordance with the invention having an insufflation and recirculation unit and a plurality of air-sealed trocars provided in a "daisy chain" arrangement.

FIG. 30 illustrates a system 3000 in accordance with the invention having an insufflation and recirculation unit 3010 and a plurality of air-sealed trocars 3001 provided in a "daisy chain" arrangement. As illustrated, one trocar 3001 is connected by way of a first tube set 3082, and the other trocars are connected in-turn with second and third tube sets 3084. Each tube set includes at least a supply conduit, such as conduit 2883, and a return conduit, such as conduit 2885, and depending on the embodiment also a pressure sense and insufflation conduit, such as conduit 2881, for example. In accordance with the invention, each trocar 3001 is in fluid communication with the insufflation and recirculation unit through the respective tube sets. Fluid may flow through respective chambers provided on each of the trocars, or alternatively through a channel provided in conjunction with the tube sets. Such channel can be integrally formed with the tube sets, or provided as an add-on connector, so that tube sets in any combination of desired lengths can be selected in an operating room.

Additionally, in accordance with any embodiment set forth herein, recirculation components and insufflation components can be provided in a common housing, or alternatively, a standard insufflator can be used in conjunction with a recirculation device in order to achieve the functionality of the devices described herein.

Figure 31:
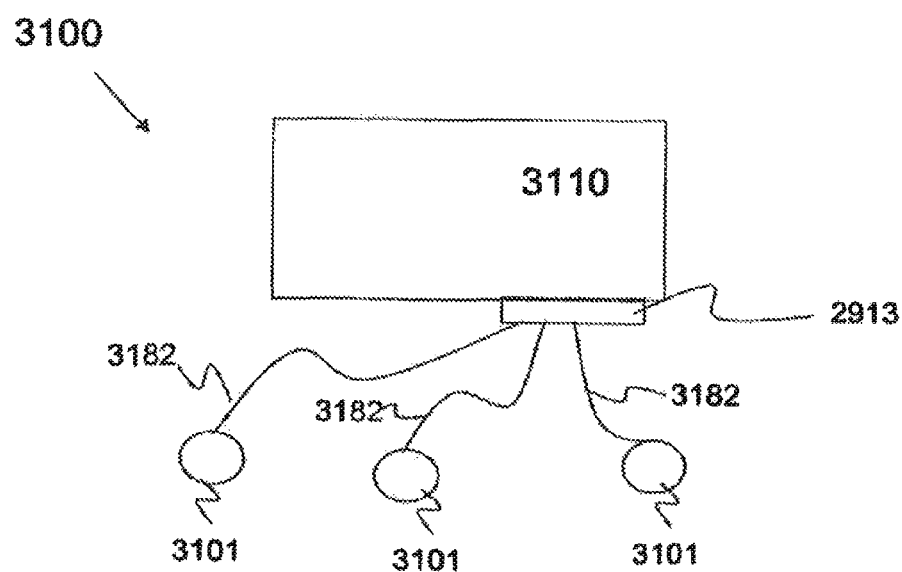
FIG. 31 illustrates a system in accordance with the invention having an insufflation and recirculation unit and a plurality of air-sealed trocars provided in parallel.

FIG. 31 illustrates a system 3100 in accordance with the invention having an insufflation and recirculation unit 3110 and a plurality of air-sealed trocars 3101 provided in parallel. As illustrated, each trocar 3101 is connected by way of a tube set 3182 to the insufflation and recirculation unit 3110. Each tube set includes at least a supply conduit, such as conduit 2883, and a return conduit, such as conduit 2885, and depending on the embodiment also a pressure sense and insufflation conduit, such as conduit 2881, for example. In accordance with the invention, each trocar 3101 is in fluid communication with the insufflation and recirculation unit through the respective tube sets. At the insufflation and recirculation unit 3110, each tube set is connected by way of a distribution plenum 2913, which can be adapted and configured to allow connection of any number of air-sealed trocars in accordance with the invention. For example it is conceived that it may be desirable to have the capability to use up to six air-sealed ports simultaneously. Accordingly, the distribution plenum can be configured to accommodate one, two, three, four, five, six or more air-sealed trocars.

In accordance with the invention, insufflation gasses, such as carbon dioxide gas can be fed into the systems on the suction side (prior to entering a pump), or on a supply side (after leaving the pump), or by way of a separate channel. Configuring the subject systems to take up replacement fluid on the suction side, allows for better control of the fluid, as the pumps can be configured to deliver a relatively constant flow. On the other hand, if fluid is injected at irregular intervals on the supply side of the pump, prior to being sent to the trocar(s) but after the pump(s), pressure in the supply side of the system, and thus in the patient, may fluctuate undesirably. Because systems in accordance with the invention are to a degree "open" systems, uptake of supply fluid on a suction side of the pump(s) can be offset by a reduced amount of ambient air or abdominal air taken up by the system through the trocar(s).

Figure 32:
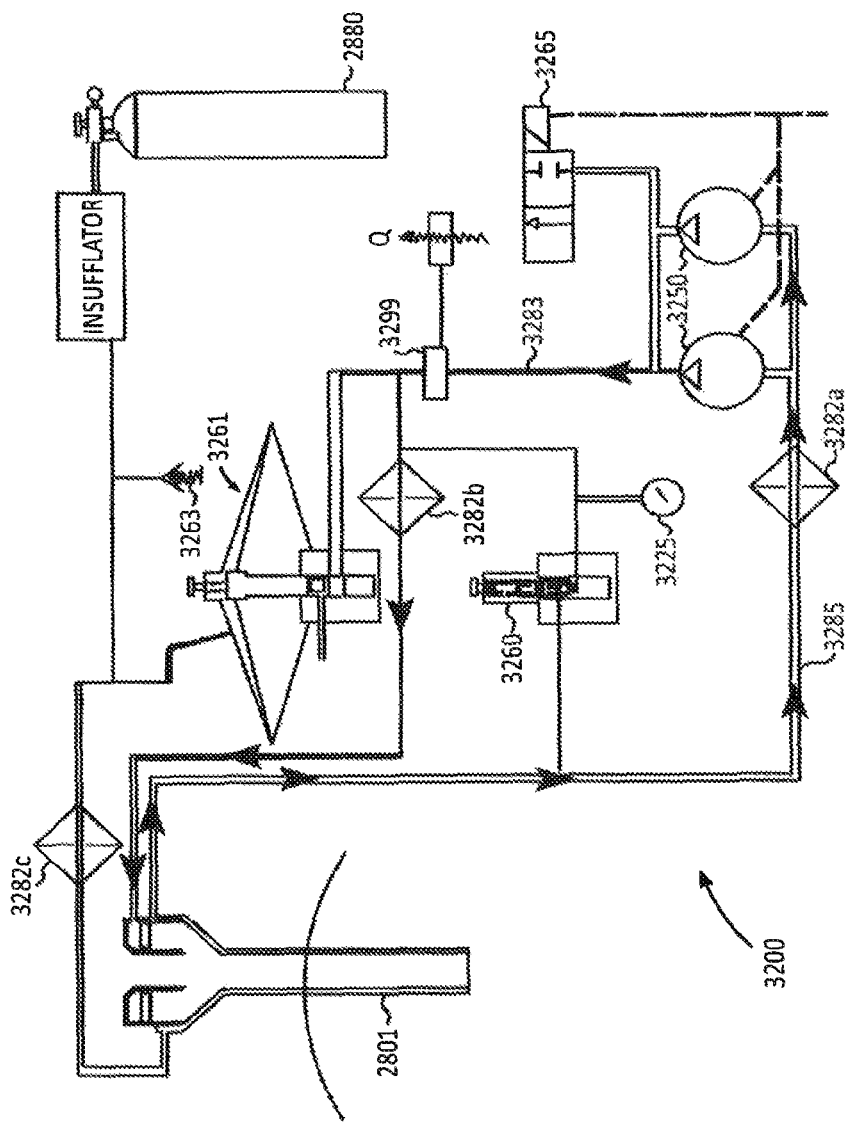
FIG. 32 is a schematic view of a recirculation system in accordance with the invention including a plurality of fluid pumps, a heat exchanger, a plurality of pressure relief valves and filters, among other features.
Figure 33A:
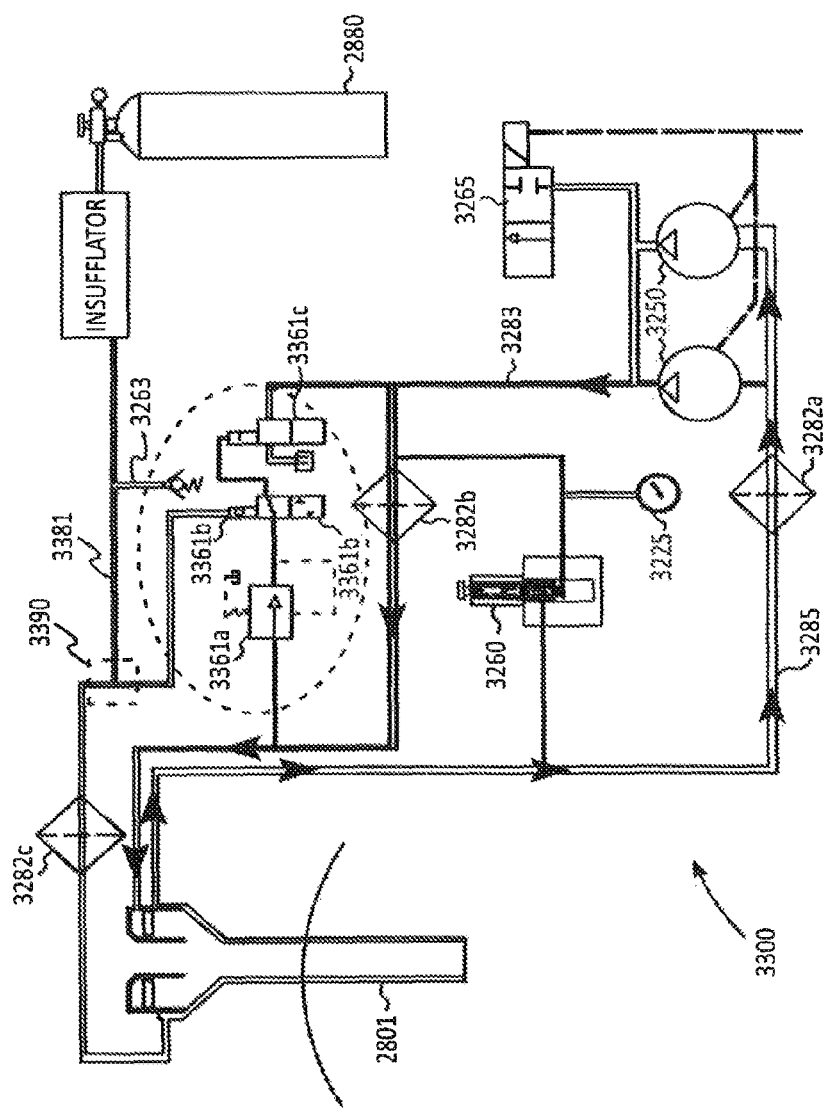
FIG. 33a is a schematic view of a recirculation system in accordance with the invention including a plurality of fluid pumps, an alternate pressure sensing arrangement using a venturi device, and a plurality of pressure relief valves, wherein at least one of such valves is electromechanical in nature.
Figure 33B:
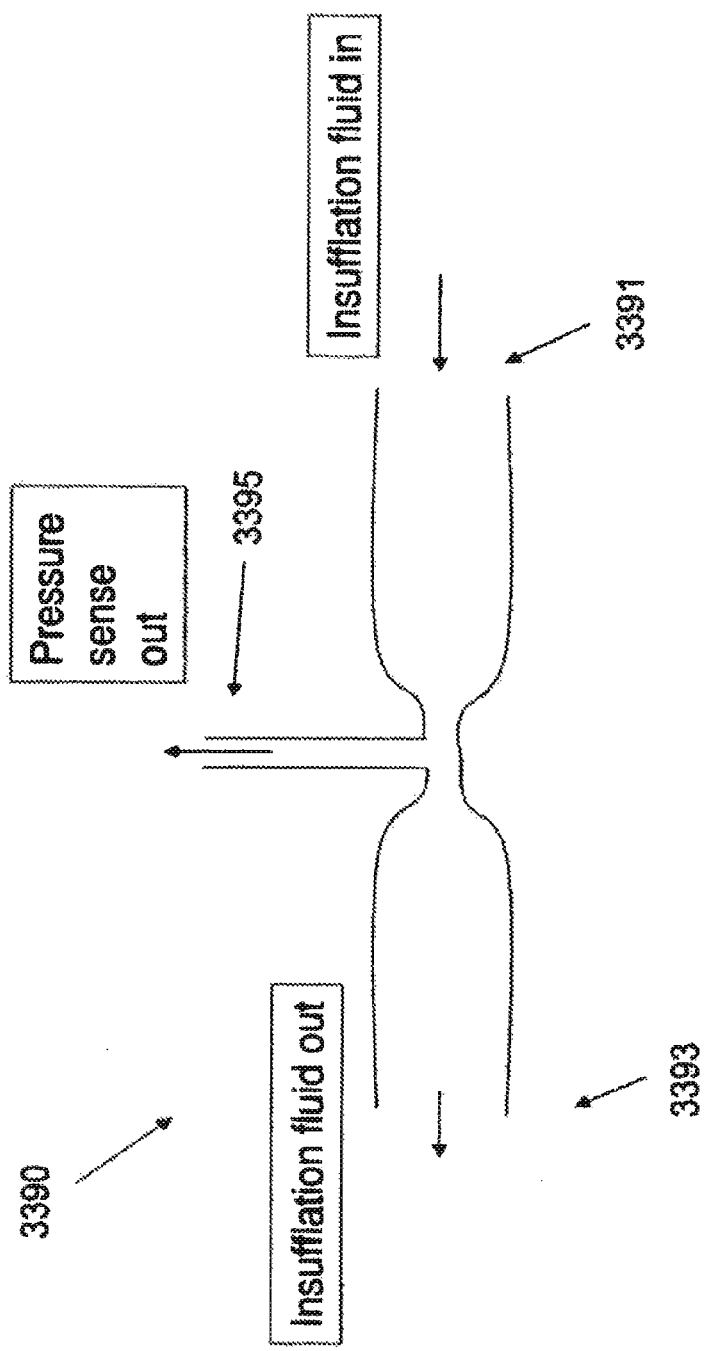
FIG. 33b is an enlarged schematic of a venturi device for use in conjunction with the invention for providing accurate and continuous pressure readings within the subject systems.

FIGS. 32 and 33*a* and 33*b* illustrate respective systems 3200, 3300 that include, among other features, filter elements 3282*a*; 3282*b*; 3282*c* on each fluid conduit, and dual circulation pumps 3250 to circulate fluid through the respective system. In addition to providing redundancy, the plurality of pumps allow a larger volume of fluid to be circulated than a single pump of similar size. Further, such increased capacity is possible with a reduced weight, as compared with a single larger capacity circulation pump. Also, if sized correctly, the pumps need not operate at their capacity limits, which allows for improved efficiency and reduced noise.

One or more heat exchangers (e.g., 3299 in FIG. 32) can be provided in connection with the respective systems to help condition the fluid being recirculated so that, for example, very cold or very warm fluid is not returned to the patient. Likewise, humidification and/or dehumidification elements can be included in the subject systems to condition air upon return from a patient or prior to supply to the patient. In accordance with one aspect of the invention, a heat exchanger 3299 is provided in connection with the system 3200 shown in FIG. 32, on the supply conduit 3283, leading from the recirculation pumps 3250. In accordance with this aspect, a heat exchanger can be provided within and/or around the supply conduit 3283 to reduce the temperature of pressurized fluid, upon exiting the recirculation pumps 3250. This is particularly advantageous with increasing pressures, due to the compression and maintenance of high pressures until reaching the trocar 2801, where the fluid is eventually depressurized and recirculated. Although some amount of heat from compression would be lost prior to reaching the trocar 2801, a reduction in temperature soon after compression may be desirable.

The heat exchanger can be embodied as a jacket around the supply conduit 3283, utilizing a heat conductive material such as copper or aluminum, for example. The heat can be carried through a portion of the heat exchanger by way of conduction, or alternatively by way of an active or passive thermodynamic circuit, such as one employing heat pipes, to carry heat away from the supply conduit 3283, which can then be transferred to the surrounding environment in a suitable manner, which can include radiative, conductive and/or convective heat transfer, which can be aided by way of a fan, for example.

If desired, the heat exchanger 3299 can include elements within the flow path of fluid passing through the supply conduit 3283, such as fins, to increase the area through which heat transfer can occur. Applicants conceive that the foregoing feature can also be provided in connection with any other embodiment described herein.

As illustrated in FIG. 32, a bypass or "back pressure" control valve 3260 can be provided to dump supply fluid to a return, in cases of excess pressure. The valve is illustrated as being an adjustable mechanical valve, but can be provided at a set pressure threshold, and/or as an electromechanical valve in connection with compatible pressure sensor. A gauge 3225 is optionally provided in connection with the system 3200, and can be mounted on the face of a housing, and can be mechanical or electronic in nature, in which case a pressure sensor/sender can be provided in direct fluid contact with the internal fluid conduits of the system 3200.

Additionally, separate dump valves can be provided in systems of the invention. Such valves can be provided for safety purposes, to reduce risk of over pressure scenarios. As set forth above, a bypass valve 3260 can reduce fluid volume provided to the trocar 2801. A further insufflation relief valve 3263 can be provided in connection with the insufflation supply, to quickly relieve excess pressure in case of operator error, such as a severe occluding of the respective fluid conduit on the trocar 2801 or malfunction of the system, for example. The insufflation relief valve 3263 can embodied as a simple fixed mechanical relief valve, or alternatively as an adjustable relief valve. In either case, an equivalent electro-mechanical valve can be substituted therefor, if desired.

As with foregoing embodiments, a diaphragm valve 3261 or alternatively an equivalent mechanical or electromechanical valve can be provided, but instead of being used to dump fluid to a recirculation pathway (i.e., the return conduit 3285), the fluid is released from the system, 3200 in response to cases of overpressure. Again, this valve 3261 can be embodied with an adjustable or a fixed pressure threshold.

As illustrated in the system 3200 of FIG. 32, a supply-side pressure relief valve 3265 can be provided in connection with the high-pressure side of the fluid pumps 3250, to reduce pressure within the supply conduit 3283 and connected components and conduits when the system 3200 is switched off. This may be desirable because when the pumps 3250 cease operation, fluid is not drawn through the return line 3285 from the trocar 2801, but the supply conduit 3283 and associated components still contain pressurized fluid. As illustrated, the supply-side pressure relief valve 3265 is a normally open electromechanical valve, allowing pressure to escape from the system 3200. When energized, the valve 3265 closes to prevent pressure loss. As illustrated, the valve 3265 is energized when the pumps 3250 are energized, and therefore can simply be connected electrically in parallel therewith. Alternatively, the valve 3265 can be controlled separately by an electronic controller to allow the pumps 3250 to continue removal of fluid, such as insufflation gasses that may include smoke or other debris, without reintroducing that fluid to the system 3200. Alternatively still, the pumps 3250 can be configured to reverse direction when an off-signal is received to equalize pressure in the supply 3283 and return 3285 conduits. Alternatively or additionally, the supply-side pressure relief valve 3265 in connection with the pump(s) 3250 can be adapted and configured to actively control output pressure across a range of selectable pressures, by reliving a portion or even all fluid during normal operation, in response to the commanded output pressure.

In accordance with the invention, any of the foregoing valves can be either mechanical or electromechanical in nature, as can the portions thereof, or the related components, which are capable of sensing pressure.

As shown, FIG. 33a illustrates a system 3300 that is similar to the system 3200 of FIG. 32, with the exception that the mechanical diaphragm valve 3261, which is configured to respond to a change in abdominal pressure, is replaced by a valve and sensor arrangement 3361. The valve and sensor arrangement 3361 can be adapted to act proportionately to actively control pressure to the trocar(s) and/or as a dump valve in cases of sudden overpressure. As illustrated, the valve and sensor arrangement 3361 is a hybrid electro-mechanical and pneumatically operated subsystem. A pressure regulator 3361a is in fluid communication with the supply conduit 3283, and regulates pressure from that conduit, passing the reduced pressure fluid to a pilot valve 3361b, which receives a pressure signal from a pressure sense/insufflation conduit 3381, which is in fluid communication with the abdominal cavity of the patient. When the pressure in the abdominal cavity, as measured through the pressure sense/insufflation conduit 3381 exceeds a set value, the pilot valve 3361b responds by passing the reduced pressure fluid from the pressure regulator 3361a to a dump valve 3361c. As illustrated the dump valve 3361c releases fluid from the supply conduit 3283 out of the system. However the dump valve 3361c can alternatively be passed to the return conduit 3285. Alternatively still, depending on the magnitude of the pressure above the set pressure of the pilot valve 3361b, the valve and sensor arrangement 3361 can first pass fluid to the return conduit 3285, and then if the pressure still exceeds a desirable limit, can release fluid from the system to the surrounding environment.

Further, the system 3300 of FIG. 33a can be provided with a venturi device 3390 through which fluid from the insufflator is provided to the trocar 2801. Although this feature can be applied to any embodiment set forth herein, as well as to any insufflator in the art, for simplicity it is described only in connection with FIG. 33a. As known, standard insufflators alternately pulse pressurized insufflation fluid, with pressure readings being taken during rest intervals, which are necessary to take relatively accurate readings, because taking readings during insufflation would yield inaccurately high results for abdominal pressures.

In accordance with the invention, an inlet port 3391 is the insufflation input received from the insufflator (or similar device). An outlet port 3393 is the output of the insufflation fluid to the trocar 2801. A pressure sensing port 3395 is the pressure sense conduit which is connected to the pressure sense components, such as the pilot valve 3361b of the system 3300 of FIG. 33a, for example. Applicants recognize that placement of a venturi-type device into a subject system, as shown, allows fluid communication between all devices as described above, but reduces or eliminates the fluctuation of measured pressure within the system normally caused by the relatively high intermittent pressure pulsations provided by the insufflator. With consistent and accurate pressure measurements, a single conduit can be utilized to both provide continuous insufflation gas as needed and to simultaneously, continuously measure abdominal pressure.

Accordingly, the placement of such a venturi 3390 can enable constant insufflation, rather than simply periodic insufflation available commercially today, and the concept and device can be easily applied to otherwise standard surgical insufflators.

It is further conceived, in accordance with the invention, that the systems and devices described herein can be used for the purpose of smoke evacuation. The subject systems can be used as illustrated, and can filter particulate matter from recirculated air, thereby continuously cleaning the air within the abdominal cavity and allowing a clear view of the operative space.

If desired, nozzles and the associated supporting componentry can be provided on one or more trocars as described hereinabove, e.g. trocar 2801, while return insufflation fluid is collected through a second device at a location spaced therefrom, to improve flow and better flush the operative site of smoke and/or other debris. Devices that can be used to collect return fluid can include one or more trocars constructed in accordance with the invention (e.g., trocar 2801), or alternatively a conventional trocar, veress needle or the like.

In accordance with an another aspect, the subject systems can be connected to more conventional access devices, with fluid being supplied through an insufflation port or main lumen thereof. Also, fluid can be supplied through one device and collected at another device to effectively filter the insufflation gas.

In alternative embodiments, fluid can be supplied to one conduit of a specialized access device, while fluid is returned by way of a second conduit associated with the access device, or vice versa. For example, if utilized with trocars in accordance with the invention, if the pressure sense/insufflation channel provided in the subject trocars is sized sufficiently large, fluid can be supplied or returned through such channel, with the other function being performed through another channel, such one or more of the recirculation chamber and the fluid supply chamber and the associated components.

Optionally, the function of fluid supply or removal for smoke evacuation can be effected by way of a separate tube inserted through a lumen of an access device, such as trocar 2801. Alternatively still, fluid supply and or fluid return functions can be incorporated into a separate surgical tool, that can be inserted through the lumen of an access device, such as trocar 2801 or a more conventional access device, as needed. If desired, such tool can remain in the lumen of the access device during a procedure.

If so-desired, systems in accordance with the invention can be adapted to recirculate and filter particulate matter without providing any net change in abdominal pressure or volume. In such instances, the insufflation componentry can be provided but temporarily disabled, while alternative insufflation device is used to insufflate the abdominal cavity, for example.

Advantageously, however, the subject systems and related devices, such as trocar 2801, for example, while being used to provide a fluid seal for unencumbered access to the pneumoperitoneum inherently allow for exchange of gasses and recirculation thereof, which inherently provides continuous cleansing by filtration of insufflation gases. However, the subject systems can be used as an adjunct to more conventional surgical systems to provide the function of smoke evacuation.

Figure 34:
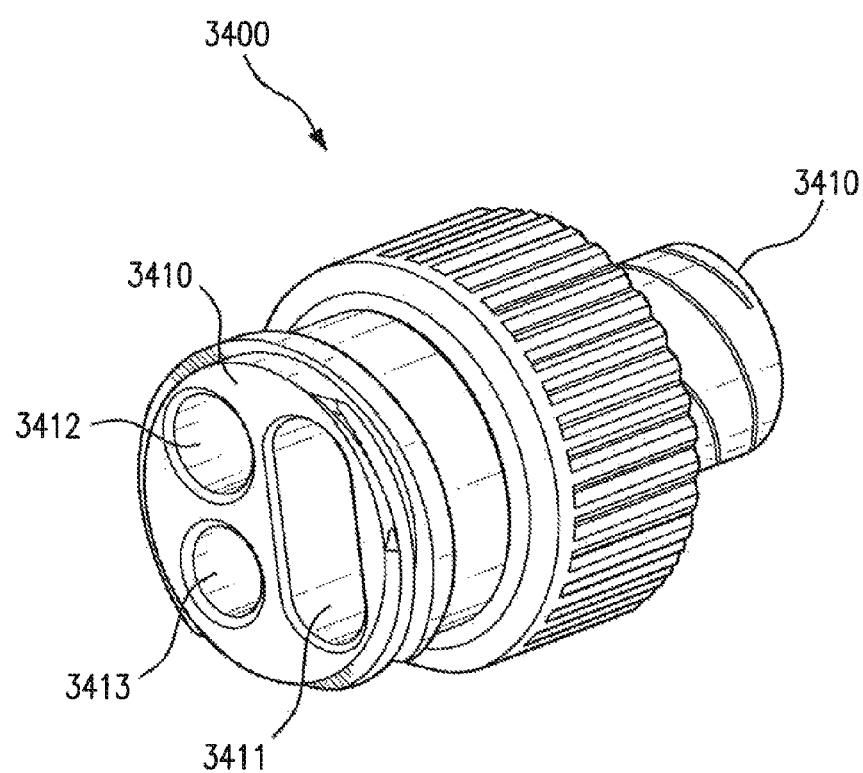
FIG. 34 is an isometric view of an adapter in accordance with the invention for adapting a multi-lumen tube set for use with systems according to the invention for use with a single lumen standard insufflation device, such as a veress needle or standard insufflation trocar.
Figure 35:
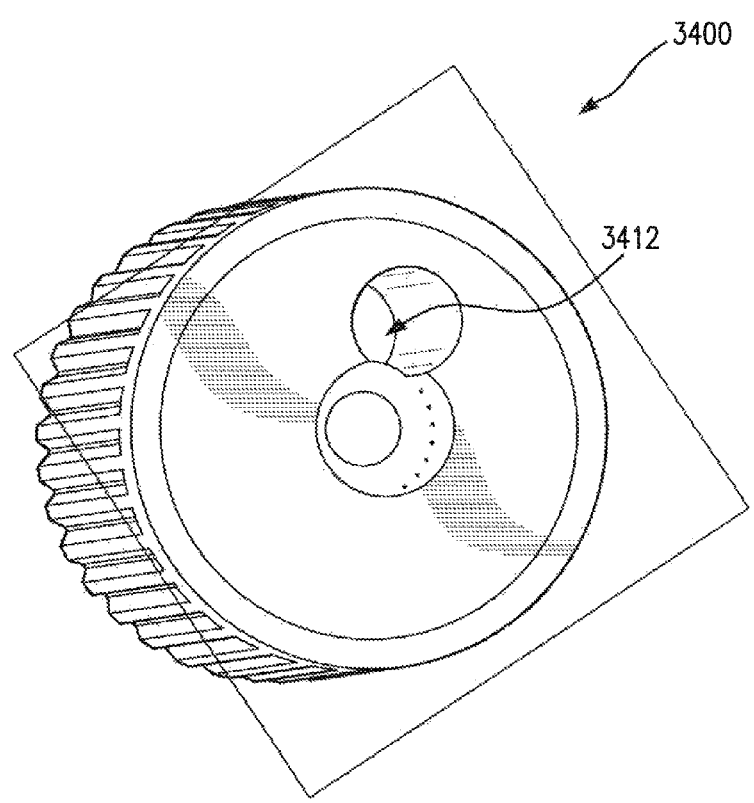
FIG. 35 is a cross-sectional view of the adapter of FIG. 34 showing an internal passageway.

FIGS. 34 and 35 illustrate an adapter 3400 for adapting a multi-lumen tube set for use in connection with the subject systems and devices (e.g., trocar 2801) for use with a standard insufflation needle, standard insufflation trocar or the like. The adapter 3400 includes a multi-lumen portion 3410 for connection with a tube set of the invention, which multi-lumen portion 3410 is similar to and compatible with the connector portion (e.g. 2310 in FIG. 23) of trocars of the invention. The adapter 3400 also includes a single lumen portion 3420 for connection to a standard insufflation needle (e.g. veress needle), standard insufflation trocar or other device. The single lumen portion 3420 can be adapted with the necessary connection features to connect with the standard insufflation devices, such as a standard luer fitting with a central lumen and threaded engaging portion. As best shown in FIG. 35, which is a cross-section of the adapter 3400, an internal channel connects an insufflation lumen 3412 from its axial offset position in the multi lumen portion 3410 to a central position in the single lumen portion 3420, and in this manner allows the subject systems to pass insufflation fluid, and thus the insufflator functionality therethrough. The fluid supply lumen 3413 and recirculation return lumen 3411 (FIG. 34) are provided as terminations, but alternatively can be connected to one another in the adapter 3400, bypassing the patient. If terminated as illustrated, the subject systems can bypass fluid supply and return functions through internal bypasses, as described above. However, the adapter 3400 with standard insufflation needle, standard insufflation trocar or other device can be used in parallel with a surgical access device or "trocar" in accordance with the invention, such as trocar 2801.

In use, an initial puncture and insufflation can be performed with use of a device, such as a veress needle, connected through the adapter 340,0 to a system in accordance with the invention. When the desired abdominal pressure is reached, one or more access devices can then be inserted into the patient and connected to a system in accordance with the invention.

FIGS. 36-63 illustrate an embodiment of a surgical access device 3600 designed in accordance with the invention, related components thereof showing alternatives, as well as an insertion device 3890 (FIGS. 38-42).

Figure 36:
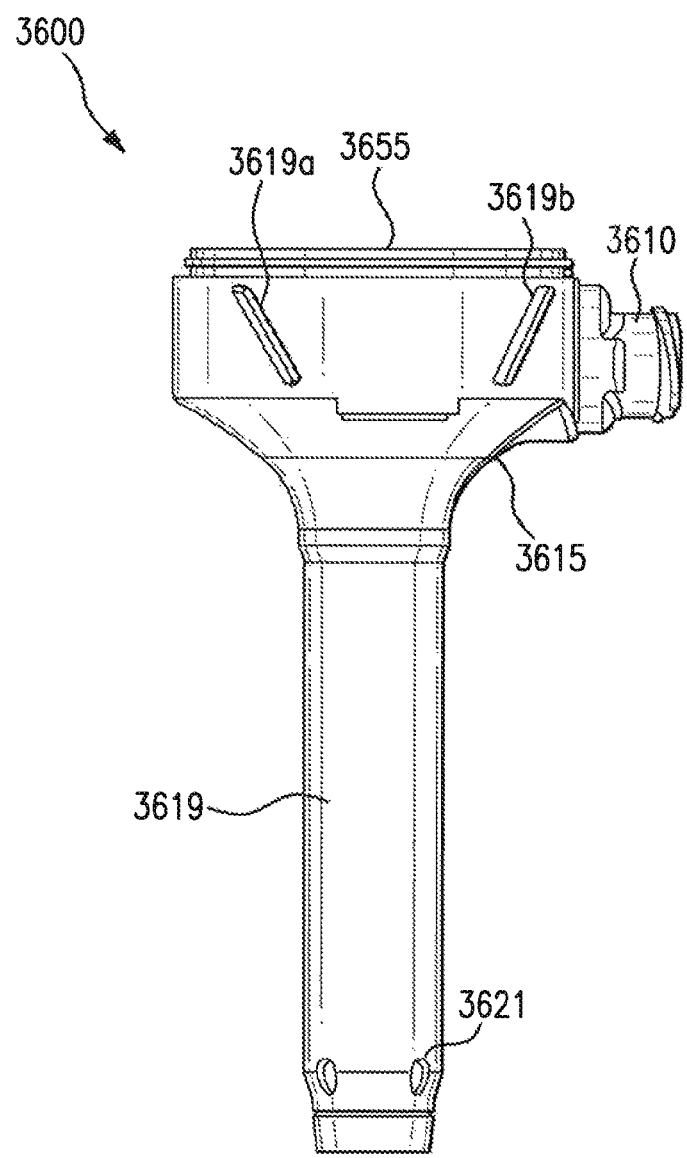
FIG. 36 is a side view of a surgical access device in accordance with the invention.
Figure 37:
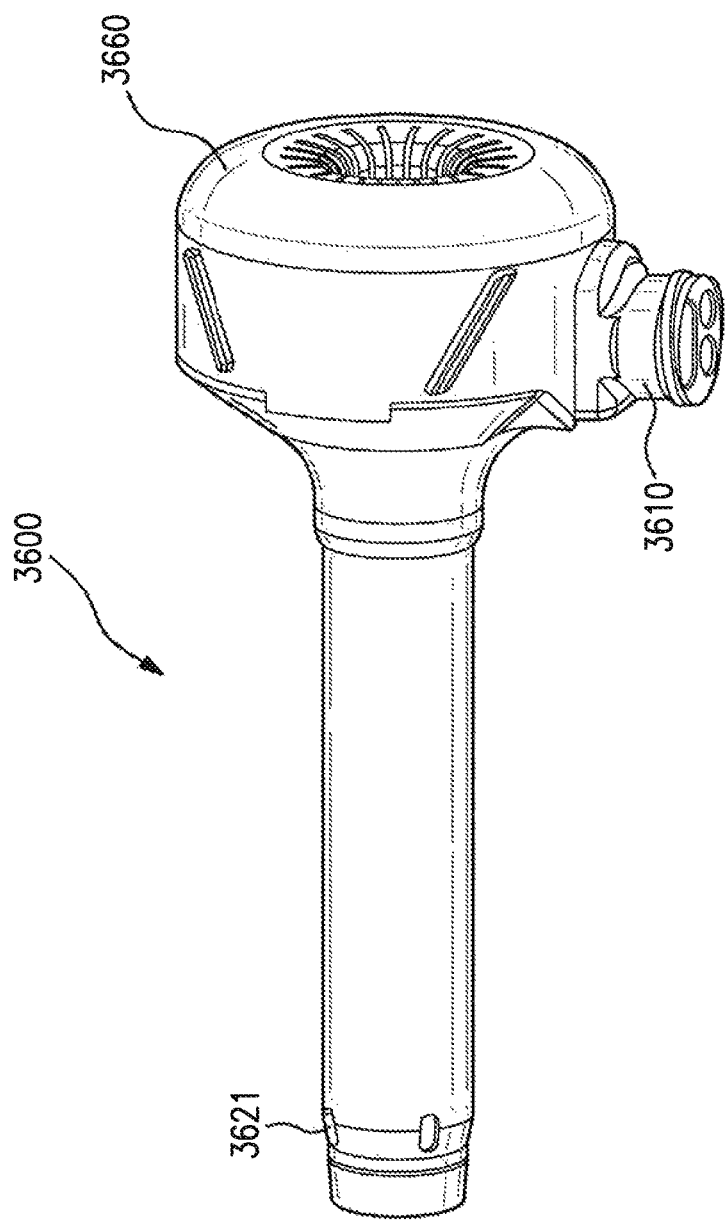
FIG. 37 is an opposite side view of the surgical access device of FIG. 36, with a proximal cap provided thereon.
Figure 38:
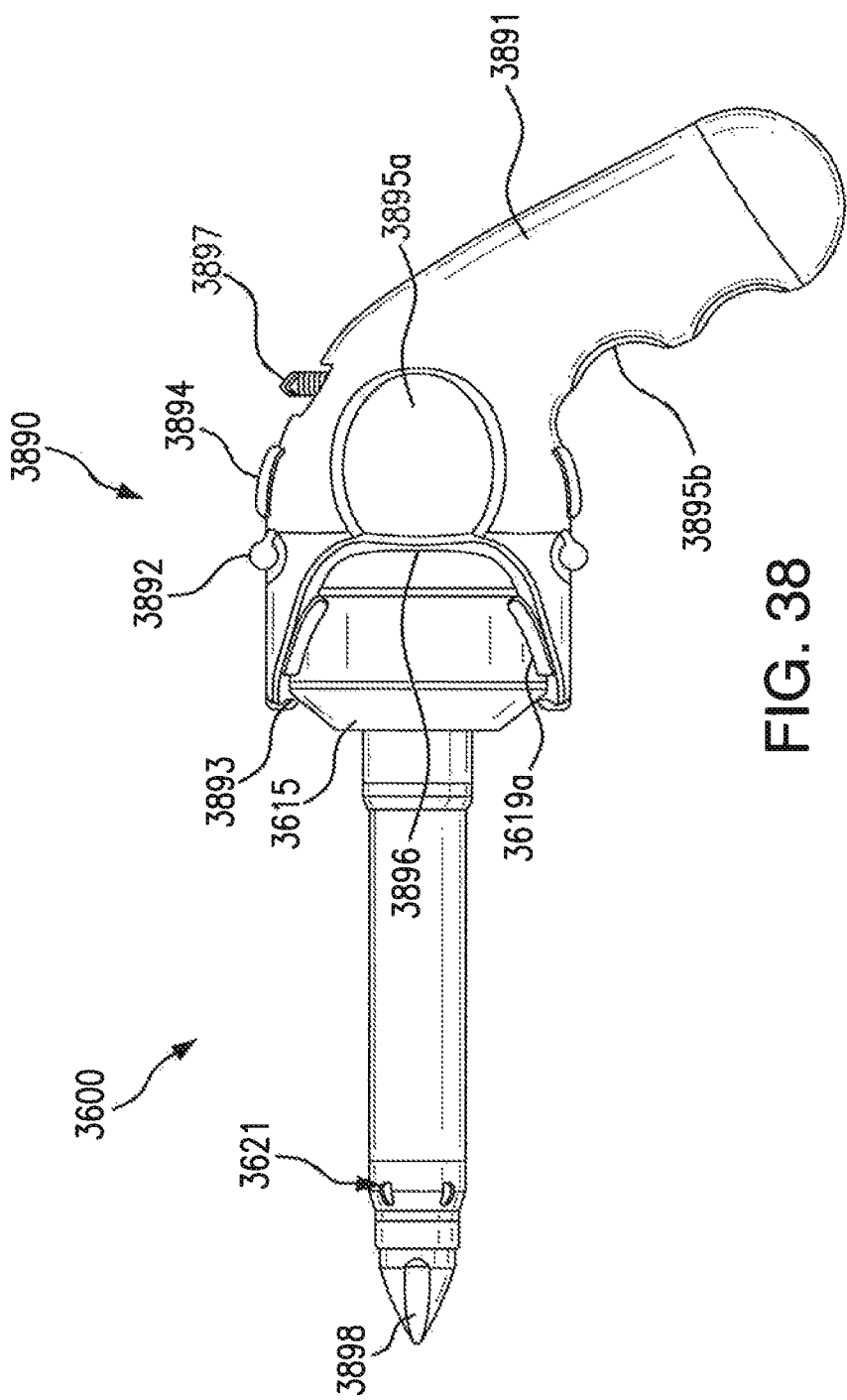
FIG. 38 is a side view of the surgical access device of FIGS. 35 and 36, with a cap provided thereon, assembled with an insertion device for insertion into a patient.

FIGS. 36 and 37 illustrate opposite faces of the surgical access device 3600, which, among other aspects, is adapted and configured to create a fluidic seal, or in other words, a pressure barrier, between the abdominal cavity and the surrounding environment, as described herein above, and below. The access device 3600 includes, among other components, a proximal housing 3615, a connector 3610 for engaging a tube set for use therewith, and an outer body tube 3619. The proximal portion of the housing 3615 includes threads 3665 for connection with an end cap, such as end cap 3660, with additional examples shown in subsequent drawings and discussed below. The housing 3615 includes alignment elements 3619a, 3619b, which engage corresponding portions on the insertion device 3890 (FIGS. 38-42). As illustrated in FIGS. 36 and 37, two pairs of alignment elements 3619a, 3619b are provided on opposite portions of the housing 3615, although variations thereof are possible. The angled orientation of the alignment elements 3619a, 3619b is such that the mating portion of the insertion device 3890 is gradually guided into alignment as the access device 3600 and insertion device 3890 are connected.

Figure 39:
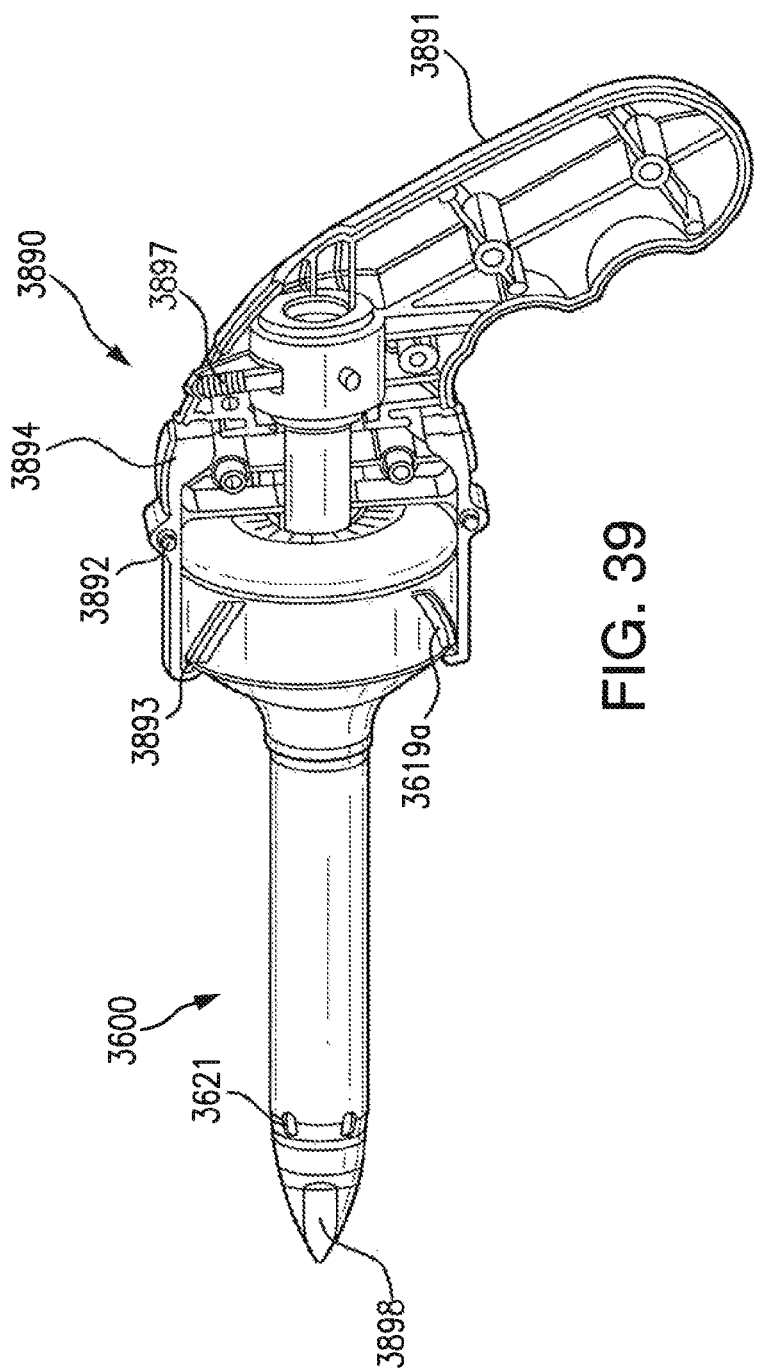
FIG. 39 is a partial cutaway view of the insertion device of FIG. 38, in the assembly of FIG. 38.
Figure 40:
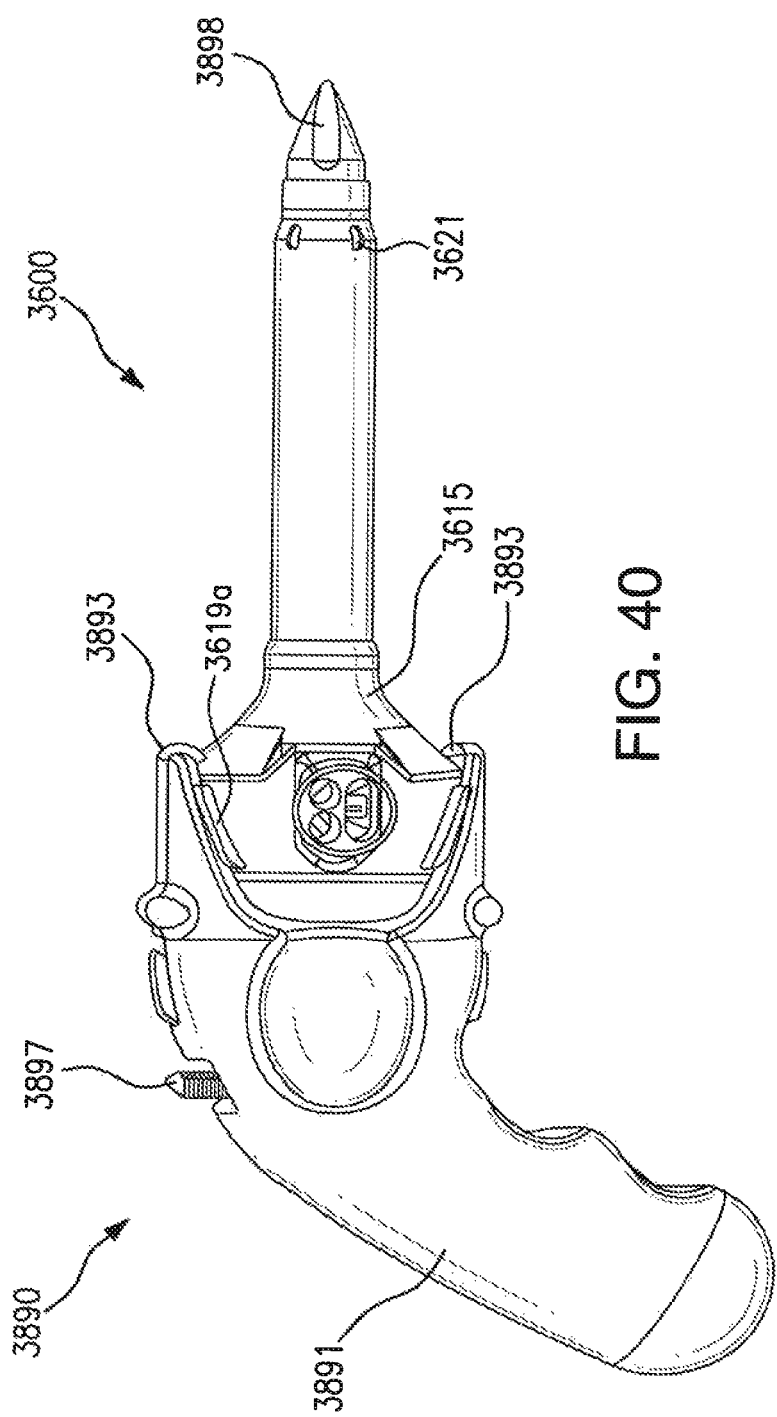
FIG. 40 is an opposite side view from FIG. 38 of the assembly of FIG. 38.

As illustrated in FIG. 38-42, the insertion device 3890 includes a penetration tip 3898, attached by a shaft 3999 (FIG. 39) to a handle portion 3891. A grip 3895b and indentations 3895a are included on the handle 3891 to facilitate holding by the surgeon. The surgeon's first finger and thumb rest in the indentations 3895a provided on each side of the handle 3891, with the second and third fingers resting on the grip 3895b, for example. The distal end portion of the handle 3891 (toward the left in FIG. 38) includes shaped openings 3896, provided symmetrically on each side of the handle. As shown in FIG. 40, the shaped openings 3896 allow the connection element to sit more proximally (toward the handle 3891), reducing the overall profile of the combined assembly of the access device 3600 and insertion device 3800. The shaped openings 3896 also permit the use of the angled alignment elements 3619a, 3619b that guide the proper mutual alignment between the access device 3600 and insertion device 3890. The alignment elements 3619a, 3619b and mating portion of the handle 3890, in accordance with a preferred aspect, are sized, spaced and/or shaped to permit only proper relative orientation of the access device 3600 and insertion device 3890.

As illustrated, the insertion device 3890 includes dual opposed engagement catches 3894, which have pawls 3893 on their distal ends, and pivots 3892 in the middle portions thereof. The pawls 3893 engage a lower portion of the housing 3615 or other mating surface, depending on the precise implementation. A scope or instrument lock 3897 can also be provided for engaging a device such as an endoscope, for use in conjunction with the insertion device 3890. Alternate features can be provided, as set forth in U.S. Patent Publication Numbers 2008/0086080 to Mastri et al. and 2008/0086160 to Mastri et al., which are incorporated herein by reference in their entirety.

FIG. 39 illustrates a partial cutaway view of the insertion device 3890 shown with the access device 3600 engaged therewith. The shaft 3999 of the insertion device 3890 extends through a central lumen of the access device 3600, terminating in the penetrating tip 3898. The pawls 3893 of the catches 3894, which are mounted on pivots 3892 are seen engaging the access device 3600. The outer surface of the scope or instrument lock 3897 is also illustrated.

Figure 41:
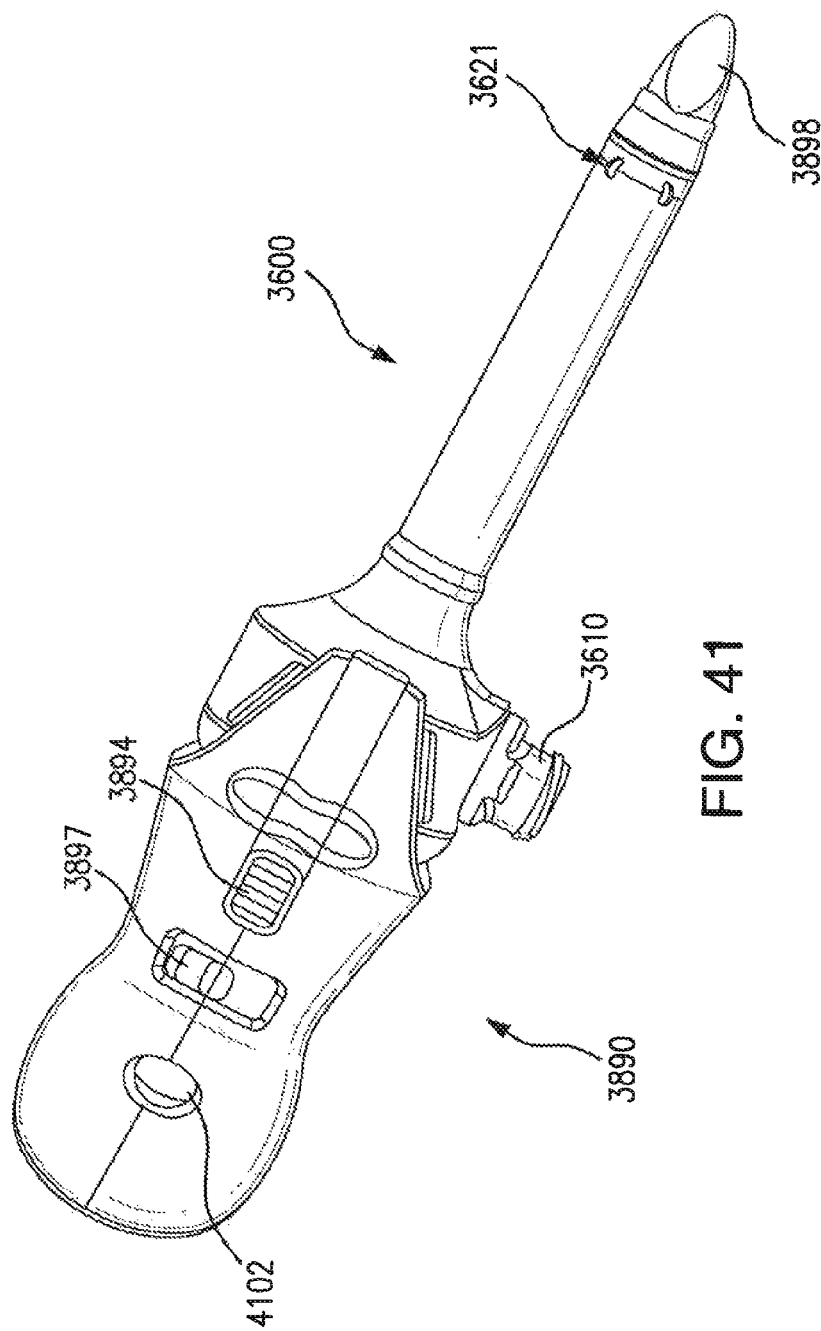
FIG. 41 is a top view of the assembly of FIG. 38.
Figure 42:
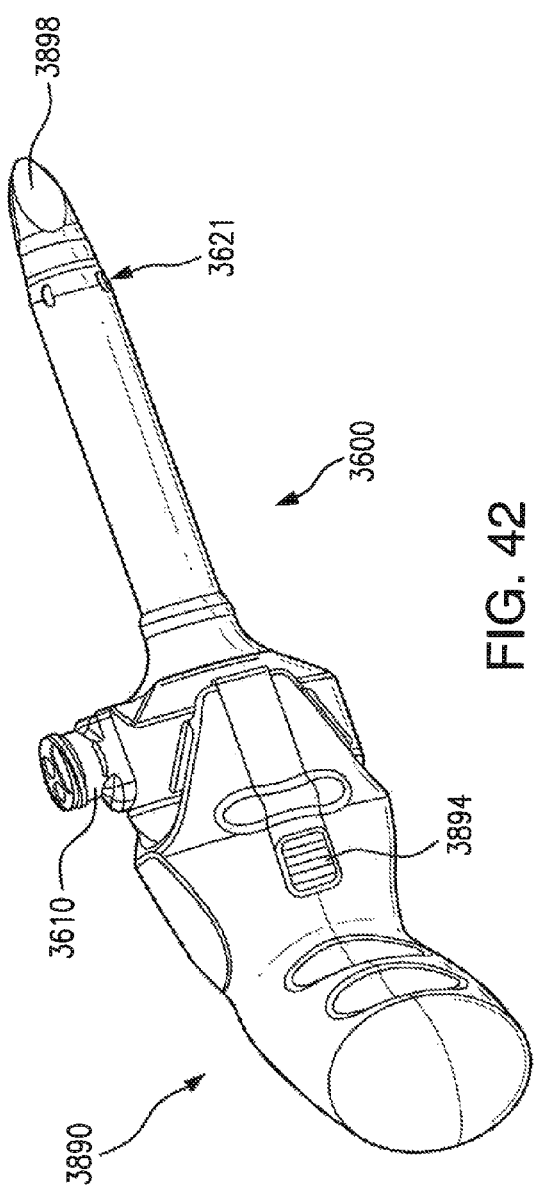
FIG. 42 is a bottom view of the assembly of FIG. 38.

FIGS. 41 and 42 respectively illustrate top and bottom views of the access device 3600 in connection with the insertion device 3890. As best seen in FIG. 41, the handle of the insertion device 3890 includes an aperture 4102 formed therein, which allows an endoscope or other instrument to pass therethrough, which can be engaged by the lock 3897.

FIGS. 43-63 illustrate various aspects and alternatives for the trocar 3600 in accordance with the invention.

Figure 43:
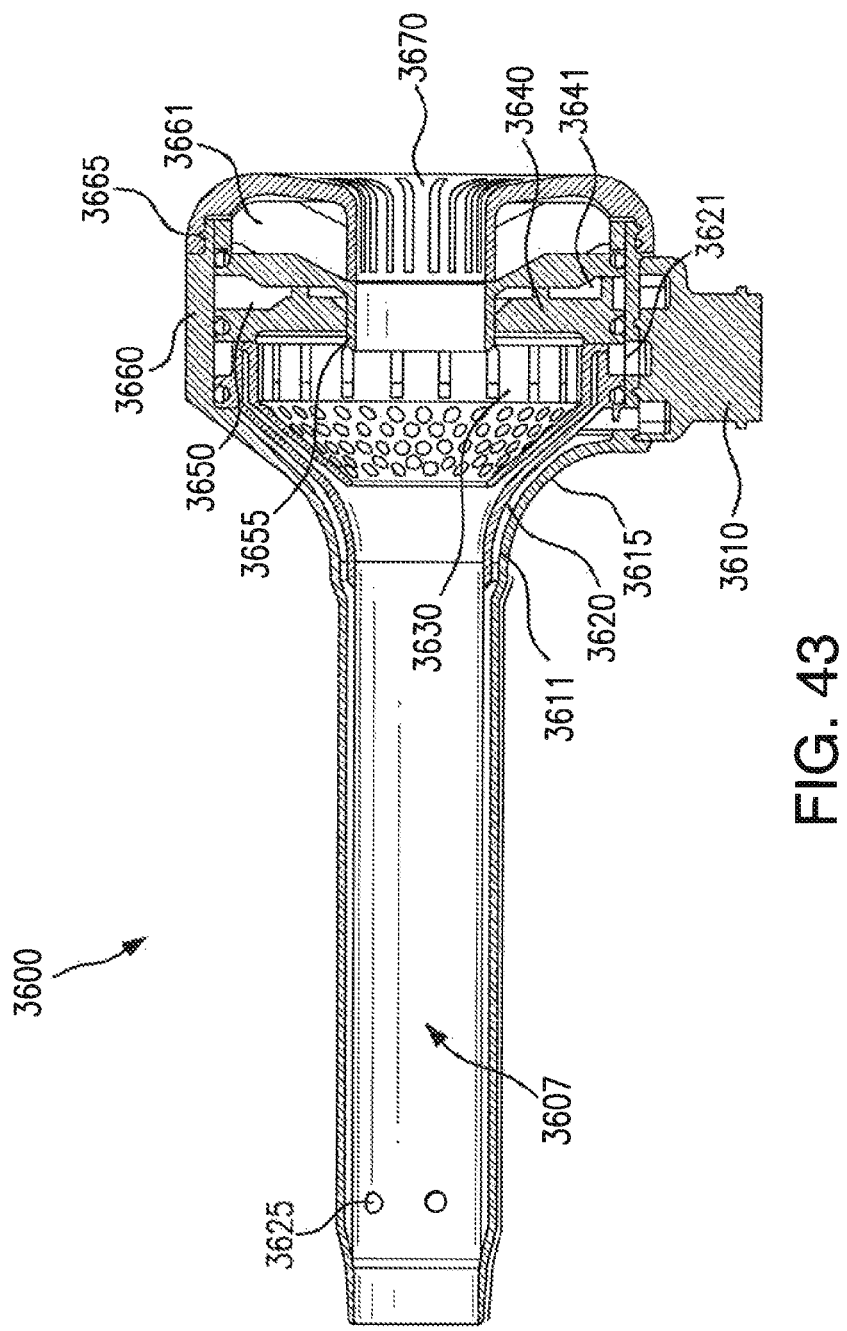
FIG. 43 is a cross-sectional view of the surgical access device of FIG. 36.

As shown in FIGS. 43-45, the trocar 3600 includes a body having a housing 3615 arranged at the proximal end portion thereof. An annular insert 3640 and a nozzle insert 3650 define, in conjunction, a nozzle 3655 and a fluid supply plenum 3641. A fluid return plenum 3621 is defined between two inserts 3620 and 3630. The upper insert 3630 includes a plurality of apertures 3631, 3633 defined therein, which allow the upper insert 3630 to guide instruments inserted therethrough while effectively raising the location proximally at which fluid is taken in by the return plenum 3621. The configuration and placement of the apertures 3631, 3666, therefore, can be adjusted as needed to fine-tune the operational characteristics of the trocar 3600.

In the illustrated embodiment, the lower insert 3620 is substantially tubular and extends distally toward the end of the access device 3600, and in part defines, with the housing 3615, an insufflation and/or pressure sense conduit 3611 for communicating the pressure of the abdominal cavity with the external system components. Seals, such as O-rings can be provided in respective detents to seal between the inserts and the housing 3615, to help seal respective chambers from one another.

The nozzle insert 3650 is formed so as to have a depressed region which helps accommodate a proximal sound attenuation chamber 3661, in cooperation with a proximal cap 3660. Sound absorbing material can be provided in the sound attenuation chamber 3661 to help reduce noise emitted by the flowing fluid within the trocar 3600. Openings 3670 are optionally provided in the cap 3660 to allow communication between the fluid in the lumen and any sound attenuation materials provided in the chamber 3661 to allow the material to absorb sound created in the lumen 3607 of the access device 3600. The cap 3660 then helps guide instrument insertion, while holding in and protecting the sound attenuating material, and help further absorb excess sound.

The cap 3660, as illustrated, is adapted to threadedly engage the housing 3615 by way of complimentary threads 3665 formed on the housing 3615 and cap 3660. When assembled, screwing the cap 3660 to the housing 3615 causes all inserts (3620, 3630, 3640, 3650) to be firmly held within the housing 3615, providing for simple assembly of the trocar 3600. Alternatively, the cap 3660 can be secured to the housing in a different manner, including but not limited to other mechanical connections, such as latches, snaps, friction fit, adhesives, welding, such as heat or friction welding, including spin-welding, for example.

The fluid return plenum 3621, fluid supply plenum 3641 and pressure sense and/or insufflation plenum 3611 are in fluid connection with respective conduits, which are connected through the connection boss 3610 provided on the housing 3615. The connection boss 3610, as described above, connects with a tube end connector, such as connector 2320 to connect the trocar 3600 with a compatible system to facilitate fluid supply to and removal from the trocar 3600.

As best seen in the enlarged view of FIG. 45, the insufflation and/or pressure sense conduit 3611 which is defined between the lower insert 3620 and the housing 3615 continues distally through the trocar 3600. As seen in FIGS. 36-42, for example, apertures 3623 are provided on the outer surface of the trocar 3600 in fluid communication with the insufflation and/or pressure sense conduit 3611, and as best seen in FIGS. 43 and 45, apertures 3625 can be provided in the inner wall of the trocar 3600, in communication with the lumen 3607 and the insufflation and/or pressure sense conduit 3611. Accordingly, with redundant apertures, any attached system or device has an improved chance of not receiving an inaccurate reading or being inhibited from proper function. In case an instrument inserted through the lumen 3607 partially or fully blocks the inner apertures 3625, the outer apertures 3623 are still available to conduct fluid and/or a pressure signal. Similarly, if the outer apertures 3623 are blocked by tissue, or other structures or objects in the abdominal cavity, the inner apertures 3625 are available.

Figure 46:
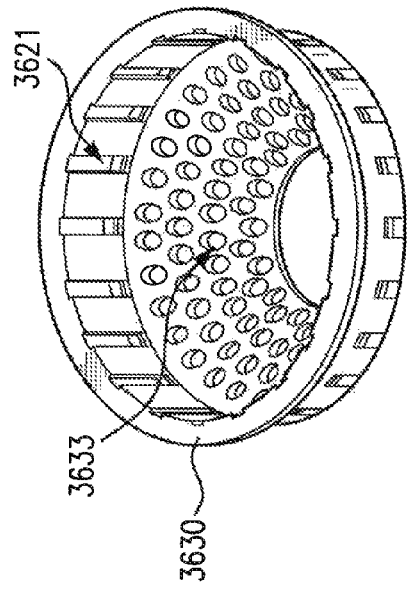
FIG. 46-51 are isometric views of various components of the trocar of FIG. 36.

FIG. 46 illustrates an upper portion 3620a of the lower insert 3620, embodied separate from a distal end portion 3620b (See FIG. 50) thereof. As illustrated, the upper portion 3620a includes apertures embodied as notches 4629, to allow passage of fluid collected in the recirculation plenum 3621 to pass through the insert 3620 and to the respective system for filtration, exhaust and/or recirculation, as desired.

Figure 47:
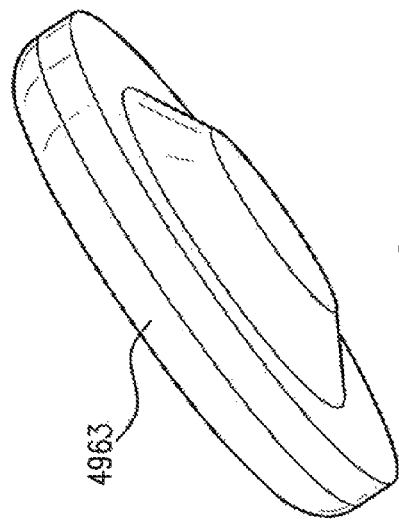
Figure 48:
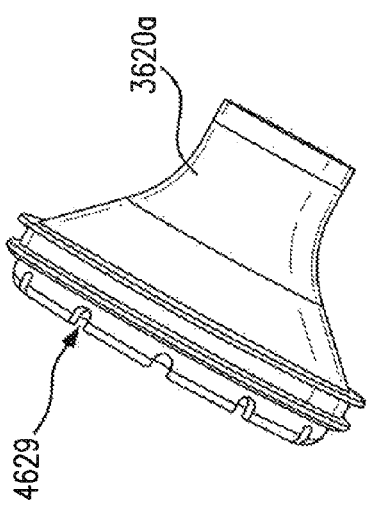
Figure 49:
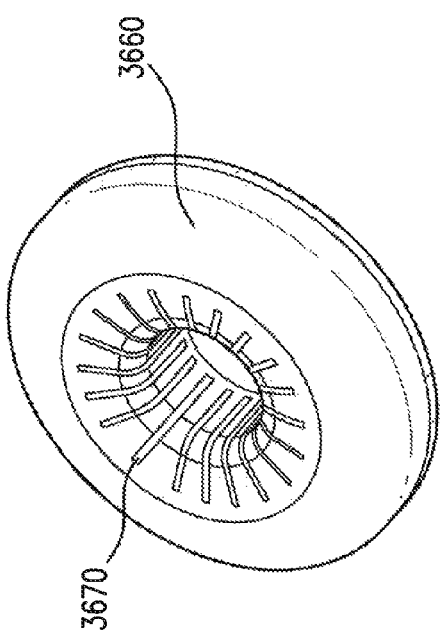

FIG. 47 is an isometric view of the upper insert 3630 shown alone, illustrating the various apertures 3631, 3633, as described above. FIG. 48 is an isometric view of the cap 3660 as described above, which includes apertures 3670 embodied as slits to facilitate absorption of at least a portion of sound generated by fluid flowing in the trocar 3600. FIG. 49 illustrates an insert 4963 formed of sound-absorbing material, for placement beneath the cap 3660, in the proximal sound attenuation chamber 3661 (FIGS. 43 and 44). The material can be any desired sound-absorbing material, including foams, and may be shaped as solid block, or shaped to enhance sound attenuation properties, which may include increasing surface area. Such shapes can include but are not limited to having a substantially honeycomb structure, undulating surfaces, a surface having conical protrusions, tubular passageways formed therethrough, or the like.

Figure 50:
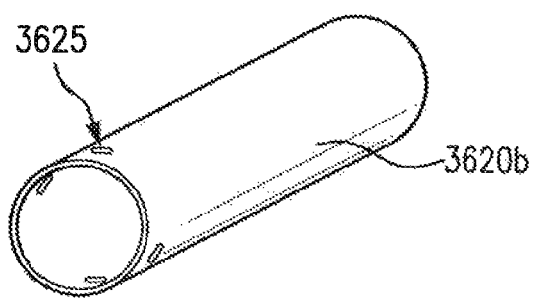

FIG. 50, as set forth above, illustrates the distal end portion 3620b of the lower insert 3620, wherein the proximal portion 3630a (See FIG. 46) is formed separately therefrom. As illustrated, internal apertures 3625 are formed in the distal end region of the distal end portion 3620b, for the reasons set forth above.

Figure 51:
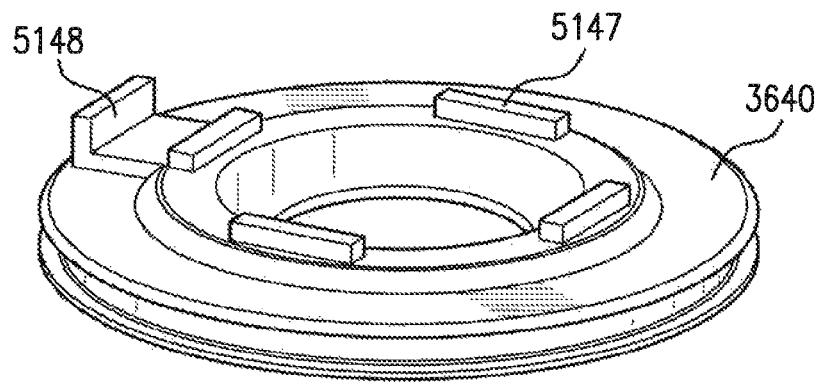

FIG. 51 illustrates the substantially annular insert 3640, which in combination with the nozzle insert 3650 (See FIG. 52, for example) forms nozzles 3655, through which pressurized fluid passes and is manipulated to form a fluidic seal or "barometric barrier," for preventing loss of pressurization of the abdominal cavity during a procedure, while allowing for a substantially physically unobstructed access path into the surgical cavity. The nozzle insert 3650, as illustrated, includes standoffs 5147 to help maintain spacing between the substantially annular insert 3640 and the nozzle insert 3650, arranged thereabove, as seen, for example, in FIGS. 43 and 44. The standoffs 5147 are spaced apart from one another to allow pressurized fluid to flow therethrough from the fluid supply plenum 3641, through the nozzle 3665. A diverter 5148 is also provided in the illustrated embodiment and is aligned with a pressurized fluid inlet to diffuse an incoming stream of fluid within the fluid supply plenum 3641, to more effectively distribute fluid flow about the plenum 3641, and thus through the nozzle 3665.

Figure 52A:
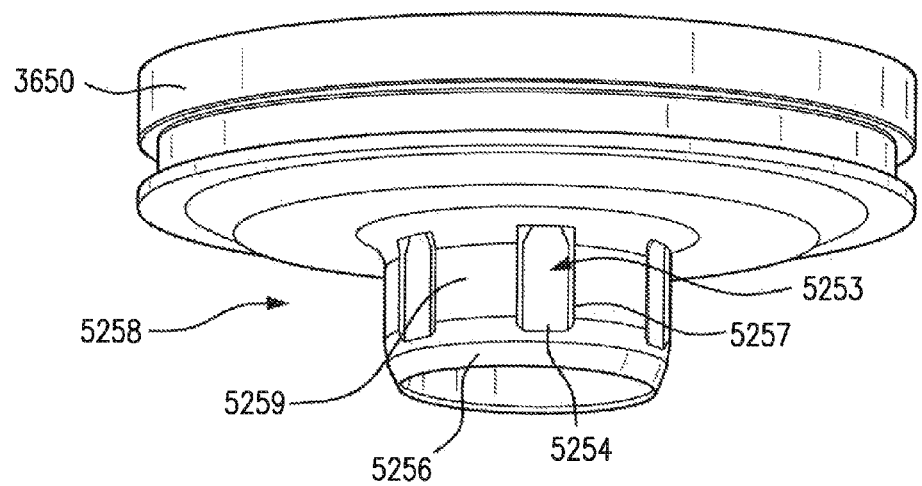
FIGS. 52a and 52b illustrate details of one nozzle arrangement for the subject surgical access devices.
Figure 52B:
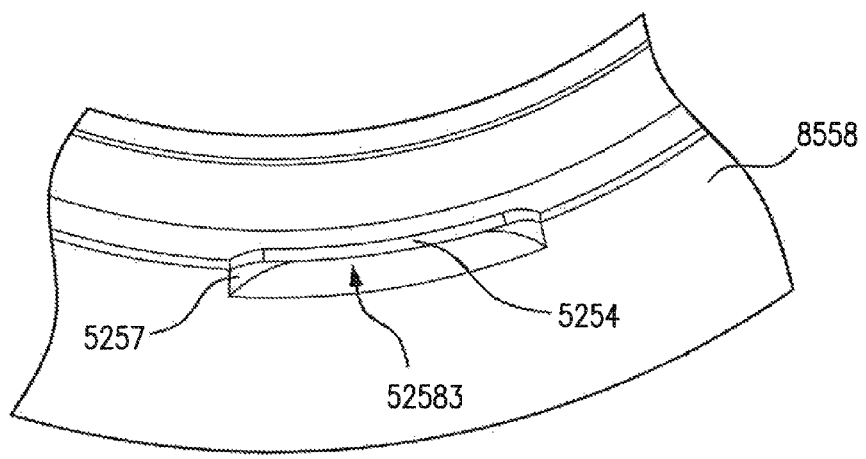
Figure 53:
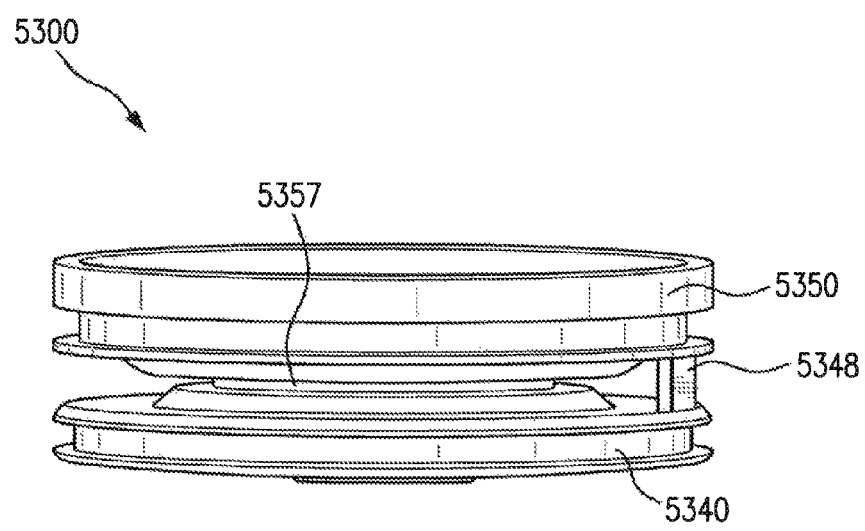
FIGS. 53-57 include various views and components for an alternate nozzle arrangement for the subject surgical access devices.

FIGS. 52a and 52b illustrate isometric and detail views, respectively, of a nozzle insert 3650 in accordance with the invention, in which radially spaced depressions 5253 are formed in the lower portion 5258 of the insert 3650 to define, in combination with the annular insert 3640, fluid passageways for the nozzle 3665. The depth of the depressions 5253 can solely determine the area through which fluid can pass if the annular insert 3640 and nozzle insert 3650 are provided in intimate contact, and fluid cannot pass between the insert 3640 and nozzle insert 3650, except through the depressions 5253. In accordance with one preferred embodiment, the depth of the depressions 5253 is about 3/1000 inch (about 0.0762 mm), however the precise depth can be adjusted as needed. Alternatively, spacers, including the above-mentioned standoffs 5147 help define the spacing between the annular insert 3640 and the nozzle insert 3650, and determine the width of a space between the insert 3640 and nozzle insert 3650, and therefore the area available for fluid to pass through the nozzle 3665.

The lower portion 5258 of the nozzle insert 3650 includes a substantially cylindrical outer portion 5259, in which the depressions 5253 are formed. As illustrated, six depressions 5253 are provided. The depressions 5253 include a bottom portion 5254 and side portions 5257. The bottom portion 5254 can be either substantially flat or arcuately curved, as shown in FIG. 52b. In the case of an arcuately curved bottom portion 5254, the radius of the curvature can be substantially the same as a radius of curvature of the substantially cylindrical outer portion 5259, but offset radially centrally, for example, forming the depressions 5253. The side portions 5257, then, are contoured so as not to promote turbulence or noise, and to facilitate substantially smooth flow of fluid from the fluid supply plenum 3641 through the depressions 5253 and the nozzle 3665. Fluid flow though the depressions 5253 and around the distal portion of the insert 3650 tend to behave in accordance with the Coanda effect, which directs the fluid stream inwardly, in accordance with the inward curvature of the distal tip portion 5256 of the insert 3650.

Figure 54:
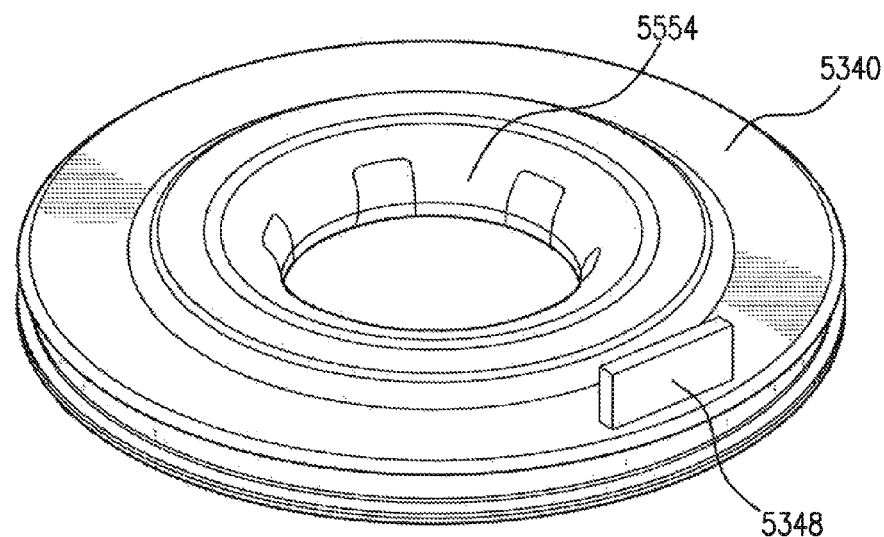
Figure 55:
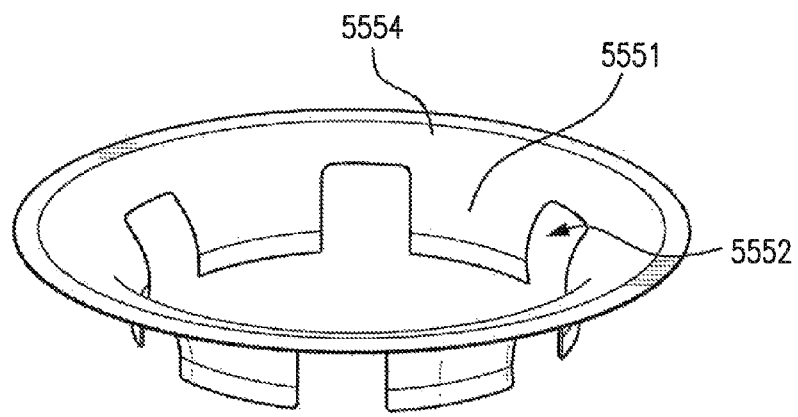
Figure 56:
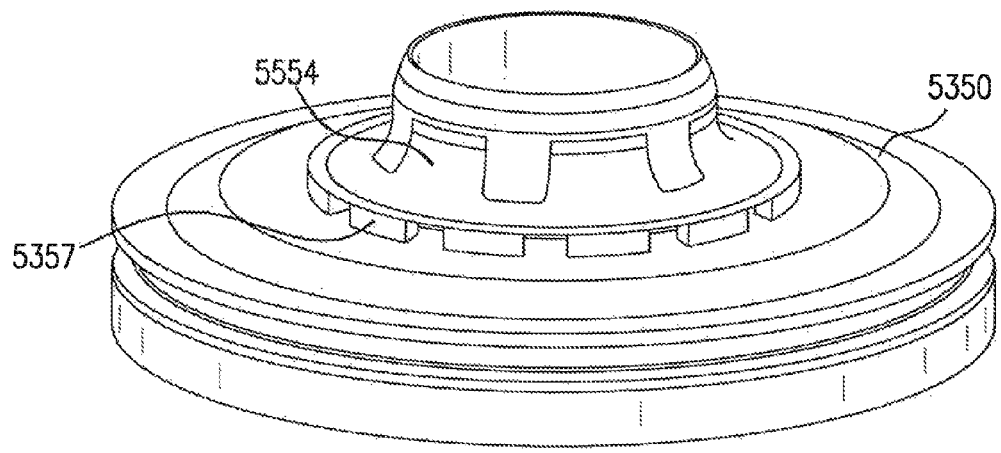

FIGS. 53-57 illustrate an alternate construction of a nozzle and associated components for a trocar in accordance with the invention. The nozzle assembly 5300 includes a lower substantially annular insert 5340, and an upper nozzle insert 5350. Standoffs 5357 are provided to space the components and to allow fluid to pass therethrough, which in the illustrated embodiment are provided on the nozzle insert 5330 (FIG. 56). As with the above-described embodiment, a diverter 5348 can be provided and aligned with a pressurized fluid inlet to diffuse an incoming stream of fluid within the fluid supply plenum 3641, to more effectively distribute fluid flow about the plenum 3641, and thus through the nozzle 3665.

Figure 57:
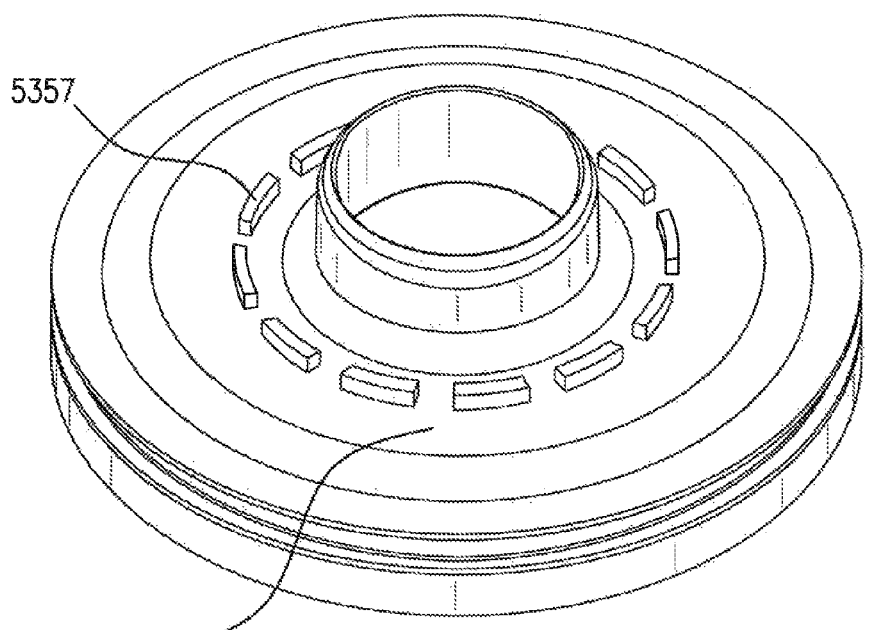

As best seen in FIGS. 54-56, a nozzle spacer 5554 is provided to help define a nozzle in trocars according to the invention. The nozzle spacer 5554 is placed between a compatible annular insert 5340 and nozzle insert 5350. As illustrated, a plurality of standoffs 5357 are provided on the nozzle insert 5350, while a diverter 5348 is provided on the annular insert 5340, although these elements can be embodied separately or on one or the other component. The nozzle spacer 5554 is provided to maintain a consistent width of the nozzle 3655. As described hereinabove, the nozzle 3655 can be essentially a continuous annulus. Alternatively, as shown in FIGS. 53-57, the nozzle 3665 if formed of an annular array of discrete jets that coincide with notches 5552 (FIG. 55) of the nozzle spacer 5554, between the annular insert 5340 and the nozzle insert 5350. The thickness of the tabs 5551 of the nozzle spacer 5554 determines the width of the nozzle 3655 in such an arrangement. In accordance with the invention, the nozzle spacer 5554 can be formed of a metal, formed as by stamping, so as to ensure relatively tight tolerances. In accordance with one exemplary embodiment of the invention, the thickness of the nozzle spacer 5554 is about 3/1000 inch (about 0.0762 mm). Although other materials can be used to form the spacer 5554, metal is capable of providing a more predictable nozzle width than molded polymeric components, which may be susceptible to molding irregularities or other irregularities encountered during molding. As illustrated in FIGS. 56 and 57, for example, the standoffs 5357 can serve to align and maintain the position of the nozzle spacer 5554 in the assembly 5300. Such positional constraint can server to promote the overall stability and durability of the assembly 5300 and the trocar in which it is provided, as a whole.

FIG. 58-63 illustrate optional proximal cap assemblies and associated features. Such caps can be used to close off the proximal end of the lumen of trocars in accordance with the invention, when desired to reduce noise in the operating room and/or to reduce loss of insufflation fluid to the operating room, for example.

Figure 58:
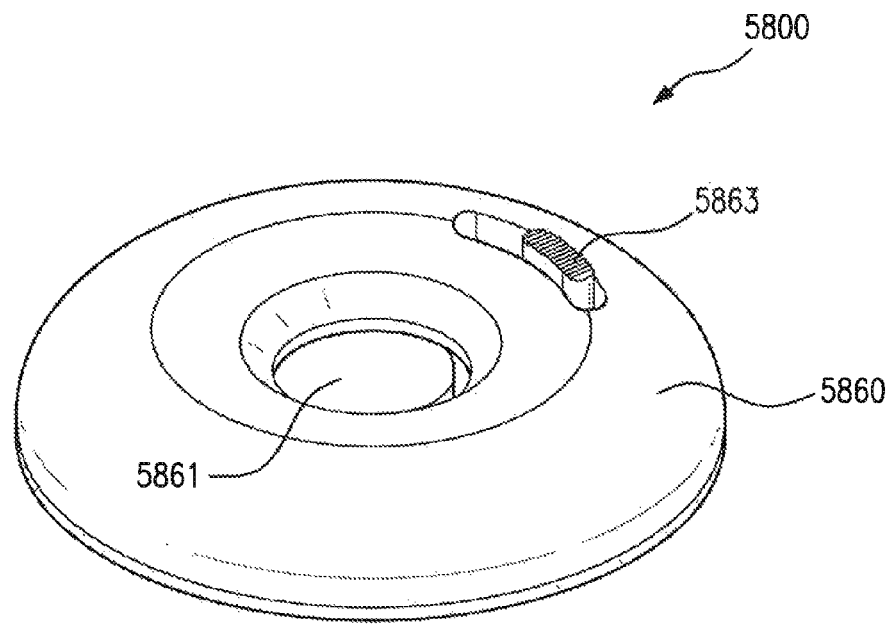
FIG. 58-59 illustrate one embodiment of a closeable proximal end cap for surgical access devices in accordance with the invention.
Figure 59:
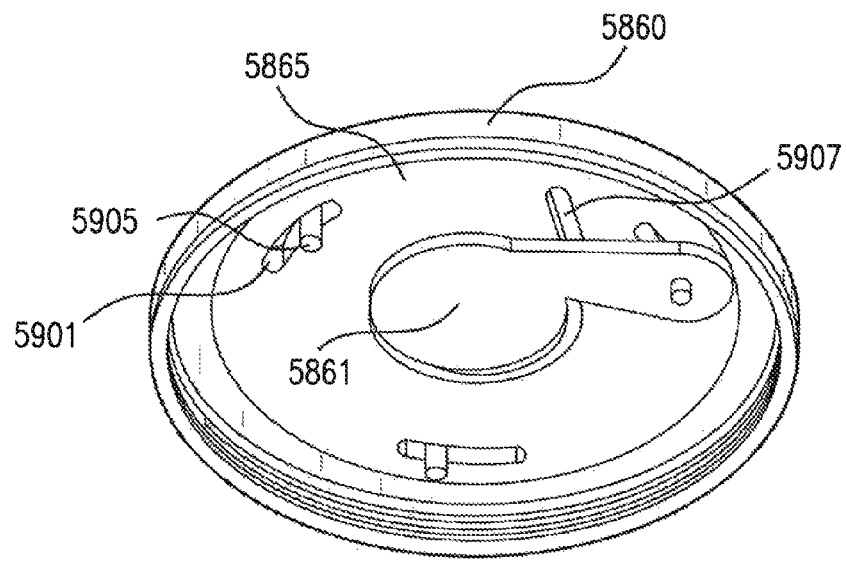
Figure 60:
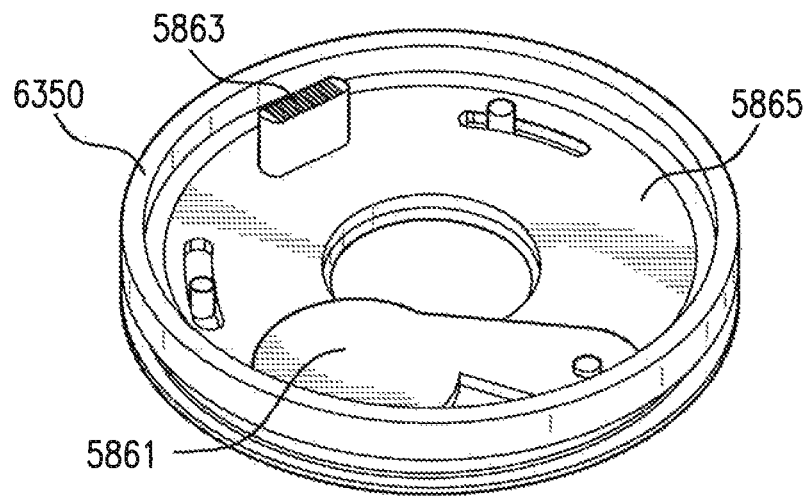
FIGS. 60-63 illustrate an alternate embodiment of a closeable proximal end cap for surgical access devices in accordance with the invention.
Figure 61:
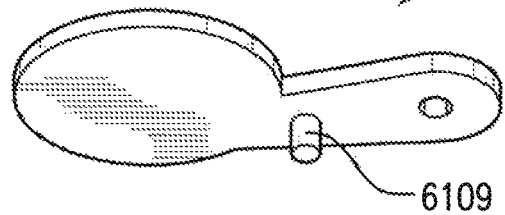
Figure 62:
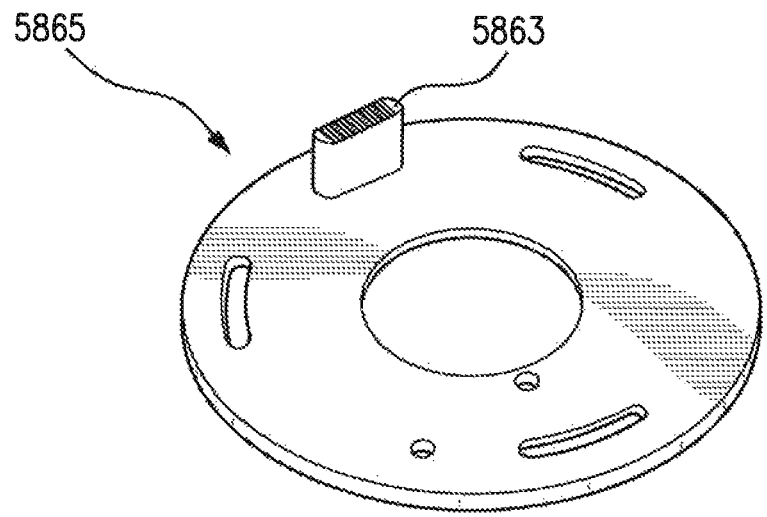
Figure 63:
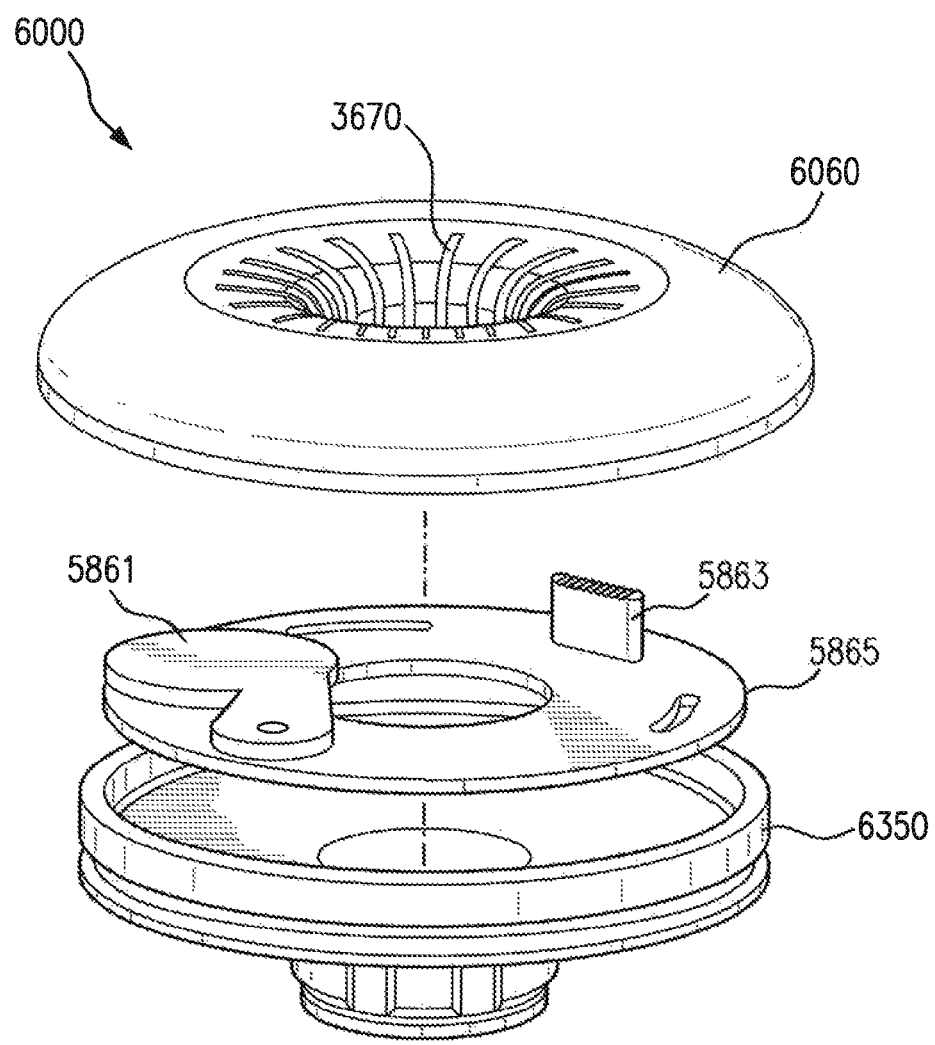

FIGS. 58-59 illustrate a cap 5800 without integral sound attenuation materials, having an outer housing portion 5860, an actuation ring 5865, and a shutter 5861. The actuation ring 5865 includes an extension 5863, which extends through the housing portion 5860, and is moved by the user to rotate the actuation ring 5865, to pivot the shutter 5861 axially centrally. In the cap 5800, all components are secured from above to the housing portion 5860. When the shutter is open, it does not obstruct the lumen of the trocar, and when the shutter 5861 is closed, the lumen is closed off. When the actuation ring 5865 is rotated, slots 5901 defined therein ride on pins 5905 extending from the housing portion 5860, which allow a mating portion of the shutter 5861, in this case, a pin 6109, engaged in a mating aperture formed in the actuation ring 5865 to cause axially central rotation of the shutter 5861. The mating aperture in the actuation ring 5865 can be a matching hole, a straight or curved slot, or any feature necessary to allow the relative motion of the components as described. If desired, one or more resilient seals can be provided at the juncture between the housing portion 5860 and the shutter 5861 to enhance a seal therebetween.

FIGS. 60-63 illustrate an alternate embodiment of a cap 6000 constructed in accordance with the invention designed to facilitate sound attenuation features, including internal sound attenuation materials. The cap 6000 again includes a shutter 5861, actuation ring 5865 and extension 5863. The housing portion 6060 includes sound attenuation apertures 3670 formed therein, the configuration of which can be as illustrated, or can vary therefrom, as desired or required. In the cap 6000, the components of the shutter mechanism are mounted from below to a separate component, which in the illustrated embodiment is a modified nozzle insert 6350. The modified nozzle insert 6350 includes posts to guide the moving parts of the cap 6000. The relative motion of the components of the cap 6000 is similar to the above-described cap 5800. In each of the foregoing embodiments It is to be understood that various alternate embodiments of caps in accordance with the invention are possible. It is to be understood that the precise mechanism and placement of actuation portions can vary due to design requirements. Moreover, incorporation of one or more magnetically-responsive components is conceived, to allow actuation of a shutter by way of an external magnetic actuation device. Alternatively still, cap features described in U.S. patent application publication number US 2007/0088275, which is incorporated herein by reference in its entirety, can be provided, including but not limited to features such as ball valves and the like.

The devices, systems and related methods of the present invention, as described above and shown in the drawings, provide for advantageous systems for surgical insufflation and gas recirculation, and related devices and methods therefor. It will be apparent to those skilled in the art that various modifications and variations can be made in the devices, systems and methods of the present invention without departing from the spirit or scope of the invention. Thus, it is intended that the present invention include such modifications and variations.

What is claimed is:

1. A surgical access device comprising:
   a) an elongated outer tubular member having opposed proximal and distal end portions and having a longitudinal axis extending therethrough;
   b) an elongated inner tubular member having opposed proximal and distal end portions and being arranged coaxially within the outer tubular member, the inner tubular member defining a central lumen for introduction of a surgical instrument therethrough;
   c) an insufflation conduit defined between the inner and outer tubular members in communication with a source of humidified insufflation gas; and
   d) a plurality of apertures extending through an outer surface of the distal portion of the outer tubular member in fluid communication with the insufflation conduit and configured to laterally discharge humidified insufflation gas from the insufflation conduit into the peritoneum of a patient,
   wherein the distal end portion of the outer tubular member and the distal end portion of the inner tubular member cooperate to enclose the insufflation conduit such that the humidified insufflation gas is discharged only from the plurality of apertures.

2. The surgical access device of claim 1, wherein the insufflation conduit extends from a housing at the proximal portion of the surgical access device, the housing in communication with a supply conduit to facilitate supply of the humidified insufflation gas to the insufflation conduit.

3. The surgical access device of claim 1, wherein the source of humidified insufflation gas is external to the surgical access device.

4. A system for delivering humidified insufflation gas, comprising:
   a) a trocar assembly having an elongated outer tubular member having opposed proximal and distal end portions and having a longitudinal axis extending therethrough and an elongated inner tubular member having opposed proximal and distal end portions and being arranged coaxially within the outer tubular member so as to form an insufflation conduit therebetween that extends from the proximal end portion of the outer tubular member to the distal end portion of the outer tubular member, the inner tubular member defining a central lumen for introduction of a surgical instrument therethrough, the insufflation conduit being in fluid communication with a plurality of apertures extending through an outer surface of the distal portion of the outer tubular member, and
   b) a source of humidified insufflation gas in fluid communication with the insufflation conduit,
   wherein humidified insufflation gas is laterally discharged from the plurality of apertures into the peritoneum of a patient and wherein the distal end portion of the outer tubular member and the distal end portion of the inner tubular member cooperate to enclose the insufflation conduit such that the humidified insufflation gas is discharged only from the plurality of apertures.

5. The system of claim 4, wherein the insufflation conduit extends from a housing at the proximal portion of the trocar assembly, the housing in communication with a supply conduit to facilitate supply of the humidified insufflation gas to the insufflation conduit.

6. The system of claim 4, wherein the source of humidified a insufflation gas is external to the trocar assembly.

7. A surgical access device comprising:
   a) an elongated outer tubular member having opposed proximal and distal end portions and having a longitudinal axis extending therethrough;
   b) an elongated inner tubular member having opposed proximal and distal end portion and being arranged coaxially within the outer tubular member, the inner tubular member defining a central lumen for introduction of a surgical instrument therethrough;
   c) an insufflation conduit defined between the inner and outer tubular members in communication with a source of conditioned insufflation gas; and
   d) a plurality of apertures extending through an outer surface of the distal portion of the outer tubular member in fluid communication with the insufflation conduit and configured to radially discharge conditioned insufflation gas from the insufflation conduit into the peritoneum of a patient,
   wherein the distal end portion of the outer tubular member and the distal end portion of the inner tubular member cooperate to enclose the insufflation conduit such that the conditioned insufflation gas is discharged only from the plurality of apertures.

8. The surgical access device of claim 7, wherein the insufflation conduit extends from a housing at the proximal portion of the surgical access device, the housing in communication with a supply conduit to facilitate supply of the conditioned insufflation gas to the insufflation conduit.

9. The surgical access device of claim 7, wherein the source of conditioned insufflation gas is external to the surgical access device.

10. The surgical access device of claim 7, wherein the conditioned insufflation gas is humidified insufflation gas.

11. The surgical access device of claim 7, wherein the conditioned insufflation gas is heated insufflation gas.

* * * * *

(12) INTER PARTES REVIEW CERTIFICATE (1992nd)
United States Patent
Stearns et al.

(10) Number: US 9,095,372 K1
(45) Certificate Issued: Mar. 29, 2021

(54) SYSTEM AND METHOD FOR IMPROVED GAS RECIRCULATION IN SURGICAL TROCARS WITH PNEUMATIC SEALING

(71) Applicant: SurgiQuest, Inc.

(72) Inventors: Ralph Stearns; Kurt Azarbarzin; Timothy J. Nolan

(73) Assignee: SurgiQuest, Inc.

Trial Number:
IPR2017-00518 filed Dec. 21, 2016

Inter Partes Review Certificate for:
Patent No.: 9,095,372
Issued: Aug. 4, 2015
Appl. No.: 14/298,419
Filed: Jun. 6, 2014

The results of IPR2017-00518 are reflected in this inter partes review certificate under 35 U.S.C. 318(b).

INTER PARTES REVIEW CERTIFICATE
U.S. Patent 9,095,372 K1
Trial No. IPR2017-00518
Certificate Issued Mar. 29, 2021

AS A RESULT OF THE INTER PARTES REVIEW PROCEEDING, IT HAS BEEN DETERMINED THAT:

Claims 1-11 are cancelled.

\* \* \* \* \*